US012569572B2

(12) United States Patent
Heartlein et al.

(10) Patent No.: US 12,569,572 B2
(45) Date of Patent: Mar. 10, 2026

(54) MESSENGER RNA THERAPY FOR THE TREATMENT OF FRIEDREICH'S ATAXIA

(71) Applicant: Translate Bio, Inc., Lexington, MA (US)

(72) Inventors: Michael Heartlein, Lexington, MA (US); Frank DeRosa, Lexington, MA (US); Jonathan Cherry, Lexington, MA (US); Paula Lewis, Lexington, MA (US); Shrirang Karve, Lexington, MA (US); Zarna Patel, Lexington, MA (US); Darshan Parekh, Lexington, MA (US); Susan Wood, Lexington, MA (US); Chi-Sung Chiu, Lexington, MA (US); Caroline J. Woo, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 804 days.

(21) Appl. No.: 17/016,860

(22) Filed: Sep. 10, 2020

(65) Prior Publication Data

US 2021/0187122 A1 Jun. 24, 2021

Related U.S. Application Data

(62) Division of application No. 16/012,138, filed on Jun. 19, 2018, now Pat. No. 10,780,183.

(Continued)

(51) Int. Cl.

*A61P 21/00* (2006.01)
*A61K 9/00* (2006.01)

(Continued)

(52) U.S. Cl.

CPC .......... *A61K 48/005* (2013.01); *A61K 9/0019* (2013.01); *A61K 9/0087* (2013.01); *A61K 9/107* (2013.01); *A61K 9/127* (2013.01); *A61K 31/7088* (2013.01); *A61K 38/02* (2013.01); *A61K 38/1709* (2013.01); *A61P 21/00* (2018.01); *A61P 43/00* (2018.01); *C12N 15/52* (2013.01); *C12N 15/62* (2013.01); *C12N 15/88* (2013.01)

(58) Field of Classification Search

None

See application file for complete search history.

(56) References Cited

U.S. PATENT DOCUMENTS

2015/0110857 A1 4/2015 DeRosa et al.
2019/0175757 A1 6/2019 Fotin-Mleczek et al.

FOREIGN PATENT DOCUMENTS

WO WO 2019/207060 A1 10/2019

OTHER PUBLICATIONS

Nabhan, J., Wood, K., Rao, V. et al. Intrathecal delivery of frataxin mRNA encapsulated in lipid nanoparticles to dorsal root ganglia as a potential therapeutic for Friedreich's ataxia. Sci Rep 6, 20019 (2016). (Year: 2016).*

(Continued)

*Primary Examiner* — Aurora M Fontainhas

(74) *Attorney, Agent, or Firm* — LATHROP GPM LLP; James H. Velema, Esq.

(57) ABSTRACT

The present invention provides methods and compositions of treating Friedreich's ataxia (FRDA) based on administering an mRNA encoding a frataxin protein.

14 Claims, 16 Drawing Sheets

Specification includes a Sequence Listing.

Related U.S. Application Data

(60) Provisional application No. 62/521,734, filed on Jun. 19, 2017.

(51) Int. Cl.

| | |
|---|---|
| ***A61K 9/107*** | (2006.01) |
| ***A61K 9/127*** | (2025.01) |
| ***A61K 31/7088*** | (2006.01) |
| ***A61K 38/02*** | (2006.01) |
| ***A61K 38/17*** | (2006.01) |
| ***A61K 48/00*** | (2006.01) |
| ***A61P 43/00*** | (2006.01) |
| ***C12N 15/52*** | (2006.01) |
| ***C12N 15/62*** | (2006.01) |
| ***C12N 15/88*** | (2006.01) |

(56) References Cited

OTHER PUBLICATIONS

Mauro et al., A critical analysis of codon optimization in human therapeutics. Trends Mol Med. Nov. 2014;20(11):604-13. (Year: 2014).*

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research Efficacy and Mechanism Evaluation, vol. 3, No. 5, Jul. 2016, pp. 1-210, DOI: 10.3310/eme03050 (240 pages).

International Search Report and Written Opinion for PCT/US2018/038252 dated Aug. 30, 2018 (11 pages).

Kauffman et al., "Optimization of Lipid Nanoparticle Formulations for mRNA Delivery in Vivo with Fractional Factorial and Definitive Screening Designs", Nano Letters, vol. 15, No. 11, 2015, pp. 7300-7306, DOI: 10.1021/acs.nanolett.5b02497 (7 pages).

Nabhan et al., "Intrathecal delivery of frataxin mRNA encapsulated in lipid nanoparticles to dorsal root ganglia as a potential therapeutic for Friedreich's ataxia", Scientific Reports, Supp Info, vol. 6, Feb. 17, 2016, DOI: 10.1038/srep20019 (8 pages).

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016).

International Search Report and Written Opinion for PCT/US18/38252, dated Aug. 30, 2018.

* cited by examiner

Note: Values adjusted to 1.0 ug/well total protein based on loading 2.5 ng/well (values multiplied by 400)

Note: Values adjusted to 1.0 ug/well total protein based on loading 3 ug/well (values divided by 3)

15 µg total protein/lane
HEK = 0.5µg HEK cell lysate positive control
Liver = 2.5 µg liver sample #20 (MRT1 1 mg/kg) positive control 15 μg total protein/lane
HEK = 0.5μg HEK cell lysate positive control
Liver = 2.5 μg liver sample #20 (MRT1 1 mg/kg) positive control 2.5 μg total protein/lane
HEK = 0.5 μg HEK cell lysate positive control
Liver = 2.5 μg liver sample #20 (MRT1 mg/kg) positive control Note: Values adjusted to 1.0 ug/well total protein based on loading 0.018 ug/well (values multiplied by 55).

Note: Values adjusted to 1.0 ug/well total protein based on loading 5 ug/well (values divided by 5).

SEQUENCE LISTING

```
<160> NUMBER OF SEQ ID NOS: 16

<210> SEQ ID NO 1
<211> LENGTH: 633
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

auguggaccc ugggucggag agcuguggcc ggucugcugg cuucccccuc accggcacaa     60

gcgcagaccc ugacuagagu gccuaggccc gcugaacucg caccacugug cggcagacgg    120

ggacuccgga cugacaucga ugccaccugu accccgcgaa gggcaucuag caaucagcgc    180

ggacugaacc agaucuggaa cgugaagaag caguccgugu accugaugaa ucugcgcaaa    240

uccggcacuc ucggacaccc gggaucgcug gaugagacua cuuacgagcg cuuggccgaa    300

gaaacccugg auucgcuggc cgaguuuuuc gaggaccugg ccgacaagcc cuacacguuc    360

gaggacuacg acguguccuu cggaucgggc gugcugaccg ugaagcucgg cggggauuug    420

gggaccuacg ugaucaacaa gcagacaccg aacaagcaaa uuuggcucuc cuccccuucc    480

uccggaccua agcgcuacga cuggaccggg aagaacuggg ucuacuccca ugacggcguc    540

agccuucacg aacugcuggc cgccgaacug acuaaggccc ucaaaacuaa gcuggaccug    600

ucgagccuug ccuauuccgg aaaggacgcc uga                                 633


<210> SEQ ID NO 2
<211> LENGTH: 633
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

auguggaccc ugggacgcag agccguggcu ggccuucugg ccuccccaag cccugcccaa     60

gcccagaccu ugacuagagu gccuagaccg gccgaacucg cuccccugug cggacggagg    120

ggacucagga cugacaucga cgcaacaugc acuccaagac gcgccuccag caaccagcgg    180

ggccucaacc agauuuggaa cgugaaaaag caguccgucu aucugaugaa ccuccgcaag    240

uccggcaccu uggggcaucc cgggucacug gaugaaacca ccuacgaacg gcuggccgaa    300

gagacucucg acucccuggc cgaguucuuc gaggaccugg cggauaagcc guacacuuuc    360

gaggacuacg augucucuuu cggauccggc gugcugaccg ugaagcucgg uggcgaccuc    420

ggaacuuacg ugaucaacaa gcaaacgccc aacaagcaga ucuggcuguc cucgccguca    480

ucgggaccua agcgcuacga uuggaccggg aagaauuggg uguacucgca cgacggugc    540

agccugcacg agcugcuugc ggcggaacug accaaggcac ucaagaccaa acuggaccug    600
```

uccagccugg ccuacuccgg aaaggacgcc uag 633

<210> SEQ ID NO 3
<211> LENGTH: 633
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3
auguggacuc ugggccggag agcuguggca ggccuucucg ccucgccauc cccugcccaa 60
gcgcagaccc ugacuagggu cccuaggccu gccgaguugg caccguugug cggucggaga 120
ggacugcgca ccgacaucga ugccaccugu acuccucgga gagccucguc caaccagcgg 180
ggccugaacc agaucuggaa cgugaagaaa caguccgucu accugaugaa ccuccgcaag 240
ucgggaaccc ugggacaucc ggguucccug gaugagacua cguacgaacg gcuggcggaa 300
gaaacccugg acucccuggc ggaguucuuc gaggaccugg cugacaagcc cuacacuuuu 360
gaggacuacg acgugucauu cggaagcgga guguugacag ugaagcuggg gggcgaucug 420
ggaaccuacg ugaucaacaa gcagaccccg aacaagcaaa uuuggcuguc cucacccucc 480
uccggaccua aacgcuacga cuggaccggg aagaacuggg uguauagcca cgacggugac 540
agccuucacg aacugcuugc ggccgaacug accaaggccc ucaagaccaa gcucgaucug 600
ucuagccucg ccuacuccgg aaaggacgcc uga 633

<210> SEQ ID NO 4
<211> LENGTH: 633
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4
auguggaccu ugggacggag agccguggcu ggacuguugg ccucuccuuc cccggcacaa 60
gcccaaacuc ugacccgggu cccuagaccg gcagagcugg cuccccugug uggucggcgg 120
ggacugagaa cugauauuga cgccacaugc acuccuaggc gcgcgagcuc caaucagcgc 180
ggccugaacc agaucuggaa cgugaagaag caguccgucu acuugaugaa ccuccgcaag 240
uccggcacuc ugggccaucc gggaucccuc gacgagacua ccuacgagcg gcuggcggaa 300
gaaacccugg auucccuggc cgaauucuuc gaggaccugg ccgacaagcc cuacaccuuu 360
gaggacuacg acguguccuu cggaucggga gugcugaccg ugaagcucgg cggagaucuc 420
gggacuuaug ugaucaacaa gcagacgccg aacaagcaga ucuggcuuag cucacccucg 480
agcggaccaa agcgcuacga cuggaccggc aaaaacuggg uguacuccca cgauggugac 540
agccuucacg aacugcuggc cgcggaacug accaaggccc uuaagaccaa gcucgaccuc 600
ucaucccugg ccuacuccgg gaaagacgcg uga 633

<210> SEQ ID NO 5
<211> LENGTH: 210
<212> TYPE: PRT
<213> ORGANISM: Homo sapiens

<400> SEQUENCE: 5

Met Trp Thr Leu Gly Arg Arg Ala Val Ala Gly Leu Leu Ala Ser Pro

-continued 1 5 10 15

Ser Pro Ala Gln Ala Gln Thr Leu Thr Arg Val Pro Arg Pro Ala Glu
20 25 30

Leu Ala Pro Leu Cys Gly Arg Arg Gly Leu Arg Thr Asp Ile Asp Ala
35 40 45

Thr Cys Thr Pro Arg Arg Ala Ser Ser Asn Gln Arg Gly Leu Asn Gln
50 55 60

Ile Trp Asn Val Lys Lys Gln Ser Val Tyr Leu Met Asn Leu Arg Lys
65 70 75 80

Ser Gly Thr Leu Gly His Pro Gly Ser Leu Asp Glu Thr Thr Tyr Glu
85 90 95

Arg Leu Ala Glu Glu Thr Leu Asp Ser Leu Ala Glu Phe Phe Glu Asp
100 105 110

Leu Ala Asp Lys Pro Tyr Thr Phe Glu Asp Tyr Asp Val Ser Phe Gly
115 120 125

Ser Gly Val Leu Thr Val Lys Leu Gly Gly Asp Leu Gly Thr Tyr Val
130 135 140

Ile Asn Lys Gln Thr Pro Asn Lys Gln Ile Trp Leu Ser Ser Pro Ser
145 150 155 160

Ser Gly Pro Lys Arg Tyr Asp Trp Thr Gly Lys Asn Trp Val Tyr Ser
165 170 175

His Asp Gly Val Ser Leu His Glu Leu Leu Ala Ala Glu Leu Thr Lys
180 185 190

Ala Leu Lys Thr Lys Leu Asp Leu Ser Ser Leu Ala Tyr Ser Gly Lys
195 200 205

Asp Ala
210

<210> SEQ ID NO 6
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 7
<211> LENGTH: 105
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
cggguggcau cccugugacc ccucccccagu gccucuccug gcccuggaag uugccacucc 60
agugcccacc agccuugucc uaauaaaauu aaguugcauc aagcu 105

<210> SEQ ID NO 8
<211> LENGTH: 105
<212> TYPE: RNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8 gggugcauc ccugugaccc cuccccagug ccucuccugg cccuggaagu ugccacucca 60
gugcccacca gccuuguccu aauaaaauua aguugcauca aagcu 105

<210> SEQ ID NO 9
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggaccc ugggucggag agcuguggcc ggucugcugg 180
cuucccccuc accggcacaa gcgcagaccc ugacuagagu gccuaggccc gcugaacucg 240
caccacugug cggcagacgg ggacuccgga cugacaucga ugccaccugu accccgcgaa 300
gggcaucuag caaucagcgc ggacugaacc agaucuggaa cgugaagaag caguccgugu 360
accugaugaa ucugcgcaaa uccggcacuc ucggacaccc gggaucgcug gaugagacua 420
cuuacgagcg cuuggccgaa gaaacccugg auucgcuggc cgaguuuuuc gaggaccugg 480
ccgacaagcc cuacacguuc gaggacuacg acguguccuu cggaucgggc gugcugaccg 540
ugaagcucgg cggggauuug gggaccuacg ugaucaacaa gcagacaccg aacaagcaaa 600
uuuggcucuc cuccccuucc uccggaccua agcgcuacga cuggaccggg aagaacuggg 660
ucuacuccca ugacggcguc agccuucacg aacugcuggc cgccgaacug acuaaggccc 720
ucaaaacuaa gcuggaccug ucgagccuug ccuauuccgg aaaggacgcc ugacgggugg 780
caucccugug accccucccc agugccucuc cuggcccugg aaguugccac uccagugccc 840
accagccuug uccuaauaaa auuaaguugc aucaagcu 878

<210> SEQ ID NO 10
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggaccc ugggucggag agcuguggcc ggucugcugg 180
cuucccccuc accggcacaa gcgcagaccc ugacuagagu gccuaggccc gcugaacucg 240
caccacugug cggcagacgg ggacuccgga cugacaucga ugccaccugu accccgcgaa 300
gggcaucuag caaucagcgc ggacugaacc agaucuggaa cgugaagaag caguccgugu 360
accugaugaa ucugcgcaaa uccggcacuc ucggacaccc gggaucgcug gaugagacua 420
cuuacgagcg cuuggccgaa gaaacccugg auucgcuggc cgaguuuuuc gaggaccugg 480
ccgacaagcc cuacacguuc gaggacuacg acguguccuu cggaucgggc gugcugaccg 540
ugaagcucgg cggggauuug gggaccuacg ugaucaacaa gcagacaccg aacaagcaaa 600
uuuggcucuc cuccccuucc uccggaccua agcgcuacga cuggaccggg aagaacuggg 660
ucuacuccca ugacggcguc agccuucacg aacugcuggc cgccgaacug acuaaggccc 720
ucaaaacuaa gcuggaccug ucgagccuug ccuauuccgg aaaggacgcc ugagggugge 780 aucccuguga ccccucccca gugccucucc uggcccugga aguugccacu ccagugccca 840
ccagccuugu ccuaauaaaa uuaaguugca ucaaagcu 878

<210> SEQ ID NO 11
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 11
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggaccc ugggacgcag agccguggcu ggccuucugg 180
ccuccccaag cccugcccaa gcccagaccu ugacuagagu gccuagaccg gccgaacucg 240
cuccccugug cggacggagg ggacucagga cugacaucga cgcaacaugc acuccaagac 300
gcgccuccag caaccagcgg ggccucaacc agauuuggaa cgugaaaaag caguccgucu 360
aucugaugaa ccuccgcaag uccggcaccu uggggcaucc cgggucacug gaugaaacca 420
ccuacgaacg gcuggccgaa gagacucucg acucccuggc cgaguucuuc gaggaccugg 480
cggauaagcc guacacuuuc gaggacuacg augucucuuu cggauccggc gugcugaccg 540
ugaagcucgg uggcgaccuc ggaacuuacg ugaucaacaa gcaaacgccc aacaagcaga 600
ucuggcuguc cucgccguca ucgggaccua agcgcuacga uuggaccggg aagaauuggg 660
uguacucgca cgacggugue agccugcacg agcugcuugc ggcggaacug accaaggcac 720
ucaagaccaa acuggaccug uccagccugg ccuacuccgg aaaggacgcc uagcgggugg 780
caucccugug accccucccc agugccucuc cuggcccugg aaguugccac uccagugccc 840
accagccuug uccuaauaaa auuaaguugc aucaagcu 878

<210> SEQ ID NO 12
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 12
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggaccc ugggacgcag agccguggcu ggccuucugg 180
ccuccccaag cccugcccaa gcccagaccu ugacuagagu gccuagaccg gccgaacucg 240
cuccccugug cggacggagg ggacucagga cugacaucga cgcaacaugc acuccaagac 300
gcgccuccag caaccagcgg ggccucaacc agauuuggaa cgugaaaaag caguccgucu 360
aucugaugaa ccuccgcaag uccggcaccu uggggcaucc cgggucacug gaugaaacca 420
ccuacgaacg gcuggccgaa gagacucucg acucccuggc cgaguucuuc gaggaccugg 480
cggauaagcc guacacuuuc gaggacuacg augucucuuu cggauccggc gugcugaccg 540
ugaagcucgg uggcgaccuc ggaacuuacg ugaucaacaa gcaaacgccc aacaagcaga 600
ucuggcuguc cucgccguca ucgggaccua agcgcuacga uuggaccggg aagaauuggg 660
uguacucgca cgacggugu c agccugcacg agcugcuugc ggcggaacug accaaggcac 720
ucaagaccaa acuggaccug uccagccugg ccuacuccgg aaaggacgcc uaggggugge 780 aucccuguga ccccuccccca gugccucucc uggcccugga aguugccacu ccagugccca 840
ccagccuugu ccuaauaaaa uuaaguugca ucaaagcu 878

<210> SEQ ID NO 13
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 13
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggacuc ugggccggag agcuguggca ggccuucucg 180
ccucgccauc cccugcccaa gcgcagaccc ugacuagggu cccuaggccu gccgaguugg 240
caccguugug cggucggaga ggacugcgca ccgacaucga ugccaccugu acuccucgga 300
gagccucguc caaccagcgg ggccugaacc agaucuggaa cgugaagaaa caguccgucu 360
accugaugaa ccuccgcaag ucgggaaccc ugggacaucc ggguucccug gaugagacua 420
cguacgaacg gcuggcggaa gaaacccugg acucccuggc ggaguucuuc gaggaccugg 480
cugacaagcc cuacacuuuu gaggacuacg acgugucauu cggaagcgga guguugacag 540
ugaagcuggg gggcgaucug ggaaccuacg ugaucaacaa gcagaccccg aacaagcaaa 600
uuuggcuguc cucacccucc uccggaccua aacgcuacga cuggaccggg aagaacuggg 660
uguauagcca cgacggugu c agccuucacg aacugcuugc ggccgaacug accaaggccc 720
ucaagaccaa gcucgaucug ucuagccucg ccuacuccgg aaaggacgcc ugacgggugg 780
caucccugug accccucccc agugccucuc cuggcccugg aaguugccac uccagugccc 840
accagccuug uccuaauaaa auuaaguugc aucaagcu 878

<210> SEQ ID NO 14
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 14
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggacuc ugggccggag agcuguggca ggccuucucg 180
ccucgccauc cccugcccaa gcgcagaccc ugacuagggu ccccuaggccu gccgaguugg 240 caccguugug cggucggaga ggacugcgca ccgacaucga ugccaccugu acuccucgga 300
gagccucguc caaccagcgg ggccugaacc agaucuggaa cgugaagaaa caguccgucu 360
accugaugaa ccuccgcaag ucgggaaccc ugggacaucc ggguucccug gaugagacua 420
cguacgaacg gcuggcggaa gaaacccugg acucccuggc ggaguucuuc gaggaccugg 480
cugacaagcc cuacacuuuu gaggacuacg acgugucauu cggaagcgga guguugacag 540
ugaagcuggg gggcgaucug ggaaccuacg ugaucaacaa gcagaccccg aacaagcaaa 600
uuuggcuguc cucacccucc uccggaccua aacgcuacga cuggaccggg aagaacuggg 660
uguauagcca cgacggugue agccuucacg aacugcuugc ggccgaacug accaaggccc 720
ucaagaccaa gcucgaucug ucuagccucg ccuacuccgg aaaggacgcc ugagggugge 780 aucccuguga ccccuccccca gugccucucc uggcccugga aguugccacu ccagugccca 840
ccagccuugu ccuaauaaaa uuaaguugca ucaaagcu 878

<210> SEQ ID NO 15
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg auguggaccu ugggacggag agccguggcu ggacuguugg 180
ccucuccuuc cccggcacaa gcccaaacuc ugacccgggu ccccuagaccg gcagagcugg 240 cuccccugug uggucggcgg ggacugagaa cugauauuga cgccacaugc acuccuaggc 300
gcgcgagcuc caaucagcgc ggccugaacc agaucuggaa cgugaagaag caguccgucu 360
acuugaugaa ccuccgcaag uccggcacuc ugggccaucc gggaucccuc gacgagacua 420
ccuacgagcg gcuggcggaa gaaacccugg auucccuggc cgaauucuuc gaggaccugg 480
ccgacaagcc cuacaccuuu gaggacuacg acguguccuu cggaucggga gugcugaccg 540
ugaagcucgg cggagaucuc gggacuuaug ugaucaacaa gcagacgccg aacaagcaga 600
ucuggcuuag cucacccucg agcggaccaa agcgcuacga cuggaccggc aaaaacuggg 660
uguacuccca cgauggugue agccuucacg aacugcuggc cgcggaacug accaaggccc 720
uuaagaccaa gcucgaccuc ucaucccugg ccuacuccgg gaaagacgcg ugacgggugg 780
caucccugug accccucccc agugccucuc cuggcccugg aaguugccac uccagugccc 840
accagccuug uccuaauaaa auuaaguugc aucaagcu 878

<210> SEQ ID NO 16
<211> LENGTH: 878
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 16

```
ggacagaucg ccuggagacg ccauccacgc uguuuugacc uccauagaag acaccgggac     60
cgauccagcc uccgcggccg ggaacggugc auuggaacgc ggauuccccg ugccaagagu    120
gacucaccgu ccuugacacg auguggaccu ugggacggag agccguggcu ggacuguugg    180
ccucuccuuc cccggcacaa gcccaaacuc ugacccgggu cccuagaccg gcagagcugg    240
cuccccugug uggucggcgg ggacugagaa cugauauuga cgccacaugc acuccuaggc    300
gcgcgagcuc caaucagcgc ggccugaacc agaucuggaa cgugaagaag caguccgucu    360
acuugaugaa ccuccgcaag uccggcacuc ugggccaucc gggaucccuc gacgagacua    420
ccuacgagcg gcuggcggaa gaaacccugg auucccuggc cgaauucuuc gaggaccugg    480
ccgacaagcc cuacaccuuu gaggacuacg acguguccuu cggaucggga gugcugaccg    540
ugaagcucgg cggagaucuc gggacuuaug ugaucaacaa gcagacgccg aacaagcaga    600
ucuggcuuag cucacccucg agcggaccaa agcgcuacga cuggaccggc aaaaacuggg    660
uguacuccca cgauggugc agccuucacg aacugcuggc cgcggaacug accaaggccc    720
uuaagaccaa gcucgaccuc ucaucccugg ccuacuccgg gaaagacgcg ugagggugc     780
aucccuguga ccccucccca gugccucucc uggcccugga aguugccacu ccagugccca    840
ccagccuugu ccuaauaaaa uuaaguugca ucaaagcu                            878
```

MESSENGER RNA THERAPY FOR THE TREATMENT OF FRIEDREICH'S ATAXIA

CROSS REFERENCE TO RELATED APPLICATIONS

This application is a Divisional Application of U.S. application Ser. No. 16/012,138, filed Jun. 19, 2018, which claims priority to and the benefit of U.S. Provisional Application No. 62/521,734, filed Jun. 19, 2017, the disclosure of which is hereby incorporated by reference.

INCORPORATION BY REFERENCE OF SEQUENCE LISTING

The contents of the file named "MRT-2004US2_SequenceListing.txt", which was created on Sep. 3, 2020 and is 18,135 bytes in size, are hereby incorporated by reference.

BACKGROUND

Friedreich's ataxia (also called FA or FRDA) is a rare inherited disease that causes nervous system damage and movement problems. It usually begins in childhood and leads to impaired muscle coordination (ataxia) that worsens over time. In Friedreich's ataxia, the spinal cord, peripheral nerves and cerebellum degenerate. This damage results in awkward, unsteady movements and impaired sensory functions. The disorder also causes problems in the heart and spine, and some people with the condition develop diabetes.

Friedreich's ataxia is caused by a defect (mutation) in the FXN gene that encodes the protein frataxin. This protein is found in cells throughout the body, with the highest levels in the heart, spinal cord, liver, pancreas, and muscles used for voluntary movement (skeletal muscles). Within cells, frataxin is found in energy-producing structures called mitochondria. Although its function is not fully understood, frataxin appears to help assemble clusters of iron and sulfur molecules that are critical for the function of many proteins, including those needed for energy production. One region of the FXN gene contains a segment of DNA known as a GAA trinucleotide repeat. In most people, the number of GAA repeats in the FXN gene is fewer than 12 (referred to as short normal). Sometimes, however, the GAA segment is repeated 12 to 33 times (referred to as long normal).

Friedreich's ataxia results from an increased number of copies (expansion) of the GAA trinucleotide repeat in the FXN gene. In people with this condition, the GAA segment is abnormally repeated 66 to more than 1,000 times. The length of the GAA trinucleotide repeat appears to be related to the age at which the symptoms of Friedreich's ataxia appear. People with GAA segments repeated fewer than 300 times tend to have a later appearance of symptoms (after age 25) than those with larger GAA trinucleotide repeats.

Most individuals with Friedreich's ataxia have the expanded GAA trinucleotide repeat in both copies of the FXN gene. It is not fully understood how FXN gene mutations cause Friedreich's ataxia. Mutations in this gene disrupt production of frataxin, greatly reducing the amount of this protein in cells. A shortage of frataxin appears to decrease the activity of proteins that contain iron-sulfur clusters, which could impair the production of energy in mitochondria. Cells with insufficient amounts of frataxin are also particularly sensitive to reactive molecules (free radicals) that can damage and destroy cells. Cells in the brain, spinal cord, and muscles that are damaged or have inadequate energy supplies may not function properly, leading to the signs and symptoms of Friedreich's ataxia.

As with many degenerative diseases of the nervous system, there is currently no cure or effective treatment for Friedreich's ataxia. However, many of the symptoms and accompanying complications can be treated to help individuals maintain optimal functioning as long as possible. Doctors can prescribe treatments for diabetes, if present; some of the heart problems can be treated with medication as well. Orthopedic problems such as foot deformities and scoliosis can be corrected with braces or surgery, while physical therapy may prolong use of the arms and legs.

SUMMARY OF THE INVENTION

The present invention provides, among other things, improved methods and compositions for the treatment of Friedreich's ataxia (FRDA) based on mRNA therapy. The invention encompasses the observation that administration of an mRNA encoding a human frataxin (FXN) protein, encapsulated within a liposome, resulted in highly efficient and sustained protein production in vivo.

In one aspect, the present invention provides methods of treating Friedreich's ataxia (FRDA), comprising administering to a subject in need of treatment a composition comprising an mRNA encoding a frataxin protein.

In another aspect, the present invention generally provides methods of delivering frataxin in vivo, comprising administering periodically to a subject in need of delivery a composition comprising an mRNA encoding a frataxin protein such that the frataxin protein is expressed in vivo at a level sufficient to achieve therapeutic efficacy (e.g., a level of at least 10% of a normal control level).

In still another aspect, the present invention provides pharmaceutical compositions for treating Friedreich's ataxia (FRDA) containing an mRNA encoding a frataxin protein.

In various embodiments according to the invention, an mRNA encoding a frataxin protein comprises a polynucleotide sequence at least 60%, 65%, 70%, 75%, 80%, 85%, 90%, or 95% identical to SEQ ID NO: 1, SEQ ID NO: 2, SEQ ID NO: 3, or SEQ ID NO: 4. In certain embodiments, an mRNA encoding a frataxin protein comprises a polynucleotide sequence at least 80% identical to SEQ ID NO: 1, SEQ ID NO: 2, SEQ ID NO: 3, or SEQ ID NO: 4. In certain embodiments, an mRNA encoding a frataxin protein comprises a polynucleotide sequence at least 90% identical to SEQ ID NO: 1, SEQ ID NO: 2, SEQ ID NO: 3, or SEQ ID NO: 4. In certain embodiments, an mRNA encoding a frataxin protein comprises a polynucleotide sequence at least 95% identical to SEQ ID NO: 1, SEQ ID NO: 2, SEQ ID NO: 3, or SEQ ID NO: 4. In certain embodiments, an mRNA encoding a frataxin protein comprises a polynucleotide sequence identical to SEQ ID NO: 1, SEQ ID NO: 2, SEQ ID NO: 3, or SEQ ID NO: 4.

In various embodiments, an mRNA encoding a frataxin protein is codon optimized. In some embodiments, the mRNA comprises a polynucleotide sequence wherein the percentage of guanine nucleotides is at least 28%, the percentage of cytosine nucleotides is at least 30%, the combined percentage of guanine and cytosine nucleotides is at least 59%, and/or the percentage of adenine nucleotides is no more than 22.5%. In some embodiments, the mRNA comprises a polynucleotide sequence wherein the percent change in the number of guanine nucleotides relative to a native human FXN mRNA sequence is at least is at least 9%, the percent change in the number of cytosine nucleotides relative to a native human FXN mRNA sequence is at least is at least 7%, the percent change in the combined number of guanine and cytosine nucleotides relative to a native human FXN mRNA is at least 9%, and/or the percent change in the number of adenine nucleotides relative to a native human FXN mRNA sequence is at least −7%.

In some embodiments, an mRNA further comprises a 5' untranslated region (UTR) and/or a 3' untranslated region (UTR). In some embodiments, the 5' UTR includes a sequence of SEQ ID NO: 6. In some embodiments, the 3' UTR includes a sequence of SEQ ID NO: 7 or SEQ ID NO: 8.

In some embodiments, the composition is administered to the subject via intravenous (IV) delivery. In some embodiments, the composition is administered to the subject via intrathecal (IT) delivery.

Typically, an mRNA encoding a frataxin protein is administered periodically (e.g., once a day, twice a week, once a week, once every other week, twice a month, once every 14 days, once a month, etc.). In some embodiments, the mRNA is administered once a week. In some embodiments, the mRNA is administered twice a month. In some embodiments, the mRNA is administered once every 14 days. In some embodiments, the mRNA is administered once a month.

In some embodiments, administration of the composition results in expression of the frataxin protein in various tissues in vivo. In some embodiments, administration of the composition results in expression of the frataxin protein detectable in the liver, the spinal cord, the brain, the cerebellum, and/or at least one dorsal root ganglion (DRG) of the subject. In some embodiments, the frataxin protein is detectable at least 1 day, 2 days, 3 days, 4 days, 5 days, 6 days, 1 week, or 2 weeks after administering the composition. In some embodiments, the frataxin protein is detectable at a level of at least 0.1 pg/μg of total protein, at least 0.5 pg/μg of total protein, at least 1.0 pg/μg of total protein, at least 5 pg/μg of total protein, at least 10 pg/μg of total protein, at least 50 pg/μg of total protein, or at least 100 pg/μg of total protein. In some embodiments, the frataxin protein is detectable at a level of at least 10%, 15%, 20%, 25%, 30%, 35%, 40%, 45%, or 50% of a normal control level. In some embodiments, the frataxin protein is detectable at a level of at least 10%, 20%, 30%, 40%, 50%, 1-fold, 1.5-fold, 2-fold, 2.5-fold, 3-fold, 3.5-fold, 4-fold, 4.5-fold or 5-fold greater than a control level indicative of untreated patient.

In some embodiments, the mRNA is administered at a dose of at least 1 μg, 2 μg, 3 μg, 4 μg, 5 μg, 6 μg, 7 μg, 8 μg, 9 μg, 10 μg, 15 μg, or 20 μg.

In various embodiments, the mRNA is encapsulated within a liposome. In some embodiments, the liposome comprises one or more cationic lipids, one or more non-cationic lipids, and one or more PEG-modified lipids.

In some embodiments, the one or more cationic lipids comprise a cationic lipid selected from the group consisting of C12-200, MC3, DLinDMA, DLinkC2DMA, cKK-E12, ICE (Imidazole-based), HGT5000, HGT5001 (CCBene), OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLin-K-DMA, DLin-K-XTC2-DMA, HGT4003, and combinations thereof.

In some embodiments, the one or more non-cationic lipids comprise a non-cationic lipid selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)) and combinations thereof.

In some embodiments, the liposome further comprises one or more cholesterol-based lipids. For example, the one or more cholesterol-based lipids may be cholesterol and/or PEGylated cholesterol.

In some embodiments, the liposome further comprises a sphingomyelin. For example, the sphingomyelin may be a brain sphingomyelin.

In some embodiments, the mRNA comprises one or more modified nucleotides. For example, the one or more modified nucleotides may be pseudouridine, N-1-methyl-pseudouridine, 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine.

In some embodiments, the mRNA is unmodified.

It is to be understood that all embodiments as described above are applicable to all aspects of the present invention. Other features, objects, and advantages of the present invention are apparent in the detailed description, drawings, and claims that follow. It should be understood, however, that the detailed description, the drawings, and the claims, while indicating embodiments of the present invention, are given by way of illustration only, not limitation. Various changes and modifications within the scope of the invention will be apparent to those skilled in the art.

BRIEF DESCRIPTION OF THE DRAWING

The drawings are for illustration purposes only not for limitation.

DEFINITIONS

Figure 1:
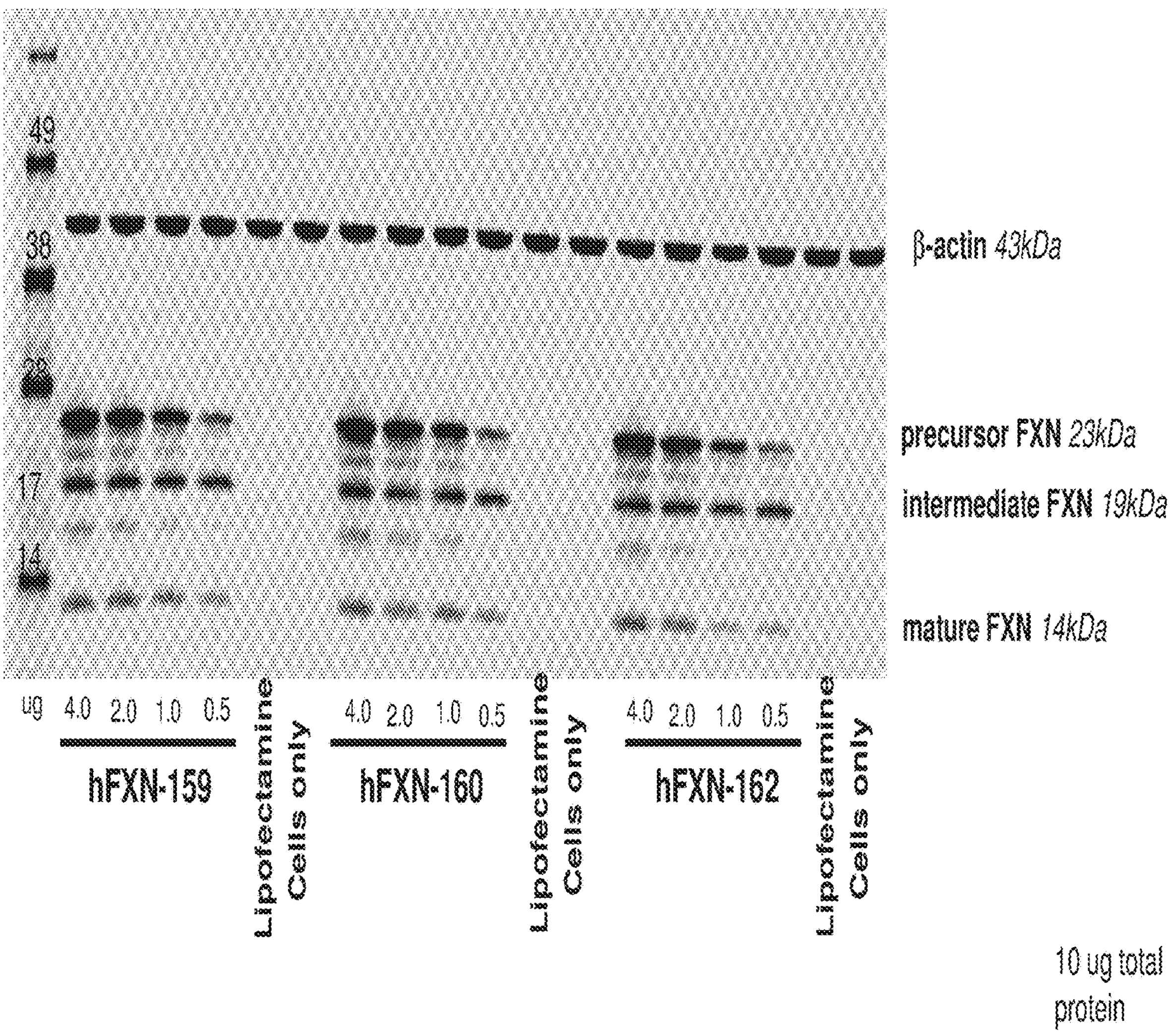
FIG. 1 depicts exemplary detection of human frataxin protein by Western blot after HEK cells were transfected with hFXN mRNA-loaded liposomes.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Encapsulation: As used herein, the term "encapsulation," or grammatical equivalent, refers to the process of incorporating an mRNA molecule into a nanoparticle.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated.

In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods of delivering compositions comprising mRNA encoding a frataxin protein and methods and compositions for treating Friedreich's ataxia (FRDA) based on mRNA therapy. In particular, the present invention provides methods of delivering a composition in vivo, the method comprising administering the composition to a subject, wherein the composition comprises an mRNA encoding a frataxin protein, and wherein the mRNA is encapsulated within a liposome. The present invention further provides methods of delivering a composition in vivo, the method comprising administering the composition to a subject, wherein the composition comprises an mRNA encoding a frataxin protein, and wherein the mRNA comprises a polynucleotide sequence at least 50%, 55%, 60%, 65%, 70%, 75%, 80%, 85%, 90%, 95%, 96%, 97%, 98%, 99%, or 100% identical to SEQ ID NO: 1, SEQ ID NO: 2, SEQ ID NO: 3, or SEQ ID NO: 4. In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains one or more of cationic lipid(s), non-cationic lipid(s), cholesterol-based lipid(s), PEG-modified lipid(s), and a sphingomyelin.

Various aspects of the invention are described in detail in the following sections. The use of sections is not meant to limit the invention. Each section can apply to any aspect of the invention. In this application, the use of "or" means "and/or" unless stated otherwise.

Friedreich's Ataxia (FRDA)

The present invention may be used to treat a subject who is suffering from or susceptible to FRDA (i.e., a subject in need of treatment). FRDA is a genetic disorder characterized by mutations in the gene for frataxin (FXN). Within cells, frataxin is found in energy-producing structures called mitochondria. Frataxin appears to help assemble clusters of iron and sulfur molecules that are critical for the function of many proteins, including those needed for energy production.

Symptoms of FRDA include: reduced frataxin levels (e.g., reduced functional frataxin levels), weight loss, early mortality (median age of death, 35 years), defects in motor coordination, defects in muscle strength, gait ataxia, and scoliosis. Characteristics of FRDA pathology include: degeneration of the dorsal root ganglia (DRG), retinal cell degeneration, increased ferritin levels, increased ferroportin levels, iron accumulation, cardiac fibrosis, cardiomyopathy, aconitase activity, activation of apoptosis and autophagy and reduced myelin sheath thickness.

Frataxin (FXN)

In some embodiments, the present invention provides methods and compositions for delivering mRNA encoding FXN to a subject for the treatment of FRDA. A suitable FXN mRNA encodes any full length, fragment or portion of a frataxin protein which can be substituted for naturally-occurring frataxin protein activity and/or reduce the intensity, severity, and/or frequency of one or more symptoms associated with FRDA.

In some embodiments, a suitable mRNA sequence is a human mRNA sequence (hFXN) encoding a human frataxin protein. In some embodiments, a suitable mRNA sequence is a codon-optimized mRNA sequence encoding a human frataxin protein.

```
Codon-optimized human FXN mRNA coding
sequence #1
                                          (SEQ ID NO: 1)
AUGUGGACCCUGGGUCGGAGAGCUGUGGCCGGUCUGCUGGCUUCCCCCUC

ACCGGCACAAGCGCAGACCCUGACUAGAGUGCCUAGGCCCGCUGAACUCG

CACCACUGUGCGGCAGACGGGGACUCCGGACUGACAUCGAUGCCACCUGU

ACCCCGCGAAGGGCAUCUAGCAAUCAGCGCGGACUGAACCAGAUCUGGAA

CGUGAAGAAGCAGUCCGUGUACCUGAUGAAUCUGCGCAAAUCCGGCACUC

UCGGACACCCGGGAUCGCUGGAUGAGACUACUUACGAGCGCUUGGCCGAA

GAAACCCUGGAUUCGCUGGCCGAGUUUUUCGAGGACCUGGCCGACAAGCC

CUACACGUUCGAGGACUACGACGUGUCCUUCGGAUCGGGCGUGCUGACCG

UGAAGCUCGGCGGGGAUUUGGGGACCUACGUGAUCAACAAGCAGACACCG

AACAAGCAAAUUUGGCUCUCCUCCCCUUCCUCCGGACCUAAGCGCUACGA

CUGGACCGGGAAGAACUGGGUCUACUCCCAUGACGGCGUCAGCCUUCACG

AACUGCUGGCCGCCGAACUGACUAAGGCCCUCAAAACUAAGCUGGACCUG

UCGAGCCUUGCCUAUUCCGGAAAGGACGCCUGA

Codon-optimized human FXN mRNA coding
sequence #2
                                          (SEQ ID NO: 2)
AUGUGGACCCUGGGACGCAGAGCCGUGGCUGGCCUUCUGGCCUCCCCAAG

CCCUGCCCAAGCCCAGACCUUGACUAGAGUGCCUAGACCGGCCGAACUCG

CUCCCCUGUGCGGACGGAGGGGACUCAGGACUGACAUCGACGCAACAUGC

ACUCCAAGACGCGCCUCCAGCAACCAGCGGGGCCUCAACCAGAUUUGGAA

CGUGAAAAAGCAGUCCGUCUAUCUGAUGAACCUCCGCAAGUCCGGCACCU

UGGGGCAUCCCGGGUCACUGGAUGAAACCACCUACGAACGGCUGGCCGAA

GAGACUCUCGACUCCCUGGCCGAGUUCUUCGAGGACCUGGCGGAUAAGCC
```

-continued

GUACACUUUCGAGGACUACGAUGUCUCUUUCGGAUCCGGCGUGCUGACCG

UGAAGCUCGGUGGCGACCUCGGAACUUACGUGAUCAACAAGCAAACGCCC

AACAAGCAGAUCUGGCUGUCCUCGCCGUCAUCGGGACCUAAGCGCUACGA

UUGGACCGGGAAGAAUUGGGUGUACUCGCACGACGGUGUCAGCCUGCACG

AGCUGCUUGCGGCGGAACUGACCAAGGCACUCAAGACCAAACUGGACCUG

UCCAGCCUGGCCUACUCCGGAAAGGACGCCUAG

Codon-optimized human FXN mRNA coding sequence #3

(SEQ ID NO: 3)

AUGUGGACUCUGGGCCGGAGAGCUGUGGCAGGCCUUCUCGCCUCGCCAUC

CCCUGCCCAAGCGCAGACCCUGACUAGGGUCCCUAGGCCUGCCGAGUUGG

CACCGUUGUGCGGUCGGAGAGGACUGCGCACCGACAUCGAUGCCACCUGU

ACUCCUCGGAGAGCCUCGUCCAACCAGCGGGGCCUGAACCAGAUCUGGAA

CGUGAAGAAACAGUCCGUCUACCUGAUGAACCUCCGCAAGUCGGGAACCC

UGGGACAUCCGGGUUCCCUGGAUGAGACUACGUACGAACGGCUGGCGGAA

GAAACCCUGGACUCCCUGGCGGAGUUCUUCGAGGACCUGGCUGACAAGCC

CUACACUUUUGAGGACUACGACGUGUCAUUCGGAAGCGGAGUGUUGACAG

UGAAGCUGGGGGGCGAUCUGGGAACCUACGUGAUCAACAAGCAGACCCCG

AACAAGCAAAUUUGGCUGUCCUCACCCUCCUCCGGACCUAAACGCUACGA

CUGGACCGGGAAGAACUGGGUGUAUAGCCACGACGGUGUCAGCCUUCACG

AACUGCUUGCGGCCGAACUGACCAAGGCCCUCAAGACCAAGCUCGAUCUG

UCUAGCCUCGCCUACUCCGGAAAGGACGCCUGA

Codon-optimized human FXN mRNA coding sequence #4

(SEQ ID NO: 4)

AUGUGGACCUUGGGACGGAGAGCCGUGGCUGGACUGUUGGCCUCUCCUUC

CCCGGCACAAGCCCAAACUCUGACCCGGGUCCCUAGACCGGCAGAGCUGG

CUCCCCUGUGUGGUCGGCGGGGACUGAGAACUGAUAUUGACGCCACAUGC

ACUCCUAGGCGCGCGAGCUCCAAUCAGCGCGGCCUGAACCAGAUCUGGAA

CGUGAAGAAGCAGUCCGUCUACUUGAUGAACCUCCGCAAGUCCGGCACUC

UGGGCCAUCCGGGAUCCCUCGACGAGACUACCUACGAGCGGCUGGCGGAA

GAAACCCUGGAUUCCCUGGCCGAAUUCUUCGAGGACCUGGCCGACAAGCC

CUACACCUUUGAGGACUACGACGUGUCCUUCGGAUCGGGAGUGCUGACCG

UGAAGCUCGGCGGAGAUCUCGGGACUUAUGUGAUCAACAAGCAGACGCCG

AACAAGCAGAUCUGGCUUAGCUCACCCUCGAGCGGACCAAAGCGCUACGA

CUGGACCGGCAAAAACUGGGUGUACUCCCACGAUGGUGUCAGCCUUCACG

AACUGCUGGCCGCGGAACUGACCAAGGCCCUUAAGACCAAGCUCGACCUC

UCAUCCCUGGCCUACUCCGGGAAAGACGCGUGA

Human FXN protein sequence (SEQ ID NO: 5)

MWTLGRRAVAGLLASPSPAQAQTLTRVPRPAELAPLCGRRGLRTDIDATC

TPRRASSNQRGLNQIWNVKKQSVYLMNLRKSGTLGHPGSLDETTYERLAE

ETLDSLAEFFEDLADKPYTFEDYDVSFGSGVLTVKLGGDLGTYVINKQTP

NKQIWLSSPSSGPKRYDWTGKNWVYSHDGVSLHELLAAELTKALKTKLDL

SSLAYSGKDA

Exemplary Codon-Optimized Frataxin (FXN) mRNAs

Construct Design

X-SEQ ID NO: 1-Y

X-SEQ ID NO: 2-Y

X-SEQ ID NO: 3-Y

X-SEQ ID NO: 4-Y

5' and 3' UTR Sequences

X (5' UTR Sequence) =

(SEQ ID NO: 6)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence) =

(SEQ ID NO: 7)

CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU

OR (SEQ ID NO: 8)

GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU

In one embodiment, a codon-optimized human FXN mRNA sequence includes SEQ ID NO: 1.

In one embodiment, a full-length codon-optimized human FXN mRNA sequence is:

(SEQ ID NO: 9)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGUGGACCC

UGGGUCGGAGAGCUGUGGCCGGUCUGCUGGCUUCCCCCUCACCGGCACAA

GCGCAGACCCUGACUAGAGUGCCUAGGCCCGCUGAACUCGCACCACUGUG

CGGCAGACGGGGACUCCGGACUGACAUCGAUGCCACCUGUACCCCGCGAA

GGGCAUCUAGCAAUCAGCGCGGACUGAACCAGAUCUGGAACGUGAAGAAG

CAGUCCGUGUACCUGAUGAAUCUGCGCAAAUCCGGCACUCUCGGACACCC

GGGAUCGCUGGAUGAGACUACUUACGAGCGCUUGGCCGAAGAAACCCUGG

AUUCGCUGGCCGAGUUUUUCGAGGACCUGGCCGACAAGCCCUACACGUUC

GAGGACUACGACGUGUCCUUCGGAUCGGGCGUGCUGACCGUGAAGCUCGG

CGGGGAUUUGGGGACCUACGUGAUCAACAAGCAGACACCGAACAAGCAAA

UUUGGCUCUCCUCCCCUUCCUCCGGACCUAAGCGCUACGACUGGACCGGG

AAGAACUGGGUCUACUCCCAUGACGGCGUCAGCCUUCACGAACUGCUGGC

CGCCGAACUGACUAAGGCCCUCAAAACUAAGCUGGACCUGUCGAGCCUUG

CCUAUUCCGGAAAGGACGCCUGACGGGUGGCAUCCCUGUGACCCCUCCCC

-continued

AGUGCCUCUCCUGGCCCUGGAAGUUGCCACUCCAGUGCCCACCAGCCUUG

UCCUAAUAAAAUUAAGUUGCAUCAAGCU

In one embodiment, another full-length codon-optimized human FXN mRNA sequence is:

(SEQ ID NO: 10)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGUGGACCC

UGGGUCGGAGAGCUGUGGCCGGUCUGCUGGCUUCCCCCUCACCGGCACAA

GCGCAGACCCUGACUAGAGUGCCUAGGCCCGCUGAACUCGCACCACUGUG

CGGCAGACGGGGACUCCGGACUGACAUCGAUGCCACCUGUACCCCGCGAA

GGGCAUCUAGCAAUCAGCGCGGACUGAACCAGAUCUGGAACGUGAAGAAG

CAGUCCGUGUACCUGAUGAAUCUGCGCAAAUCCGGCACUCUCGGACACCC

GGGAUCGCUGGAUGAGACUACUUACGAGCGCUUGGCCGAAGAAACCCUGG

AUUCGCUGGCCGAGUUUUUCGAGGACCUGGCCGACAAGCCCUACACGUUC

GAGGACUACGACGUGUCCUUCGGAUCGGGCGUGCUGACCGUGAAGCUCGG

CGGGGAUUUGGGGACCUACGUGAUCAACAAGCAGACACCGAACAAGCAAA

UUUGGCUCUCCUCCCCUUCCUCCGGACCUAAGCGCUACGACUGGACCGGG

AAGAACUGGGUCUACUCCCAUGACGGCGUCAGCCUUCACGAACUGCUGGC

CGCCGAACUGACUAAGGCCCUCAAAACUAAGCUGGACCUGUCGAGCCUUG

CCUAUUCCGGAAAGGACGCCUGAGGGUGGCAUCCCUGUGACCCCUCCCCA

GUGCCUCUCCUGGCCCUGGAAGUUGCCACUCCAGUGCCCACCAGCCUUGU

CCUAAUAAAAUUAAGUUGCAUCAAAGCU

In one embodiment, a codon-optimized human FXN mRNA sequence includes SEQ ID NO: 2.

In one embodiment, a full-length codon-optimized human FXN mRNA sequence is:

(SEQ ID NO: 11)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGUGGACCC

UGGGACGCAGAGCCGUGGCUGGCCUUCUGGCCUCCCCAAGCCCUGCCCAA

GCCCAGACCUUGACUAGAGUGCCUAGACCGGCCGAACUCGCUCCCCUGUG

CGGACGGAGGGGACUCAGGACUGACAUCGACGCAACAUGCACUCCAAGAC

GCGCCUCCAGCAACCAGCGGGGCCUCAACCAGAUUUGGAACGUGAAAAAG

CAGUCCGUCUAUCUGAUGAACCUCCGCAAGUCCGGCACCUUGGGGCAUCC

CGGGUCACUGGAUGAAACCACCUACGAACGGCUGGCCGAAGAGACUCUCG

ACUCCCUGGCCGAGUUCUUCGAGGACCUGGCGGAUAAGCCGUACACUUUC

GAGGACUACGAUGUCUCUUUCGGAUCCGGCGUGCUGACCGUGAAGCUCGG

UGGCGACCUCGGAACUUACGUGAUCAACAAGCAAACGCCCAACAAGCAGA

UCUGGCUGUCCUCGCCGUCAUCGGGACCUAAGCGCUACGAUUGGACCGGG

AAGAAUUGGGUGUACUCGCACGACGGUGUCAGCCUGCACGAGCUGCUUGC

GGCGGAACUGACCAAGGCACUCAAGACCAAACUGGACCUGUCCAGCCUGG

CCUACUCCGGAAAGGACGCCUAGCGGGUGGCAUCCCUGUGACCCCUCCCC

AGUGCCUCUCCUGGCCCUGGAAGUUGCCACUCCAGUGCCCACCAGCCUUG

UCCUAAUAAAAUUAAGUUGCAUCAAGCU

In one embodiment, another full-length codon-optimized human FXN mRNA sequence is:

(SEQ ID NO: 12)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGUGGACCC

UGGGACGCAGAGCCGUGGCUGGCCUUCUGGCCUCCCCAAGCCCUGCCCAA

GCCCAGACCUUGACUAGAGUGCCUAGACCGGCCGAACUCGCUCCCCUGUG

CGGACGGAGGGGACUCAGGACUGACAUCGACGCAACAUGCACUCCAAGAC

GCGCCUCCAGCAACCAGCGGGGCCUCAACCAGAUUUGGAACGUGAAAAAG

CAGUCCGUCUAUCUGAUGAACCUCCGCAAGUCCGGCACCUUGGGGCAUCC

CGGGUCACUGGAUGAAACCACCUACGAACGGCUGGCCGAAGAGACUCUCG

ACUCCCUGGCCGAGUUCUUCGAGGACCUGGCGGAUAAGCCGUACACUUUC

GAGGACUACGAUGUCUCUUUCGGAUCCGGCGUGCUGACCGUGAAGCUCGG

UGGCGACCUCGGAACUUACGUGAUCAACAAGCAAACGCCCAACAAGCAGA

UCUGGCUGUCCUCGCCGUCAUCGGGACCUAAGCGCUACGAUUGGACCGGG

AAGAAUUGGGUGUACUCGCACGACGGUGUCAGCCUGCACGAGCUGCUUGC

GGCGGAACUGACCAAGGCACUCAAGACCAAACUGGACCUGUCCAGCCUGG

CCUACUCCGGAAAGGACGCCUAGGGGUGGCAUCCCUGUGACCCCUCCCCA

GUGCCUCUCCUGGCCCUGGAAGUUGCCACUCCAGUGCCCACCAGCCUUGU

CCUAAUAAAAUUAAGUUGCAUCAAAGCU

In one embodiment, a codon-optimized human FXN mRNA sequence includes SEQ ID NO: 3.

In one embodiment, a full-length codon-optimized human FXN mRNA sequence is:

(SEQ ID NO: 13)

GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACGAUGUGGACUC

UGGGCCGGAGAGCUGUGGCAGGCCUUCUCGCCUCGCCAUCCCCUGCCCAA

GCGCAGACCCUGACUAGGGUCCCUAGGCCUGCCGAGUUGGCACCGUUGUG

CGGUCGGAGAGGACUGCGCACCGACAUCGAUGCCACCUGUACUCCUCGGA

GAGCCUCGUCCAACCAGCGGGGCCUGAACCAGAUCUGGAACGUGAAGAAA

CAGUCCGUCUACCUGAUGAACCUCCGCAAGUCGGGAACCCUGGGACAUCC

GGGUUCCCUGGAUGAGACUACGUACGAACGGCUGGCGGAAGAAACCCUGG

ACUCCCUGGCGGAGUUCUUCGAGGACCUGGCUGACAAGCCCUACACUUUU

GAGGACUACGACGUGUCAUUCGGAAGCGGAGUGUUGACAGUGAAGCUGGG

-continued

```
GGGCGAUCUGGGAACCUACGUGAUCAACAAGCAGACCCCGAACAAGCAAA
UUUGGCUGUCCUCACCCUCCUCCGGACCUAAACGCUACGACUGGACCGGG
AAGAACUGGGUGUAUAGCCACGACGGUGUCAGCCUUCACGAACUGCUUGC
GGCCGAACUGACCAAGGCCCUCAAGACCAAGCUCGAUCUGUCUAGCCUCG
CCUACUCCGGAAAGGACGCCUGACGGGUGGCAUCCCUGUGACCCCUCCCC
AGUGCCUCUCCUGGCCCUGGAAGUUGCCACUCCAGUGCCCACCAGCCUUG
UCCUAAUAAAAUUAAGUUGCAUCAAGCU
```

In one embodiment, another full-length codon-optimized human FXN mRNA sequence is:

```
                                     (SEQ ID NO: 14)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACGAUGUGGACUC
UGGGCCGGAGAGCUGUGGCAGGCCUUCUCGCCUCGCCAUCCCCUGCCCAA
GCGCAGACCCUGACUAGGGUCCCUAGGCCUGCCGAGUUGGCACCGUUGUG
CGGUCGGAGAGGACUGCGCACCGACAUCGAUGCCACCUGUACUCCUCGGA
GAGCCUCGUCCAACCAGCGGGGCCUGAACCAGAUCUGGAACGUGAAGAAA
CAGUCCGUCUACCUGAUGAACCUCCGCAAGUCGGGAACCCUGGGACAUCC
GGGUUCCCUGGAUGAGACUACGUACGAACGGCUGGCGGAAGAAACCCUGG
ACUCCCUGGCGGAGUUCUUCGAGGACCUGGCUGACAAGCCCUACACUUUU
GAGGACUACGACGUGUCAUUCGGAAGCGGAGUGUUGACAGUGAAGCUGGG
GGGCGAUCUGGGAACCUACGUGAUCAACAAGCAGACCCCGAACAAGCAAA
UUUGGCUGUCCUCACCCUCCUCCGGACCUAAACGCUACGACUGGACCGGG
AAGAACUGGGUGUAUAGCCACGACGGUGUCAGCCUUCACGAACUGCUUGC
GGCCGAACUGACCAAGGCCCUCAAGACCAAGCUCGAUCUGUCUAGCCUCG
CCUACUCCGGAAAGGACGCCUGAGGGUGGCAUCCCUGUGACCCCUCCCCA
GUGCCUCUCCUGGCCCUGGAAGUUGCCACUCCAGUGCCCACCAGCCUUGU
CCUAAUAAAAUUAAGUUGCAUCAAAGCU
```

In one embodiment, a codon-optimized human FXN mRNA sequence includes SEQ ID NO: 4.

In one embodiment, a full-length codon-optimized human FXN mRNA sequence is:

```
                                     (SEQ ID NO: 15)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACGAUGUGGACCU
UGGGACGGAGAGCCGUGGCUGGACUGUUGGCCUCUCCUUCCCCGGCACAA
GCCCAAACUCUGACCCGGGUCCCUAGACCGGCAGAGCUGGCUCCCCUGUG
UGGUCGGCGGGGACUGAGAACUGAUAUUGACGCCACAUGCACUCCUAGGC
GCGCGAGCUCCAAUCAGCGCGGCCUGAACCAGAUCUGGAACGUGAAGAAG
CAGUCCGUCUACUUGAUGAACCUCCGCAAGUCCGGCACUCUGGGCCAUCC
GGGAUCCCUCGACGAGACUACCUACGAGCGGCUGGCGGAAGAAACCCUGG
```

-continued

```
AUUCCCUGGCCGAAUUCUUCGAGGACCUGGCCGACAAGCCCUACACCUUU
GAGGACUACGACGUGUCCUUCGGAUCGGGAGUGCUGACCGUGAAGCUCGG
CGGAGAUCUCGGGACUUAUGUGAUCAACAAGCAGACGCCGAACAAGCAGA
UCUGGCUUAGCUCACCCUCGAGCGGACCAAAGCGCUACGACUGGACCGGC
AAAAACUGGGUGUACUCCCACGAUGGUGUCAGCCUUCACGAACUGCUGGC
CGCGGAACUGACCAAGGCCCUUAAGACCAAGCUCGACCUCUCAUCCCUGG
CCUACUCCGGGAAAGACGCGUGACGGGUGGCAUCCCUGUGACCCCUCCCC
AGUGCCUCUCCUGGCCCUGGAAGUUGCCACUCCAGUGCCCACCAGCCUUG
UCCUAAUAAAAUUAAGUUGCAUCAAGCU
```

In one embodiment, another full-length codon-optimized human FXN mRNA sequence is:

```
                                     (SEQ ID NO: 16)
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACGAUGUGGACCU
UGGGACGGAGAGCCGUGGCUGGACUGUUGGCCUCUCCUUCCCCGGCACAA
GCCCAAACUCUGACCCGGGUCCCUAGACCGGCAGAGCUGGCUCCCCUGUG
UGGUCGGCGGGGACUGAGAACUGAUAUUGACGCCACAUGCACUCCUAGGC
GCGCGAGCUCCAAUCAGCGCGGCCUGAACCAGAUCUGGAACGUGAAGAAG
CAGUCCGUCUACUUGAUGAACCUCCGCAAGUCCGGCACUCUGGGCCAUCC
GGGAUCCCUCGACGAGACUACCUACGAGCGGCUGGCGGAAGAAACCCUGG
AUUCCCUGGCCGAAUUCUUCGAGGACCUGGCCGACAAGCCCUACACCUUU
GAGGACUACGACGUGUCCUUCGGAUCGGGAGUGCUGACCGUGAAGCUCGG
CGGAGAUCUCGGGACUUAUGUGAUCAACAAGCAGACGCCGAACAAGCAGA
UCUGGCUUAGCUCACCCUCGAGCGGACCAAAGCGCUACGACUGGACCGGC
AAAAACUGGGUGUACUCCCACGAUGGUGUCAGCCUUCACGAACUGCUGGC
CGCGGAACUGACCAAGGCCCUUAAGACCAAGCUCGACCUCUCAUCCCUGG
CCUACUCCGGGAAAGACGCGUGAGGGUGGCAUCCCUGUGACCCCUCCCCA
GUGCCUCUCCUGGCCCUGGAAGUUGCCACUCCAGUGCCCACCAGCCUUGU
CCUAAUAAAAUUAAGUUGCAUCAAAGCU
```

SEQ ID NOs: 9-16 include 5' and 3' untranslated regions framing a codon-optimized hFXN-encoding mRNA.

In some embodiments, a suitable mRNA sequence encodes a homolog or an analog of human frataxin. For example, a homolog or an analog of human frataxin may be a modified human frataxin protein containing one or more amino acid substitutions, deletions, and/or insertions as compared to a wild-type or naturally-occurring human frataxin while retaining substantial human frataxin activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 5. In some embodiments, an mRNA suitable for the present invention encodes a protein substantially identical to human frataxin. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 5. In some embodiments, an mRNA suitable for the present invention encodes a fragment or a portion of human frataxin protein. In some embodiments, an mRNA suitable for the present invention encodes a fragment or a portion of human frataxin protein, wherein the fragment or portion of the protein still maintains frataxin activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 2, SEQ ID NO: 3, SEQ ID NO: 4, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. In some embodiments, an mRNA suitable for the present invention comprises a nucleotide sequence identical to SEQ ID NO: 1. In some embodiments, an mRNA suitable for the present invention comprises a nucleotide sequence identical to SEQ ID NO: 2. In some embodiments, an mRNA suitable for the present invention comprises a nucleotide sequence identical to SEQ ID NO: 3. In some embodiments, an mRNA suitable for the present invention comprises a nucleotide sequence identical to SEQ ID NO: 4.

In some embodiments, a suitable mRNA encodes a fusion protein comprising a full length, fragment or portion of a human frataxin protein fused to another protein (e.g., an N or C terminal fusion). In some embodiments, the protein fused to the mRNA encoding a full length, fragment or portion of a human frataxin protein encodes a signal or a cellular targeting sequence.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., mRNAs encoding frataxin) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, mRNAs (e.g., mRNAs encoding frataxin) include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with $—OCH_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}$GpppG), trimethylated cap analog (e.g., $m^{2,2,7}$GpppG), dimethylated symmetrical cap analogs (e.g., $m^7$Gpppm$^7$G), or anti reverse cap analogs (e.g., ARCA; $m^{7,2'Ome}$GpppG, $m^{72'd}$GpppG, $m^{7,3'Ome}$GpppG, $m^{7,3'd}$GpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("$m^7$G") linked via a triphosphate bridge to the 5'-end of the first transcribed nucleotide, resulting in $m^7$G (5')ppp(5')N, where N is any nucleoside. A preferred embodiment of a $m^7$G cap utilized in embodiments of the invention is $m^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of $m^7$G cap analogs are known in the art, many of which are commercially available. These include the $m^7$GpppG described above, as well as the ARCA 3'-$OCH_3$ and 2'-$OCH_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, each of which are incorporated by reference herein for all purposes.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Regions

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Modified mRNA

In some embodiments, mRNA according to the present invention may be synthesized as unmodified or modified mRNA. In some embodiments, unmodified mRNA comprises a 5' cap, 5' and 3' UTRs and a polyA tail, but no modifications to the nucleotides of the mRNA. In some embodiments, modifications of mRNA can include modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thiouracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of each of which are incorporated by reference for all purposes.

In some embodiments, mRNAs (e.g., mRNAs encoding frataxin) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., mRNAs encoding frataxin) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), azidotriphosphates (2'-azido-2'-deoxycytidine 5'-triphosphate, 2'-azido-2'-deoxyuridine 5'-triphosphate) or 4'-thioribonucleotides (described in U.S. patent application US 2016/0031928, filed Sep. 14, 2015, incorporated herein by reference for all purposes).

In some embodiments, mRNAs (e.g., mRNAs encoding frataxin) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Delivery Vehicles

According to the present invention, mRNA encoding a frataxin protein (e.g., a full length, fragment, or portion of a frataxin protein) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, mRNAs encoding a frataxin protein may be delivered via a single delivery vehicle. In some embodiments, mRNAs encoding a frataxin protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A delivery vehicle comprising FXN mRNA may be administered and dosed in accordance with current medical practice, taking into account the clinical condition of the subject, the site and method of administration (e.g., local and systemic, including intrathecal and via injection), the scheduling of administration, the subject's age, sex, body weight, and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein production.

In some embodiments, delivery vehicles are formulated such that they are suitable for extended-release of the mRNA contained therein. Such extended-release compositions may be conveniently administered to a subject at extended dosing intervals.

Liposomal Delivery Vehicles

In some embodiments, a suitable delivery vehicle is a liposomal delivery vehicle, e.g., a liposome. As used herein, liposomal delivery vehicles, e.g., liposomes, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids, one or more PEG-modified lipids, and one or more sphingolipids. In some embodiments, a liposome comprises one or more cationic lipids, one or more non-cationic lipids, one or more cholesterol-based lipids and one or more PEG-modified lipids. In some embodiments, a liposome comprises one or more cationic lipids, one or more non-cationic lipids, and one or more PEG-modified lipids. In some embodiments, a liposome comprises no more than three distinct lipid components. In some embodiments, one distinct lipid component is a sterol-based cationic lipid.

Cationic Lipids

As used herein, the term "cationic lipids" refers to any of a number of lipid and lipidoid species that have a net positive charge at a selected pH, such as at physiological pH. Several cationic lipids have been described in the literature, many of which are commercially available.

Suitable cationic lipids for use in the compositions and methods of the invention include the cationic lipids as described in International Patent Publication WO 2010/144740, which is incorporated herein by reference for all purposes. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

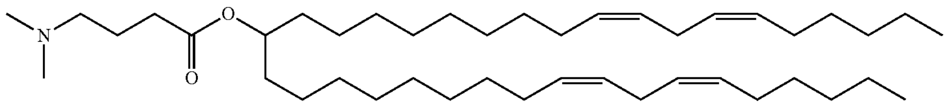 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference for all purposes. In some embodiments, the compositions and methods of the present invention include a cationic lipid of one of the following formulas:

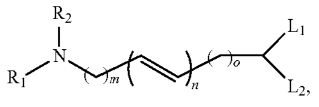

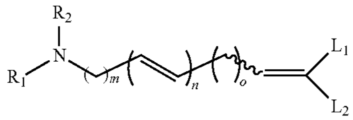

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

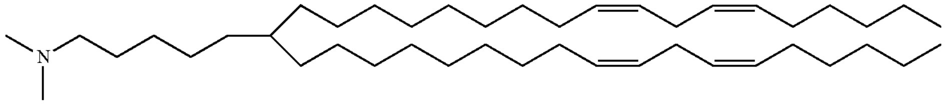

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001", also called "CCBene", which can be used interchangeably), having a compound structure of:

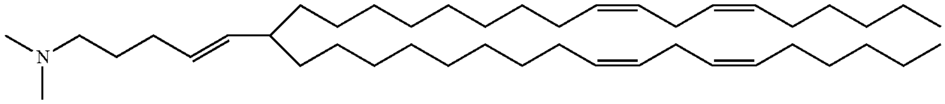

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

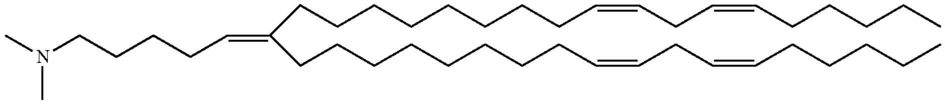

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference for all purposes. In certain embodiments, the compositions and methods of the present invention include a cationic lipid having a compound structure of:

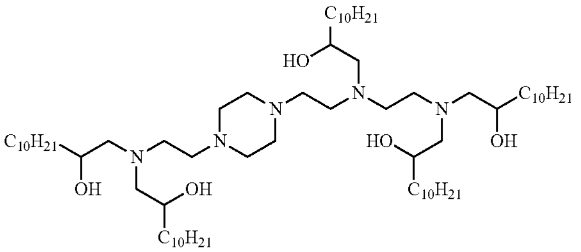

and pharmaceutically acceptable salts thereof.

Other suitable cationic lipids for use in the compositions and methods of the invention include the cationic lipids as described in International Patent Publication WO 2016/118725, which is incorporated herein by reference for all purposes. In certain embodiments, the compositions and methods of the present invention include a cationic lipid having a compound structure of:

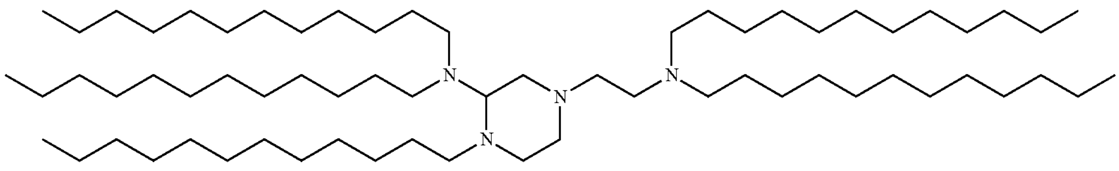 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference for all purposes. In certain embodiments, the compositions and methods of the present invention include a cationic lipid having a compound structure of:

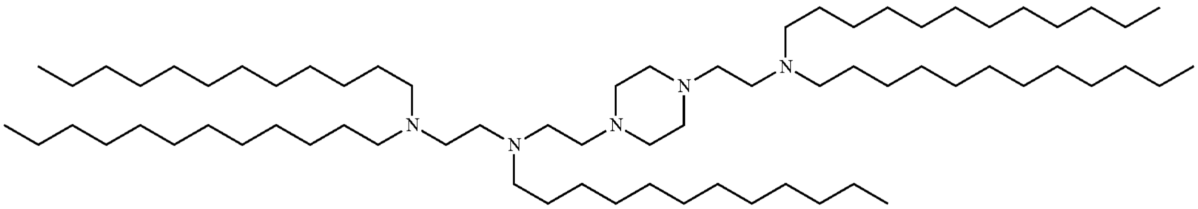 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference for all purposes. In some embodiments, the compositions and methods of the present invention include a cationic lipid of the following formula:

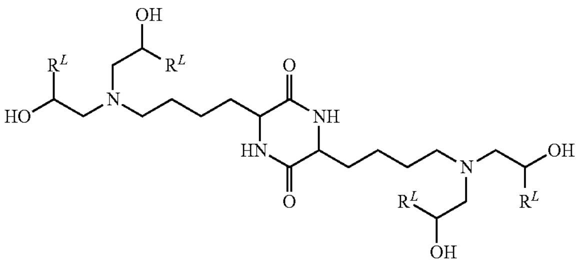

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

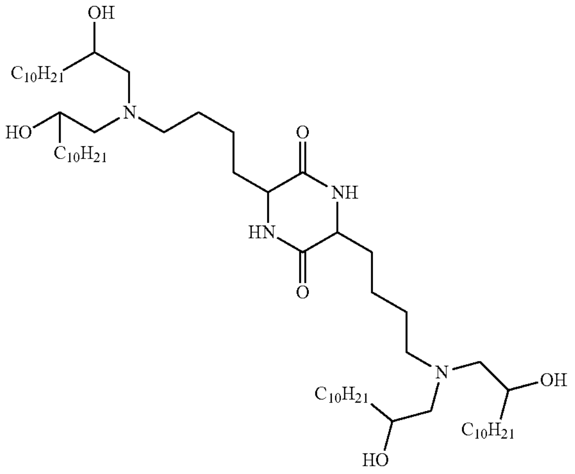

and pharmaceutically acceptable salts thereof. In certain embodiments, the compositions and methods of the present invention include a cationic lipid having a compound structure of:

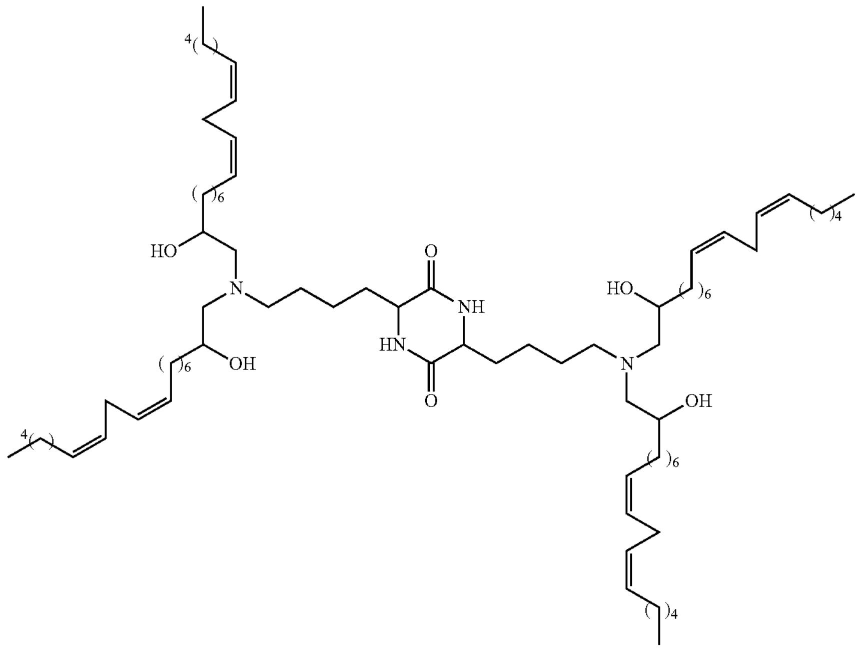

and pharmaceutically acceptable salts thereof. In certain embodiments, the compositions and methods of the present invention include a cationic lipid having a compound structure of:

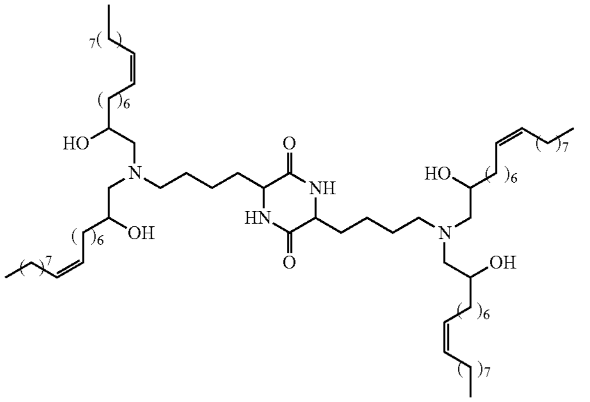

and pharmaceutically acceptable salts thereof. In certain embodiments, the compositions and methods of the present invention include a cationic lipid having a compound structure of:

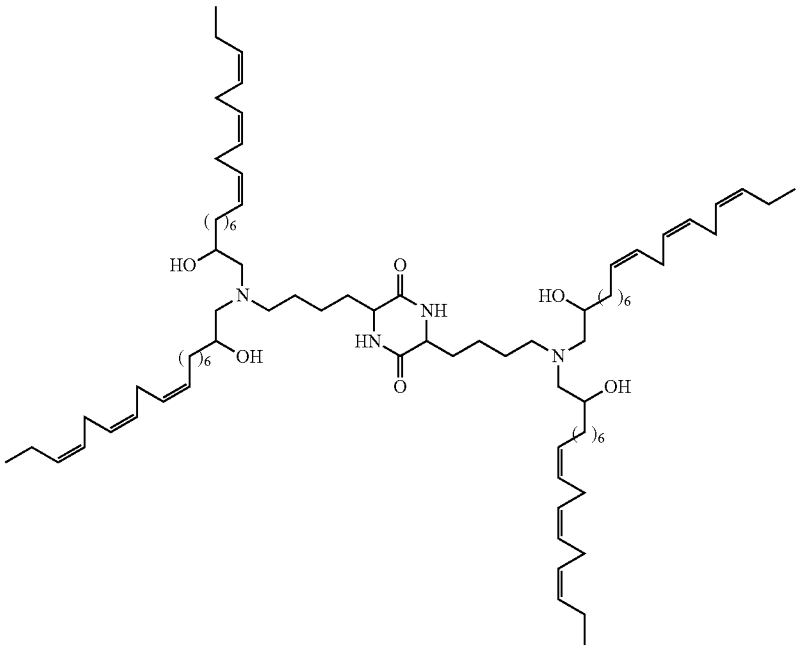

and pharmaceutically acceptable salts thereof.

Other suitable cationic lipids for use in the compositions and methods of the invention include the cationic lipids as described in International Patent Publication WO 2015/184256, which is incorporated herein by reference for all purposes. In some embodiments, the compositions and methods of the present invention include a cationic lipid of the following formula:

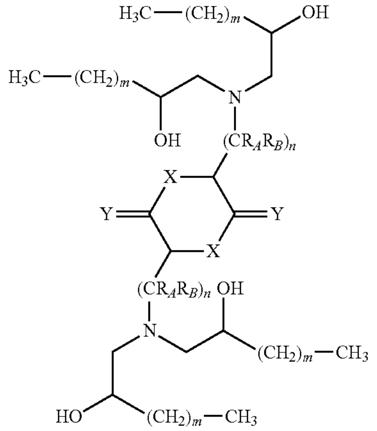

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, “Target 23”, having a compound structure of:

(Target 23)

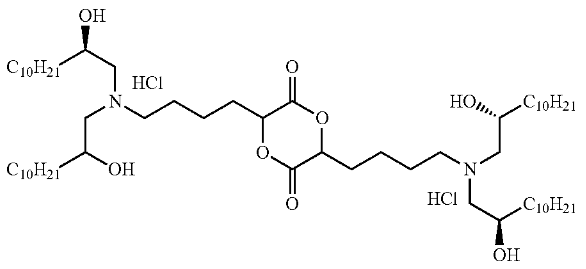

and pharmaceutically acceptable salts thereof.

Other suitable cationic lipids for use in the compositions and methods of the invention include the cationic lipids as described in International Patent Publication WO 2016/004202, which is incorporated herein by reference for all purposes. In some embodiments, the compositions and methods of the present invention include a cationic lipid having the compound structure:

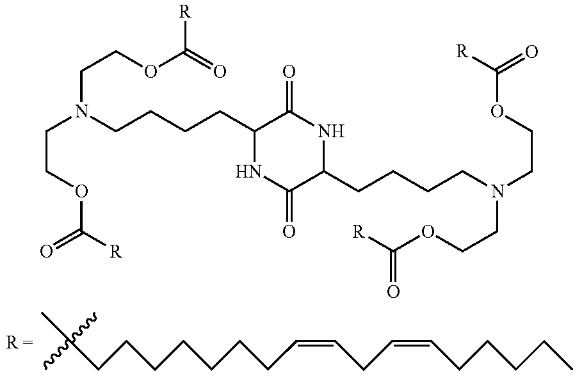

or a pharmaceutically acceptable salt thereof. In some embodiments, the compositions and methods of the present invention include a cationic lipid having the compound structure:

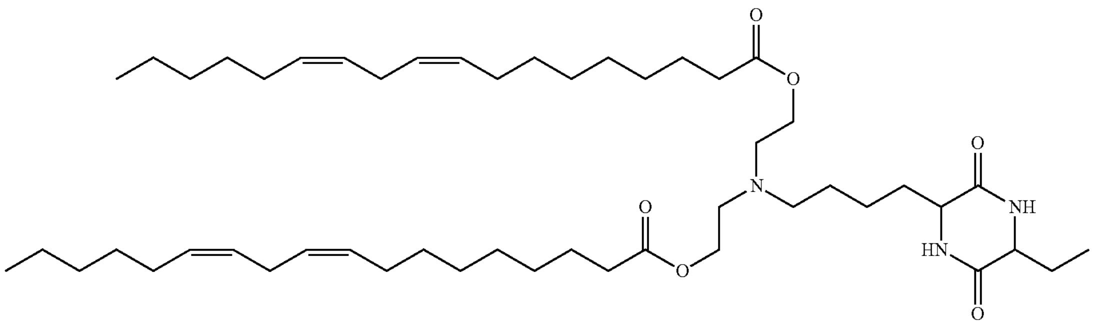 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

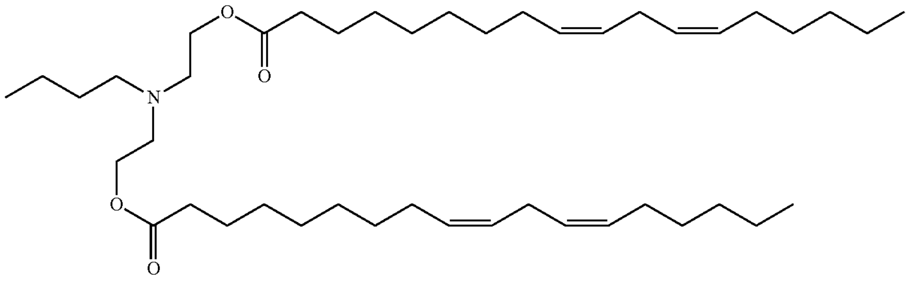 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference for all purposes. In certain embodiments, the cationic lipids of the compositions and methods of the present invention include a cationic lipid having a compound structure of:

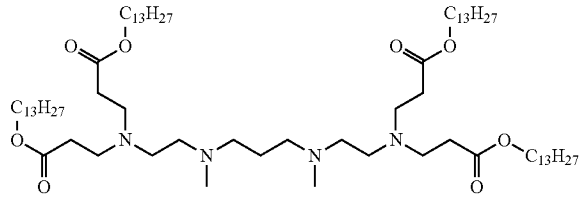

and pharmaceutically acceptable salts thereof.

Other suitable cationic lipids for use in the compositions and methods of the invention include the cationic lipids as described in International Patent Publication WO 2015/199952, which is incorporated herein by reference for all purposes. In some embodiments, the compositions and methods of the present invention include a cationic lipid having the compound structure:

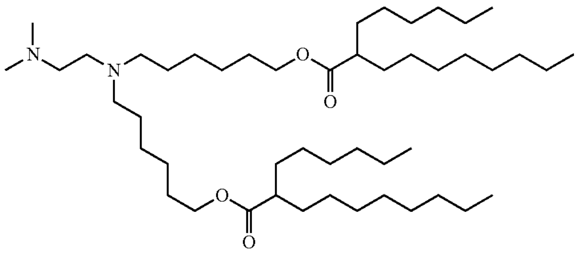 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

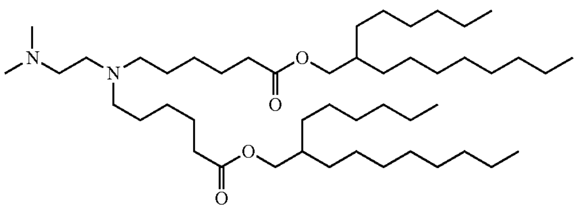

and pharmaceutically acceptable salts thereof. In some embodiments, the compositions and methods of the present invention include a cationic lipid having the compound structure:

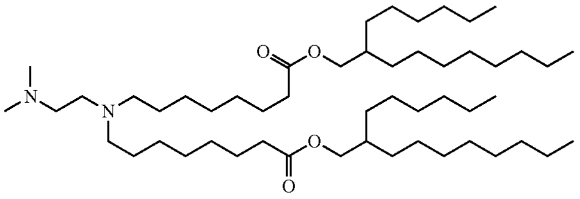

and pharmaceutically acceptable salts thereof. In some embodiments, the compositions and methods of the present invention include a cationic lipid having the compound structure:

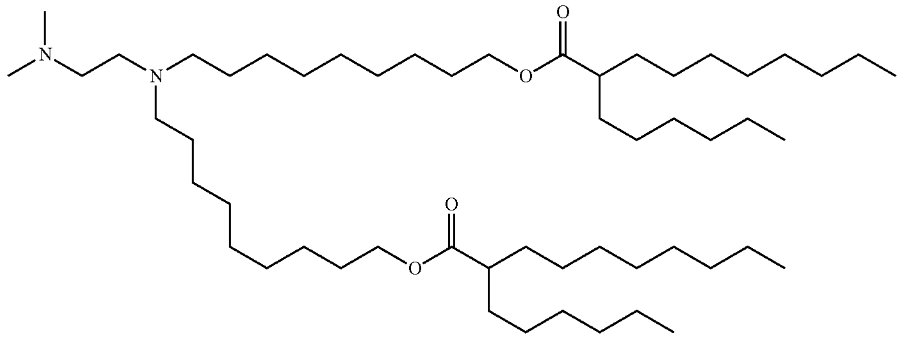 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

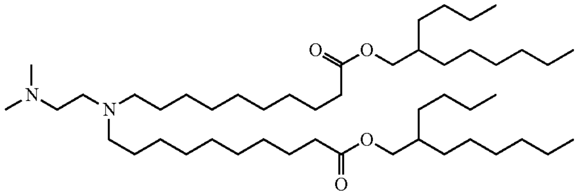 [SMILES: CCCCCCC(CCCC)COC(=O)CCCCCCCCCN(CCCCCCCCCC(=O)OCC(CCCC)CCCCCC)CCN(C)C]

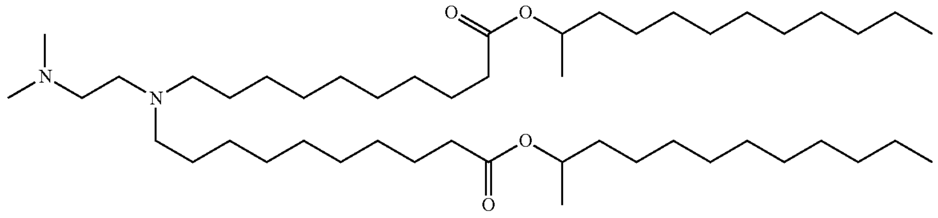 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

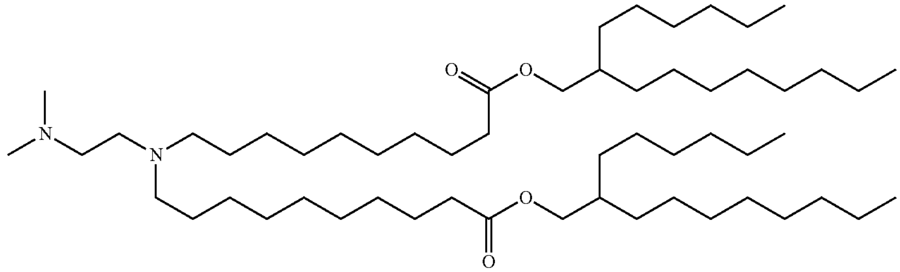 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

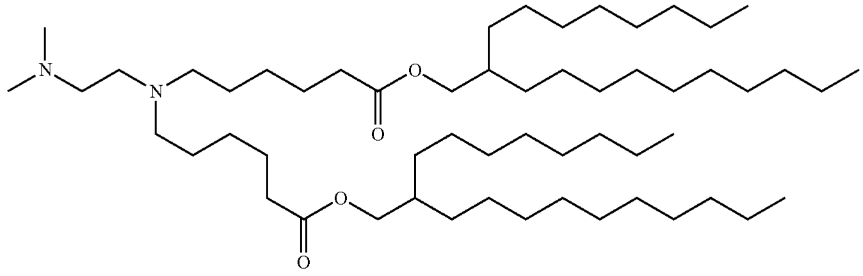 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

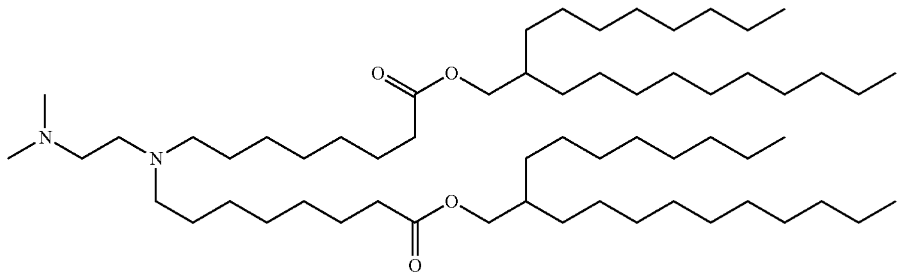 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

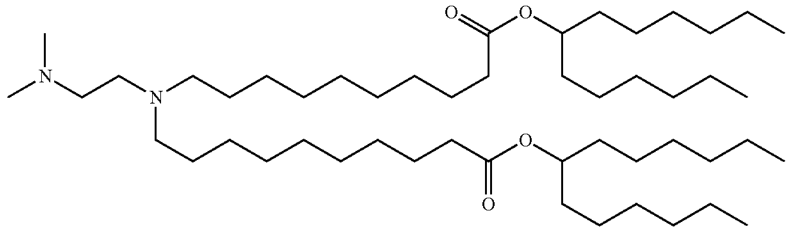 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

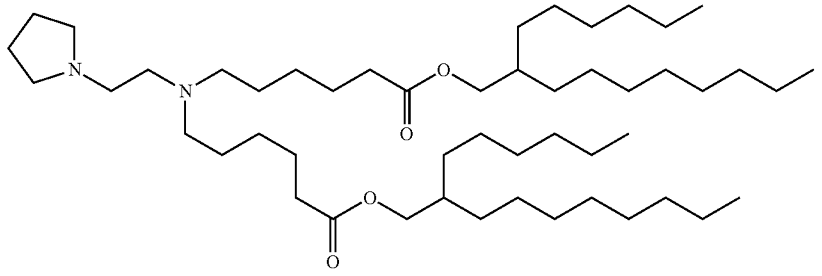 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

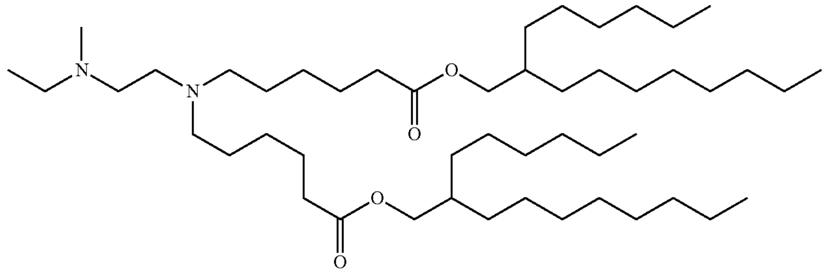 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

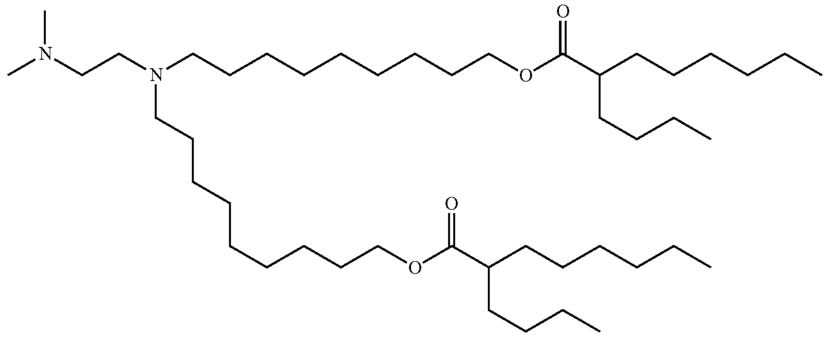 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference for all purposes. In some embodiments, the compositions and methods of the present invention include a cationic lipid having the compound structure:

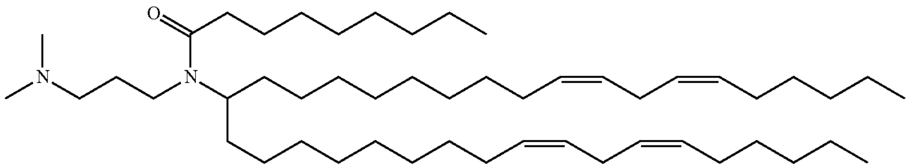 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

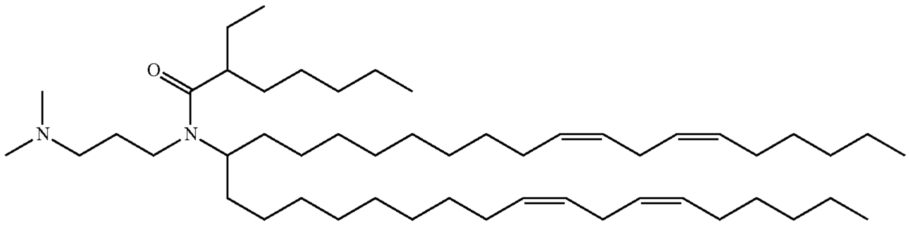 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

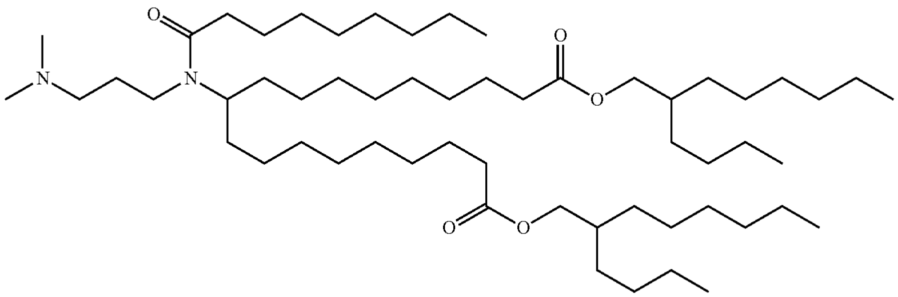 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

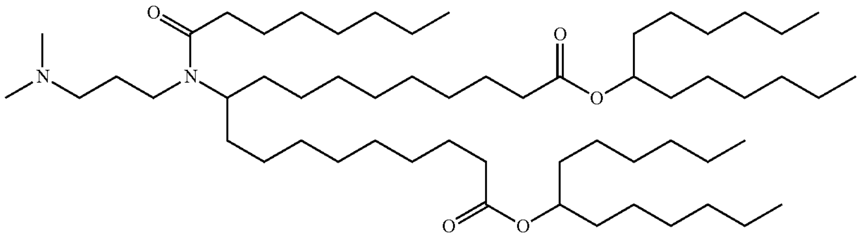 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

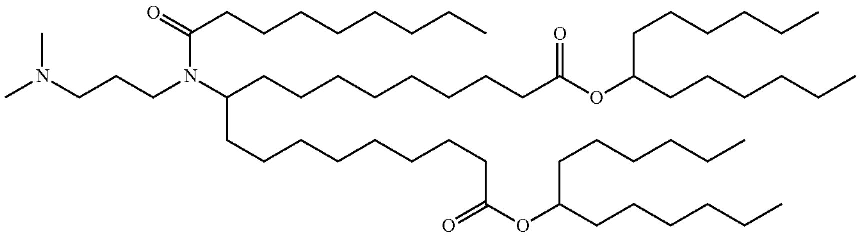 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

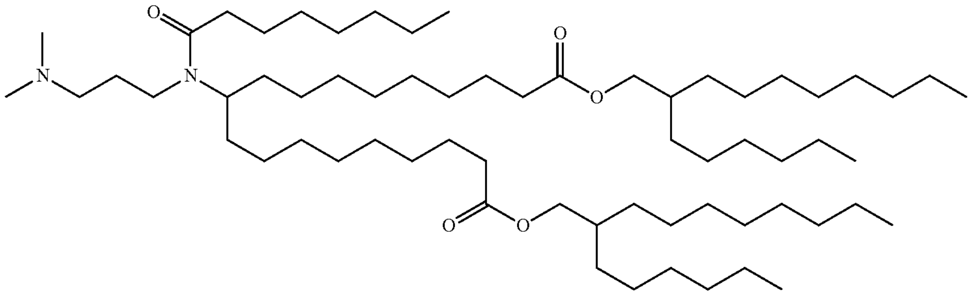 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

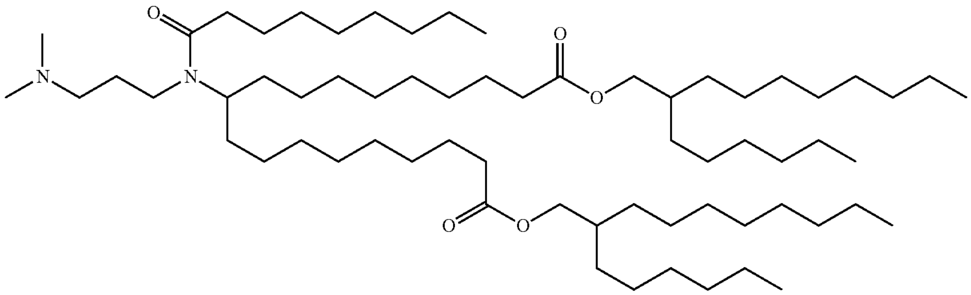 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

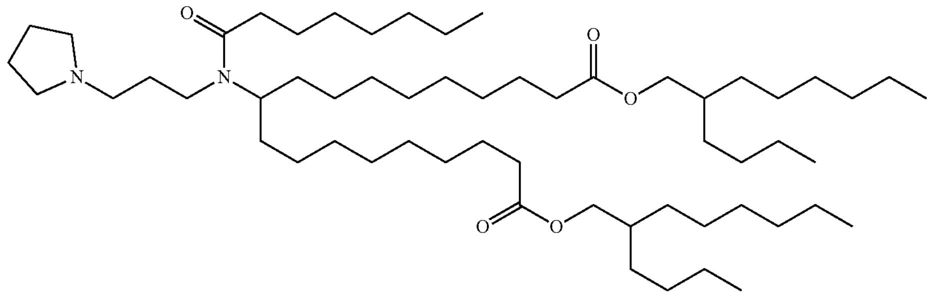 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

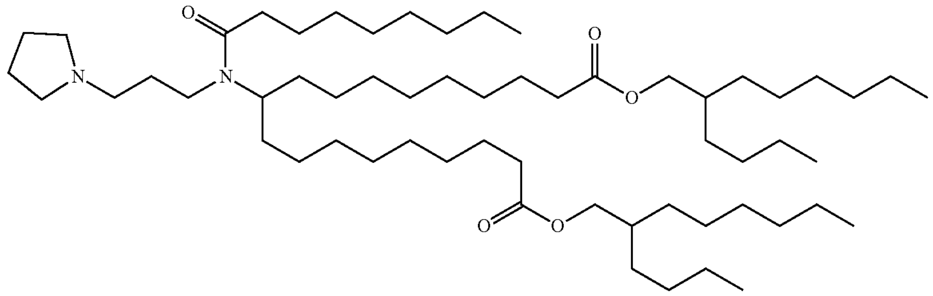 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

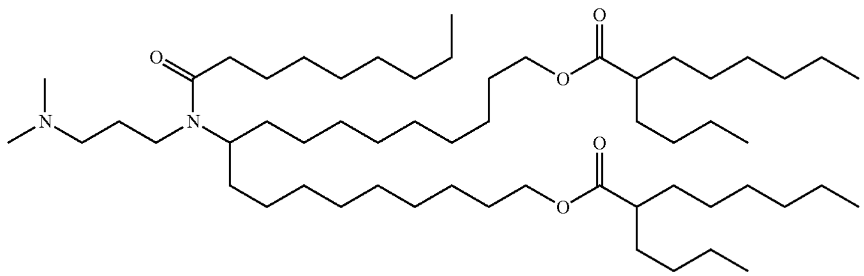 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

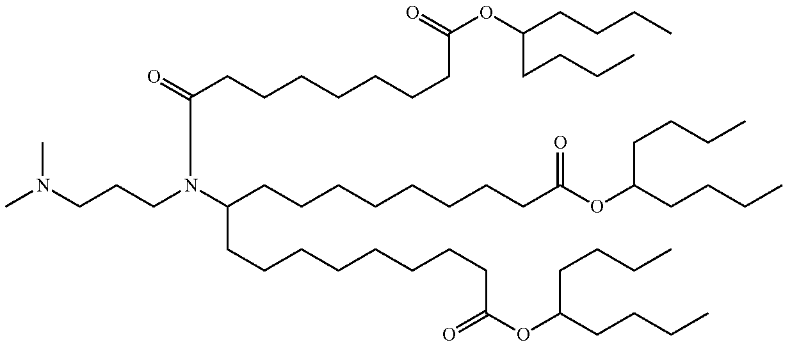 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

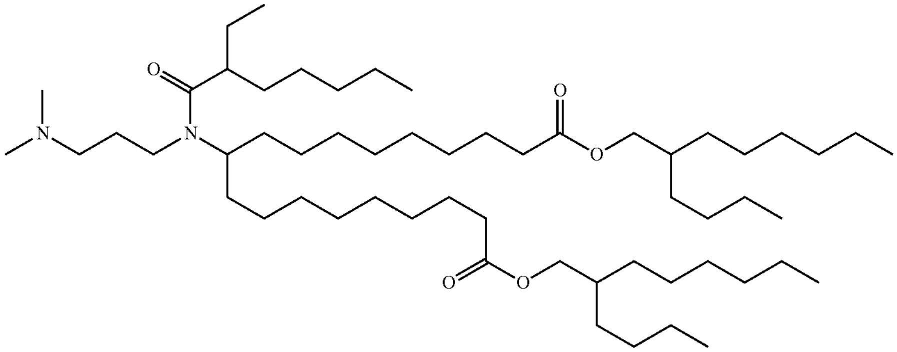 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

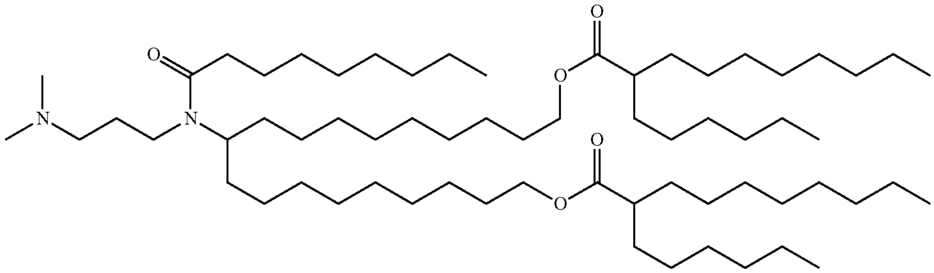 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

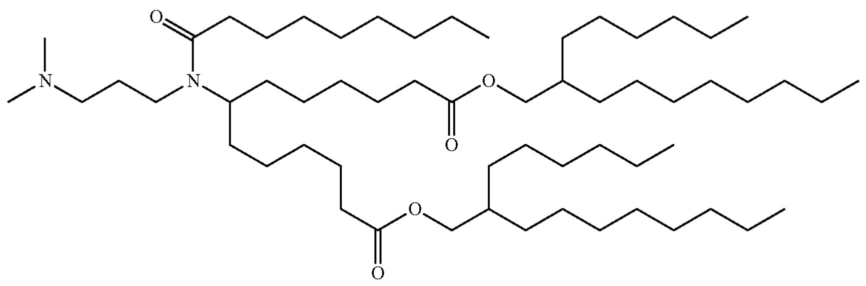 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

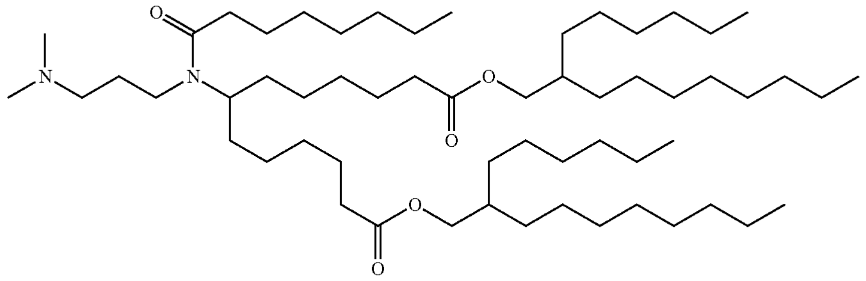 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

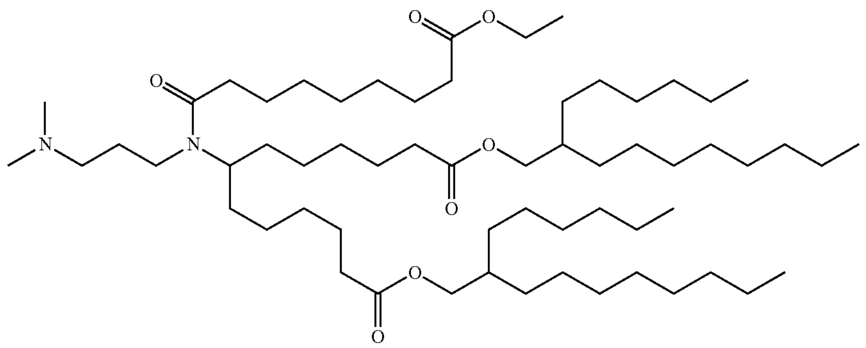 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

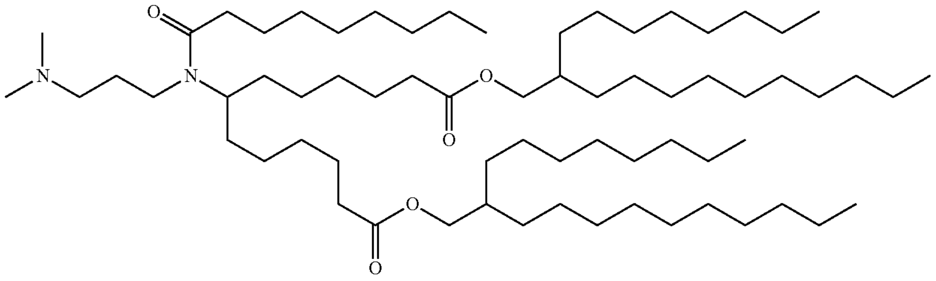 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference for all purposes. In some embodiments, the compositions and methods of the present invention include a cationic lipid of the following formula:

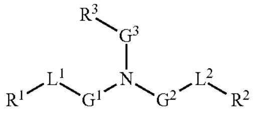

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O) NR$^a$—, NR$^a$C(—O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—NR$^a$C(═O)NR$^a$—, —OC(═O)NR$^a$—or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$ C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference for all purposes. In some embodiments, the compositions and methods of the present invention include a cationic lipid having the compound structure:

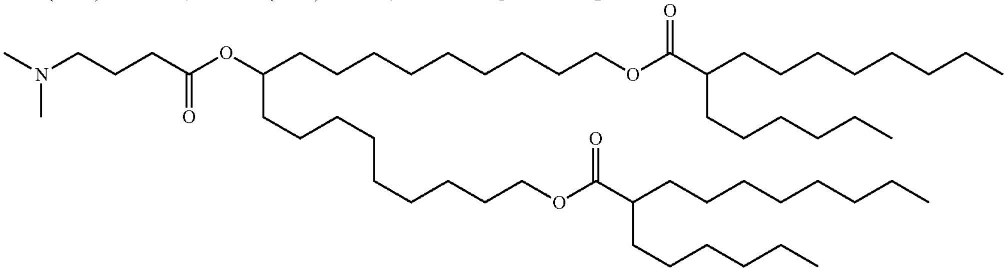 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

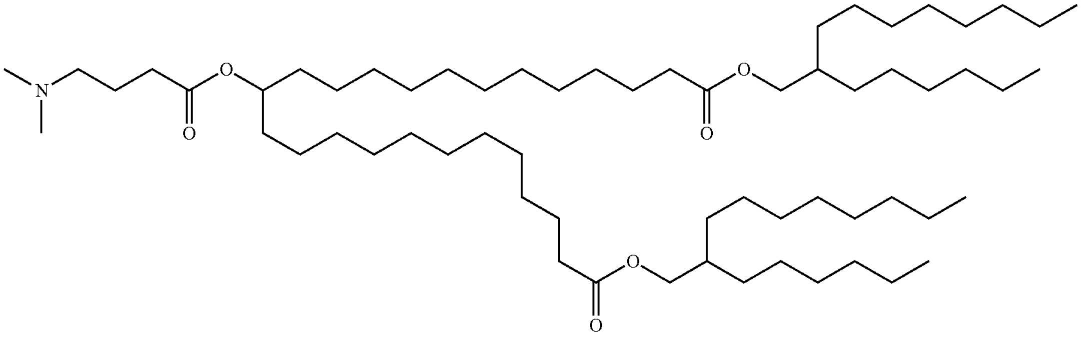 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

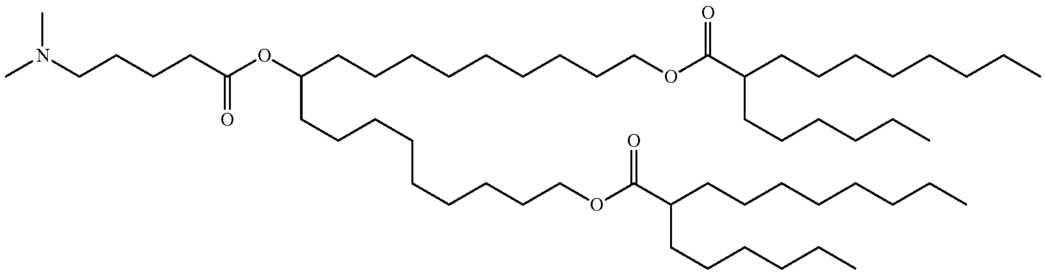 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference for all purposes. In some embodiments, the cationic lipids of the compositions and methods of the present invention include a compound of one of the following formulas:

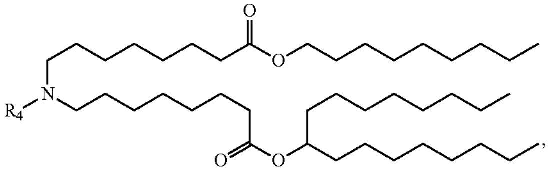

,

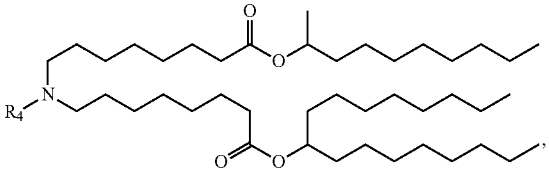

,

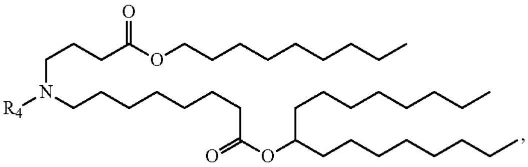

, and

-continued

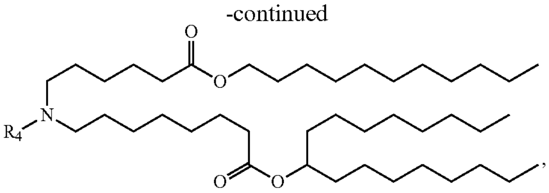

, and pharmaceutically acceptable salts thereof. For any one of these four formulas, $R_4$ is independently selected from $-(CH_2)_nQ$ and $-(CH_2)_nCHQ(R)$; Q is selected from the group consisting of $-OR$, $-OH$, $-O(CH_2)_nN(R)_2$, $-OC(O)R$, $-CX_3$, $-CN$, $-N(R)C(O)R$, $-N(H)C(O)R$, $-N(R)S(O)_2R$, $-N(H)S(O)_2R$, $-N(R)C(O)N(R)_2$, $-N(H)C(O)N(R)_2$, $-N(H)C(O)N(H)(R)$, $-N(R)C(S)N(R)_2$, $-N(H)C(S)N(R)_2$, $-N(H)C(S)N(H)(R)$, and a heterocycle; and n is 1, 2, or 3. In certain embodiments, the compositions and methods of the present invention include a cationic lipid having a compound structure of:

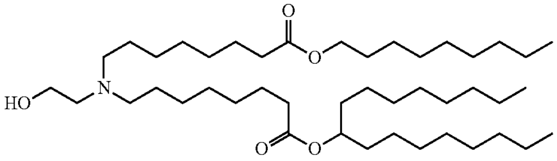 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

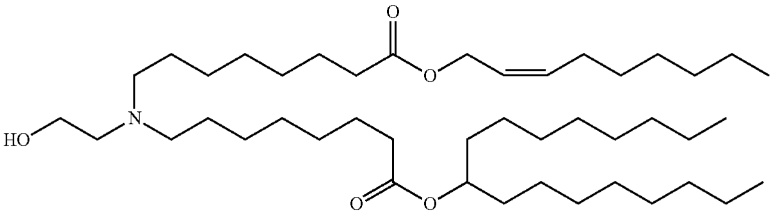 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

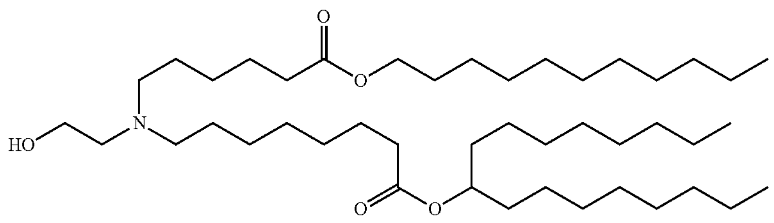 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

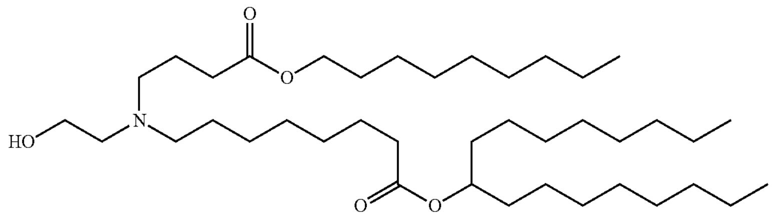 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference for all purposes. In certain embodiments, the compositions and methods of the present invention include a cationic lipid having a compound structure of:

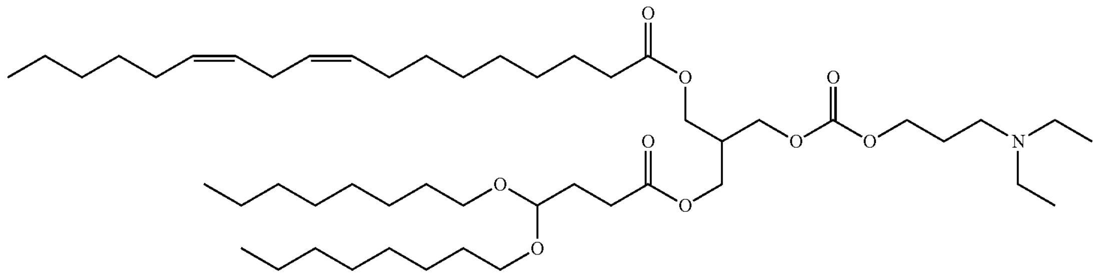 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

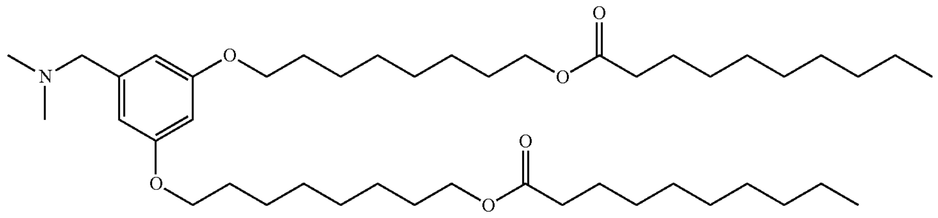 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

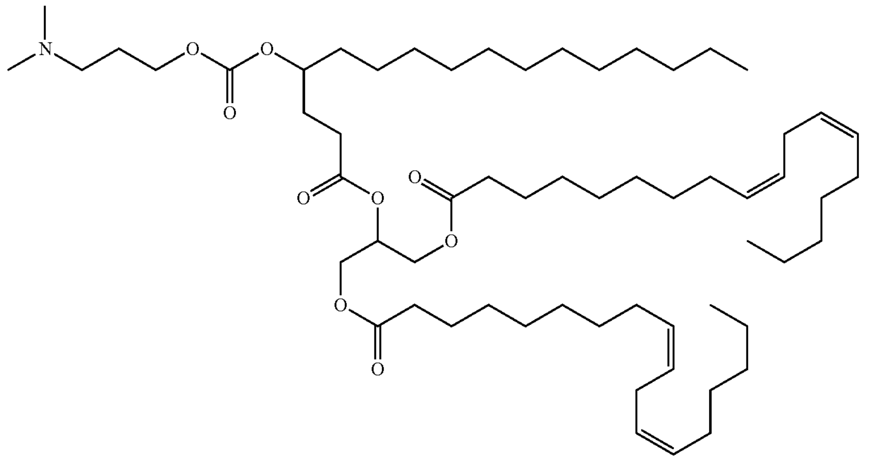 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

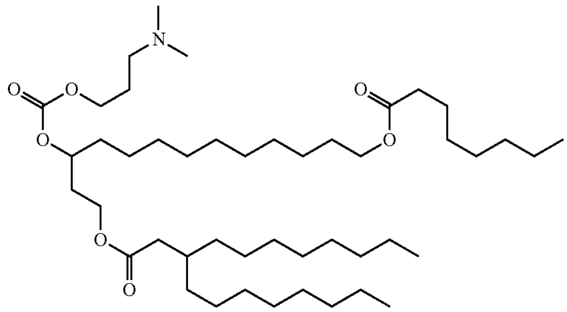 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the invention include cholesterol-based cationic lipids. In certain embodiments, the compositions and methods of the present invention include imidazole cholesterol ester or "ICE", having a compound structure of:

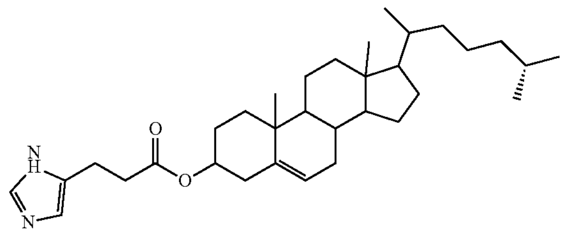

(ICE)

and pharmaceutically acceptable salts thereof.

Other suitable cationic lipids for use in the compositions and methods of the present invention include cleavable cationic lipids as described in International Patent Publication WO 2012/170889, which is incorporated herein by reference for all purposes. In some embodiments, the compositions and methods of the present invention include a cationic lipid of the following formula:

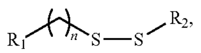

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

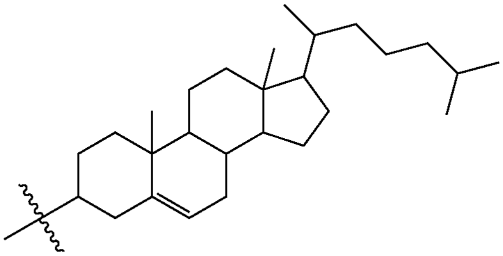

and

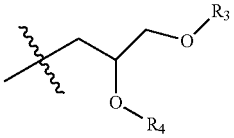

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

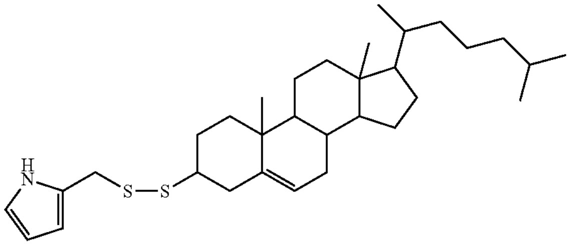

and pharmaceutically acceptable salts thereof. In certain embodiments, the compositions and methods of the present invention include a cationic lipid, "HGT4002", having a compound structure of:

(HGT4002)

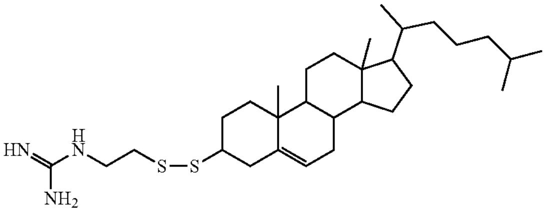

and pharmaceutically acceptable salts thereof. In certain embodiments, the compositions and methods of the present invention include a cationic lipid, "HGT4003", also called "DLin-SS-DMA" which can be used interchangeably, having a compound structure of:

(HGT4003)

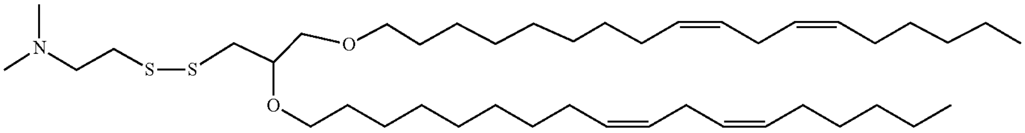

and pharmaceutically acceptable salts thereof. In certain embodiments, the compositions and methods of the present invention include a cationic lipid, "HGT4004", having a compound structure of:

(HGT4004)

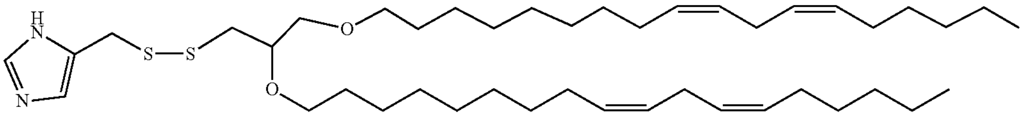

and pharmaceutically acceptable salts thereof. In certain embodiments, the compositions and methods of the present invention include a cationic lipid "HGT4005", having a compound structure of:

(HGT4005)

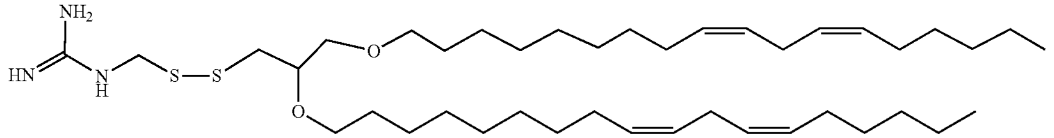

and pharmaceutically acceptable salts thereof.

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, each of which are incorporated herein by reference for all purposes). Other cationic lipids suitable for the compositions and methods of the present invention include, for example, 5-carboxyspermylglycinedioctadecylamide ("DOGS"); 2,3-dioleyloxy-N-[2 (spermine-carboxamido)ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761; each of which are incorporated herein by reference for all purposes); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylarnrnonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N, N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference for all purposes; Semple et al., Nature Biotech. 28: 172-176 (2010), which is incorporated herein by reference for all purposes). (Heyes, J., et al., J Controlled Release 107: 276-287 (2005); Morrissey, D V., et al., Nat. Biotechnol. 23(8): 1003-1007 (2005); International Patent Publication WO 2005/121348; each of which are incorporated herein by reference for all purposes). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. In some embodiments, a non-cationic lipid is a neutral lipid, i.e., a lipid that does not carry a net charge in the conditions under which the composition is formulated and/or administered. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, about 10% to about 70%, about 15% to about 40%, or about 20% to about 35% of the total lipid present in a liposome. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. Suitable cholesterol-based cationic lipids include, for example, DC-Chol (N,N-dimethyl-N-ethylcarboxamidocholesterol),1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335; each of which are incorporated herein by reference for all purposes), or ICE. In some embodiments, the cholesterol-based lipid may comprise a molar ratio of about 2% to about 70%, about 5% to about 65%, about 10% to about 60%, about 15% to about 50%, or about 20% to about 40% of the total lipid present in a liposome. In some embodiments, the percentage of cholesterol-based lipid in the liposome may be greater than 5%, greater than 10%, greater than 20%, greater than 30%, greater than 40%, greater than 50%, or greater than 60%.

PEG Modified Lipids

The use of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a liposome). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). A PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

Sphingolipids

In some embodiments, provided liposomes comprise one or more sphingolipids. Suitable sphingolipids include, for example, sphingosine, ceramide, sphingomyelin, cerebroside and ganglioside. In some embodiments, sphingomyelin is a brain sphingomyelin. In some embodiments, the one or more sphingolipids may comprise a molar ratio of about 5% to about 30%, about 10% to about 25%, or about 15% to about 20% of the total lipid present in a liposome. In some embodiments, the percentage of sphingolipid in the liposome may be greater than 1%, greater than 5%, greater than 10%, greater than 15%, or greater than 20%.

According to various embodiments, the selection of cationic lipids, non-cationic lipids, PEG-modified lipids and/or sphingolipids which comprise the liposome, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethyleneimine (PEI). When PEI is present, it may be branched PEI of a molecular weight ranging from 10 to 40 kDa, e.g., 25 kDa branched PEI (Sigma #408727).

In some embodiments, the compositions and methods of the present invention include a cationic polymer ("PCMMA") of the following formula:

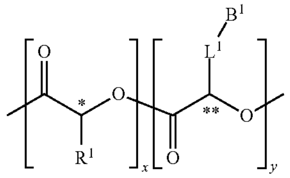

wherein $R^1$ is $C_6$-$C_{20}$ alkyl, $C_6$-$C_{20}$ alkenyl, or $C_6$-$C_{20}$ alkynyl;

$L^1$ is $C_2$-$C_{20}$ alkylene;

$B^1$ is $NR^2R^3$ or a 5- to 10-membered heteroaryl group;

$R^2$ is hydrogen or $C_1$-$C_{20}$ alkyl;

$R^3$ is hydrogen, $C_1$-$C_{20}$ alkyl, or an N-protecting group;

or $R^2$ and $R^3$, together with the nitrogen to which they are attached, combine to form a 5- to 10-membered heterocyclic group;

x is an integer of 5 to 500; and y is an integer of 5 to 500.

and pharmaceutically acceptable salts thereof.

Additional Combinations

A suitable liposome for the present invention may include one or more of any of the cationic lipids, non-cationic lipids, cholesterol lipids, PEG-modified lipids, sphingolipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; ICE, DOPE, and DMG-PEG2K; or cKK-E12, DOPE, cholesterol and DMG-PEG2K, and brain sphingomyelin.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10. In some embodiments, the ratio of cationic lipid(s) to non-cationic lipid(s) to cholesterol-based lipid(s) to PEG-modified lipid(s) to sphingolipid(s) may be between about 30-50:10-30:10-30:1-15:5-25, respectively. In some embodiments, the ratio of cationic lipid(s) to non-cationic lipid(s) to cholesterol-based lipid(s) to PEG-modified lipid(s) to sphingolipid(s) is approximately 35:25:20:10:10, respectively. In some embodiments, the ratio of cationic lipid(s) to non-cationic lipid(s) to cholesterol-based lipid(s) to PEG-modified lipid(s) to sphingolipid(s) is approximately 40:20:20:5:15, respectively. In some embodiments, the ratio of cationic lipid(s) to non-cationic lipid(s) to cholesterol-based lipid(s) to PEG-modified lipid(s) to sphingolipid(s) is approximately 45:15:25:10:5, respectively.

In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE: DMG-PEG-2K molar ratio of >5:1. In some embodiments, the DOPE: DMG-PEG-2K molar ratio is <11:1. In some embodiments, the DOPE: DMG-PEG-2K molar ratio is approximately 7:1. In some embodiments, the DOPE: DMG-PEG-2K molar ratio is approximately 10:1. In some embodiments, a suitable liposome for the present invention comprises ICE, DOPE and DMG-PEG-2K at an ICE:DOPE: DMG-PEG-2K molar ratio of 50:45:5. In some embodiments, a suitable liposome for the present invention comprises ICE, DOPE and DMG-PEG-2K at an ICE:DOPE: DMG-PEG-2K molar ratio of 50:40:10. In some embodiments, a suitable liposome for the present invention comprises ICE, DOPE and DMG-PEG-2K at an ICE:DOPE: DMG-PEG-2K molar ratio of 55:40:5. In some embodiments, a suitable liposome for the present invention comprises ICE, DOPE and DMG-PEG-2K at an ICE:DOPE: DMG-PEG-2K molar ratio of 55:35:10. In some embodiments, a suitable liposome for the present invention comprises ICE, DOPE and DMG-PEG-2K at an ICE:DOPE: DMG-PEG-2K molar ratio of 60:35:5. In some embodiments, a suitable liposome for the present invention comprises ICE, DOPE and DMG-PEG-2K at an ICE:DOPE: DMG-PEG-2K molar ratio of 60:30:10.

Ratio of Distinct Lipid Components

In embodiments where a liposome comprises three and no more than three distinct components of lipids, the ratio of total lipid content (i.e., the ratio of lipid component (1):lipid component (2):lipid component (3)) can be represented as x:y:z, wherein $$(y+z)=100-x.$$

In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z" is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x"

is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3) (e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Formation of Liposomes Encapsulating mRNA

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the methods and compositions of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of cholesterol-based cationic lipid, neutral lipid, and PEG-modified lipid used to create the liposome. In some embodiments, the one or more liposomes may have a different molar ratio of cationic lipid, neutral lipid, cholesterol-based lipid, PEG-modified lipid and sphingolipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference for all purposes. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of the protein encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference for all purposes. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference for all purposes. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Administration and Delivery

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

mRNAs or mRNA-containing delivery vehicles (e.g., liposomes) as described herein, are suitable for CNS delivery. In some embodiments, mRNA-loaded liposomes can be delivered to the CNS via various techniques and routes including, but not limited to, intraparenchymal, intracerebral, intracerebroventricular (ICV), intrathecal (IT e.g., IT-Lumbar, IT-cistema magna, etc) administrations and any other techniques and routes for injection directly or indirectly to the CNS and/or CSF.

In some embodiments, mRNA containing delivery vehicles (e.g., liposomes) are delivered to the CNS by injecting into the cerebrospinal fluid (CSF) of a subject in need of treatment. In some embodiments, intrathecal delivery (also referred to as "intrathecal administration" or "intrathecal injection") is used for delivering mRNA or mRNA-loaded liposomes into the CSF. As used herein, intrathecal delivery refers to an injection into the spinal canal (intrathecal space surrounding the spinal cord). Various techniques may be used including, without limitation, lateral cerebroventricular injection through a burrhole or cistemal or lumbar puncture or the like. Exemplary methods are described in Lazorthes et al., Advances in Drug Delivery Systems and Applications in Neurosurgery, 143-192 and in Omaya et al., Cancer Drug Delivery, 1: 169-179, the contents of each of which are incorporated herein by reference for all purposes.

According to the present invention, mRNA or mRNA loaded liposomes may be injected at any region surrounding the spinal canal. In some embodiments, mRNA or mRNA loaded liposomes are injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S 1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intracerebroventricular (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine.

In some embodiments, intrathecal delivery may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

Provided methods of the present invention contemplate single as well as multiple administrations of a therapeutically effective amount of the therapeutic agents (e.g., mRNA encoding frataxin) described herein. Therapeutic agents can be administered at regular intervals, depending on the nature, severity and extent of the subject's condition (e.g., Friedreich's ataxia). In some embodiments, a therapeutically effective amount of the therapeutic agents (e.g., mRNA encoding a frataxin) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily, or continuously).

In some embodiments, the CNS disease is associated with peripheral symptoms. Thus, in some embodiments, intrathecal administration may be used in conjunction with other routes of administration (e.g., intravenous, subcutaneously, intramuscularly, parenterally, transdermally, or transmucosally (e.g., orally or nasally)).

As used herein, the term "therapeutically effective amount" is largely determined based on the total amount of mRNA contained in the pharmaceutical compositions of the present invention. Generally, a therapeutically effective amount is sufficient to achieve a meaningful benefit to the subject (e.g., treating, modulating, curing, preventing and/or ameliorating Friedreich's ataxia). For example, a therapeutically effective amount may be an amount sufficient to achieve a desired therapeutic and/or prophylactic effect. Generally, the amount of mRNA administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intrathecally or intravenously. In some embodiments, the intrathecal dose is or is greater than 1, 2, 3, 4, 5, 6, 7, 8, 9, 10, 15 or 20 μg. In some embodiments, the intravenous dose is or is greater than 0.5 or 1 mg.

Provided liposomes and compositions may be administered to any desired tissue. In some embodiments, the FXN mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, dorsal root ganglia, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for FXN mRNA Delivery and Expression This example provides exemplary liposome formulations for effective delivery and expression of FXN mRNA in vivo.

Exemplary codon-optimized FXN mRNAs as described above, including SEQ ID NOs: 1, 2, and 4 were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length as determined by gel electrophoresis. The mRNA encoding frataxin protein also comprised 5' and 3' untranslated regions (UTRs) (vide supra).

An aqueous-based solution comprising the exemplary mRNA encoding frataxin protein was combined with one of two ethanol-based lipid solutions, isolated and dialyzed into the final formulation appropriate for storage at −80° C.

One lipid solution contained five lipid components to form liposomes. The five biodegradable components all contributed to the final drug product characteristics. The first component was a cationic lipid (e.g., ICE, cKK-E12, CCBene, etc.). Without being bound by theory, this afforded a positively charged environment at low pH which facilitates efficient encapsulation of the negatively charged mRNA. It may also play a key role in cell surface interaction to allow for cellular uptake. The second component of the lipid nanoparticle (LNP) was a non-cationic lipid (e.g., 1,2-dioleoyl-sn-glycero-3-phosphoethanolamine (DOPE)). Without being bound by theory, DOPE is a zwitterionic lipid that has been reported to have fusogenic properties to enhance uptake and release of the drug payload. The third component was cholesterol. Without being bound by theory, cholesterol provided stability giving rigidity to the lipid bilayer. The fourth component was a PEGylated (i.e., PEG-modified) lipid (e.g., 1,2-dimyristoyl-sn-glycerol, methoxypolyethylene glycol (DMG-PEG-2K)). Without being bound by theory, the addition of this PEGylated lipid provided control over particle size and stability of the nanoparticle and may provide enhanced mucopentrating properties for lung uptake. The fifth component was a sphingomyelin (e.g., brain sphingomyelin). Sphingomyelin in an endogenous lipid component found in all mammalian cells and enriched in central nervous system tissue. Without being bound by theory, the brain sphingomyelin was incorporated to provide means to represent a more endogenous lipid vesicle for the CNS.

Another lipid solution contained three lipid components to form liposomes. The three components all contributed to the final drug product characteristics. The first component was an ionizable lipid (e.g., imidazole cholesterol ester (ICE), cKK-E12, CCBene, etc.). Without being bound by theory, this afforded a positively charged environment at low pH which facilitates efficient encapsulation of the negatively charged mRNA. It may also play a key role in cell surface interaction to allow for cellular uptake. The second component of the LNP was a non-cationic lipid (e.g., 1,2-dioleoyl-sn-glycero-3-phosphoethanolamine (DOPE)). Without being bound by theory, DOPE is a zwitterionic lipid that has been reported to have fusogenic properties to enhance uptake and release of the drug payload. The third component was a PEGylated (i.e., PEG-modified) lipid (e.g., 1,2-dimyristoyl-sn-glycerol, methoxypolyethylene glycol (DMG-PEG-2K)). Without being bound by theory, the addition of this PEGylated lipid provided control over particle size and stability of the nanoparticle and may provide enhanced mucopentrating properties for lung uptake. The nominal nitrogen/phosphorus (N/P) charge ratio of the LNP was 4, and the average particle size range for the mRNA encapsulated in the LNP was 40-60 nm.

Example 2. In Vitro Transfection of HEK Cells with mRNA-Loaded Liposome Nanoparticles and In Vitro Detection of Produced Frataxin This example illustrates exemplary methods of transfecting cells with FXN mRNA-loaded liposomes and methods for detecting frataxin protein in the cells.

Briefly, an aliquot of each selected mRNA was complexed with Lipofectamine 2000 and applied to wells containing HEK293 cells for transfection. Approximately 18 hours later, the cells were harvested and lysed for human FXN analysis.

FXN mRNA was produced as described above in Example 1. Subsequently, in accordance with the exemplary protocol described above, 4.0, 2.0, 1.0 and 0.5 μg of FXN mRNA was transfected into HEK cells. Frataxin protein was produced in HEK cells as described above.

HEK cells were extracted with 100 μl or 150 μl of extraction solution (RIPA buffer (Thermo Fisher #89900)+protease inhibitor (Roche 1183617001)). Samples were placed on ice for 20 minutes to allow foam settle, transferred to a new tube, and cleared by centrifuge at 20,000×g for 10 minutes at 4° C. The supernatant were collected and quantified using a BCA assay. Protein extracts (2.5-30 μg) were mixed with NuPage LDS loading buffer (NP0007), run on 10% bis tris NuPage gels (WG1202BOX), and transferred onto Nitrocellulose membrane (1704159) using the Trans-Blot® Turbo™ Transfer System (Bio-Rad; 1704155). Blots were imaged and quantified using the LiCor Odyssey imaging system. Frataxin was imaged using mouse anti-human FXN monoclonal antibody (ab110328, Abcam) and GAPDH was imaged using rabbit anti-mouse GAPDH (8884s, Cell Signaling). Conjugated fluorescent secondary antibodies were used for visualization donkey anti-mouse IgG DαM800CW (LI-COR, 926-32210) and goat anti-rabbit IgG GaR680RD (LiCor, 926-68071). The protein band fluorescent intensity was measured and quantified using the Image Studio program (LiCor).

Detection of frataxin protein in HEK cells was achieved using immunological detection methods (e.g. Western blot). As demonstrated in FIG. 1, the exogenous mature human frataxin protein was detected when cells were transfected with 4.0, 2.0, 1.0 or 0.5 μg of FXN mRNA. This was true for all three tested codon-optimized FXN mRNAs (hFXN-159 (comprising SEQ ID NO: 1), hFXN-160 (comprising SEQ ID NO: 2) and hFXN-162 (comprising SEQ ID NO: 4)). Exogenous mature human frataxin protein was not detected in cells transfected with lipofectamine alone.

Example 3. Intravenous Administration of FXN mRNA-Loaded Liposome Nanoparticles This example illustrates exemplary methods of administering FXN mRNA-loaded liposomes via intravenous administration that results in in vivo expression of frataxin protein and detection of that frataxin protein in various tissues, including heart tissue, of a subject, and provides methods for analyzing FXN mRNA and frataxin protein in various target tissues, including heart tissue, of a subject.

All studies were performed using CD-1 mice. Mice were treated with either human FXN mRNA-loaded cKK-E12-based liposomes (MRT1 comprised SEQ ID NO: 1, MRT2 comprised SEQ ID NO: 2 and MRT3 comprised SEQ ID NO: 4) or human FXN mRNA-loaded ICE-based liposomes (MRT 4, MRT 5 and MRT 6) by a single bolus tail-vein injection of a 0.5 mg/kg or 1.0 mg/kg dose. Mice were sacrificed 24 hours after dose administration.

Tissues, including liver, heart, spinal cord, dorsal root ganglia (DRG) and brain of each mouse were harvested, and apportioned into separate parts as described herein. For liver collection, 3 medial lobe biopsies and 2 lateral lobe biopsies were taken, with 1 medial and 1 lateral biopsy used for testing RNA and 2 medial and 1 lateral biopsy used for testing protein. For heart collection, the hearts were bisected, with half used for testing RNA and half used for testing protein. For spinal cord collection, the spinal cords were divided into thoracic and lumbar portions, with the thoracic portion used for testing RNA and the lumbar portion used for testing protein. For DRG collection, the DRG (target of 20 per animal) on each lateral side of T1-L6 were collected. For brain collection, the cerebellum and cerebrum were bisected along the sagittal midline, with half of each region used for testing RNA and the other half used for testing protein. For each tissue, samples used for RNA testing were stored in RNALater and samples used for protein testing were snap frozen in LN2.

Western Blot Detection of Frataxin Protein in Mouse Tissue Homogenate

Liver or heart or CNS tissues (~30-100 mg) were transferred to Omni tube (2 mL Tube with 2.8 mm Ceramic Beads) and mixed with 300-700 μL of tissue extraction buffer (RIPA buffer+protease inhibitor) and lysed by using Omni Bead Ruptor 24 Homogenizer at 5000 rpm for 20 seconds. Samples were placed on ice for 20 minutes to allow foam settle, transferred to a new tube, and cleared by centrifuge at 20,000×g for 10 minutes at 4° C. Dorsal Root Ganglia (DRG) lysates were prepared using a grinder due to the small amount of tissue available. 10 to 20 DRG were collected into a cryo-tube on dry ice and stored at −80° C. Keeping DRGs on ice, 50 μL of tissue extraction buffer was added, and DRGs were ground with a motorized pestle (Fisher, pestle #12-141-364; using a motor #7495410000), incubated on ice for 30-40 minutes, and lysates were cleared by centrifugation at 20,000×g for 10 minutes at 4° C. The supernatant was collected and quantified using a BCA assay. Protein extracts were mixed with NuPage LDS loading buffer (NP0007), run on 10% bis tris NuPage gels (WG1202BOX), and transferred onto Nitrocellulose membrane (1704159) using the Trans-Blot® Turbo™ Transfer System (Bio-Rad; 1704155). Blots were imaged and quantified using the LiCor Odyssey imaging system. Frataxin was imaged using mouse anti-human FXN monoclonal antibody (ab110328, Abcam) and GAPDH was imaged using rabbit anti-mouse GAPDH (8884s, Cell Signaling). Conjugated fluorescent secondary antibodies were used for visualization donkey anti-mouse IgG DαM800CW (LI-COR, 926-32210) and goat anti-rabbit IgG GaR680RD (LiCor, 926-68071). The protein band fluorescent intensity was measured and quantified using the Image Studio program (LiCor).

ELISA Quantification of Frataxin Protein in Mouse Tissue Homogenate

All ELISAs were performed using the commercially available SimpleStep Human Frataxin ELISA Kit (ab176112). Liver or heart or CNS tissues (~30-100 mg) were transferred to Omni tube (2 mL Tube with 2.8 mm Ceramic Beads) and mix with 300-700 μl of tissue extraction buffer (RIPA buffer+protease inhibitor) and lysed by using Omni Bead Ruptor 24 Homogenizer at 5000 rpm for 20 seconds. Samples were placed on ice for 20 minutes to allow foam settle, transferred to a new tube, and cleared by centrifuge at 20,000×g for 10 minutes at 4° C. The supernatant was collected and quantified using a BCA assay. The extracts were diluted with 1× Cell Extraction buffer to fit within the linear range of the recombinant hFXN standard, starting at roughly 20 ng/μL. 50 μL of each extract was transferred to a well in 8-well strips in a 96-well plate format and mixed with 50 μL of the Antibody Cocktail. Plates were sealed and incubated at room temp for 70 minutes on a plate shaker set to 400 rpm. Plates were washed 3×350 μL with 1× Wash Buffer PT. Buffer was completely removed by aspiration at each step. The plate was inverted and blotted on clean paper towels to remove excess liquid. 100 μL of TMB Substrate was added to each well and incubated for 10 minutes in the dark on a plate shaker set to 400 rpm. 100 μL of Stop Solution was added to each well, the plate was shaken for 1 minute to mix, and the OD was recorded at 450 nm. Background was subtracted for each well. Readings from the recombinant hFXN standard (0-800 pg/mL) were used to construct a standard curve. A log/log four parameter algorithm (4PL) was used to fit the standard curve and the protein concentrations of the unknown samples were interpolated from that curve.

Results

Figure 2:
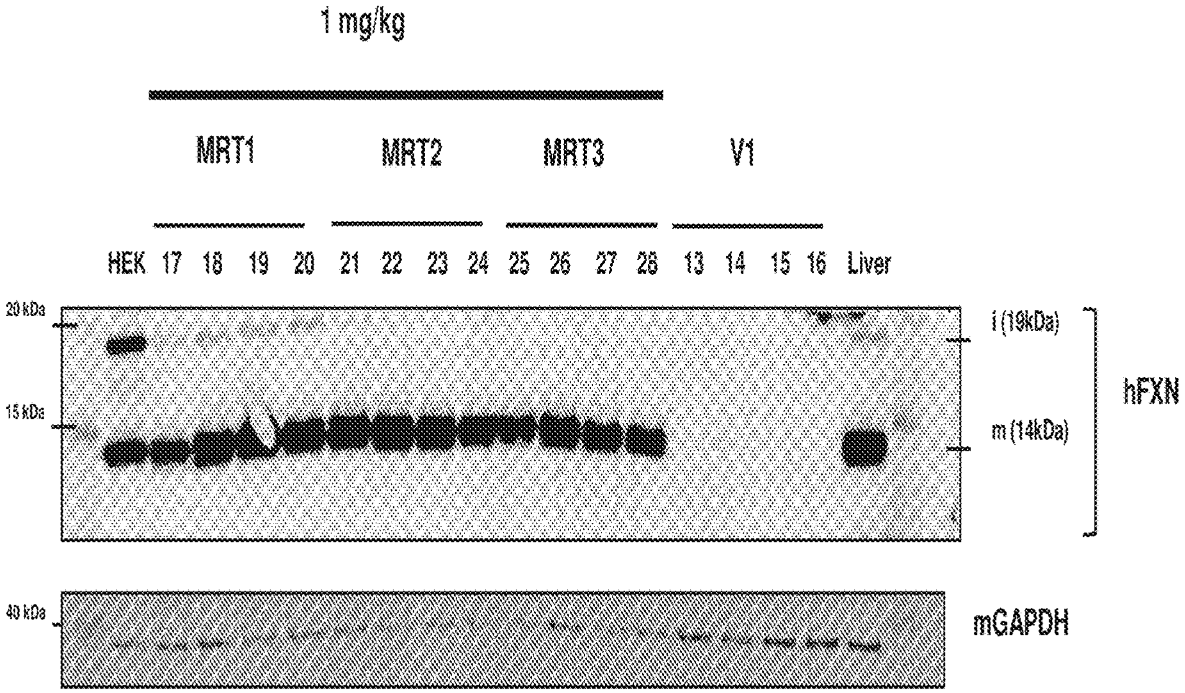
FIG. 2 depicts exemplary detection of human frataxin protein by Western blot in liver samples from mice treated with a single intravenous dose of hFXN mRNA-loaded liposomes.

Detection of frataxin protein in the livers of the treated mice was achieved using antibody-based methods (e.g. Western blot). As demonstrated in FIG. 2, the exogenous human frataxin protein was detected in all three mRNA-liposome combinations (MRT1 comprised SEQ ID NO: 1, MRT2 comprised SEQ ID NO: 2 and MRT3 comprised SEQ ID NO: 4). However, there was differential expression of the intermediate human frataxin protein observed between the three mRNA treatments.

Figure 3A:
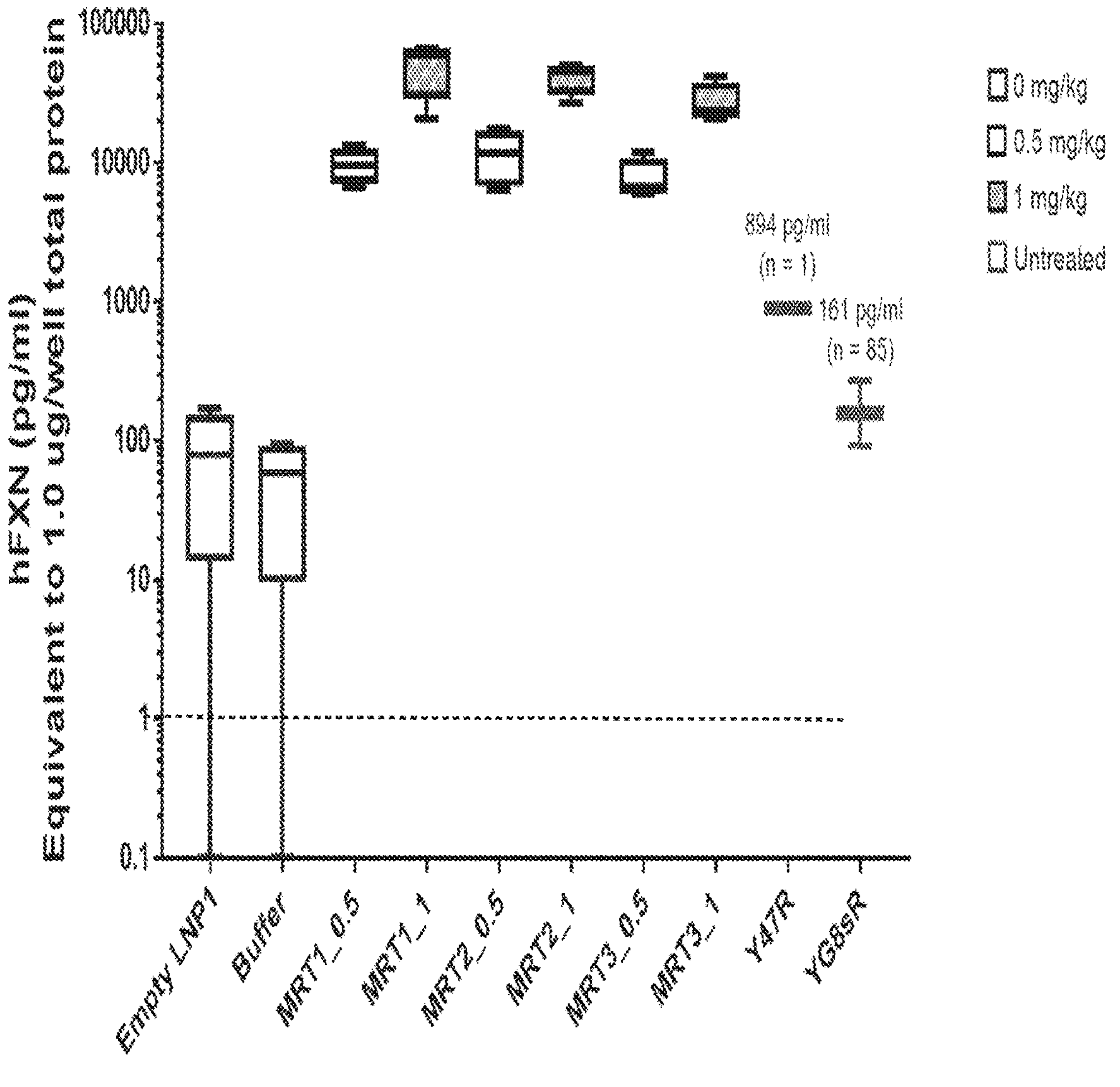
FIG. 3A depicts exemplary detection of human frataxin protein by ELISA in liver samples from mice treated with a single intravenous dose of hFXN mRNA-loaded liposomes.
Figure 3B:
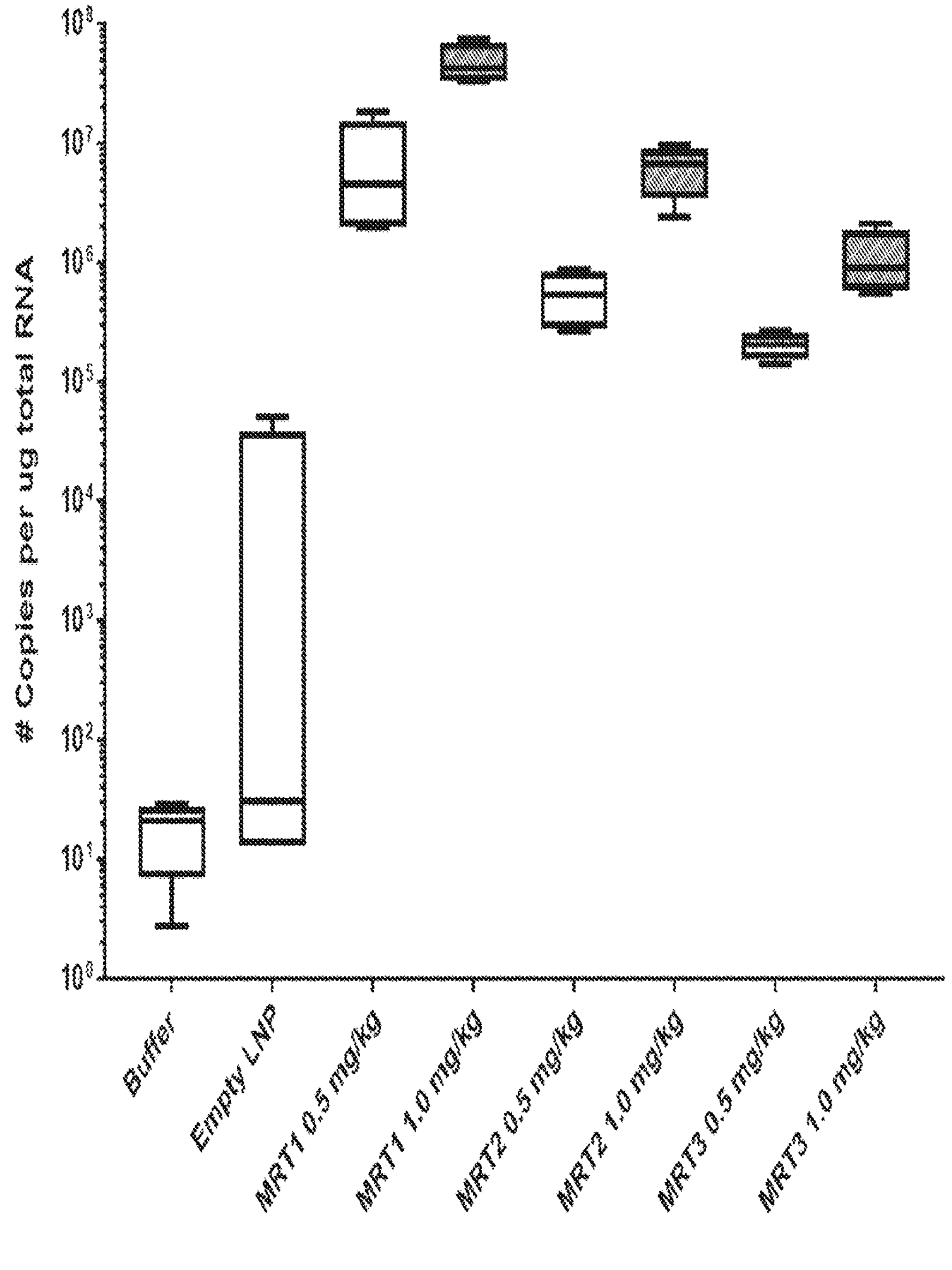
FIG. 3B depicts exemplary detection of hFXN mRNA by RT qPCR in liver samples from mice treated with a single intravenous dose of hFXN mRNA-loaded liposomes.

Additionally, the mRNA-derived human frataxin protein was detected as a robust signal with ELISA performed on liver samples. As shown in FIG. 3A, both 0.5 mg/kg and 1.0 mg/kg doses of mRNA delivered via IV administration resulted in human frataxin protein being delivered to and detectable in the liver, as compared to controls. FIG. 3B shows that a robust mRNA signal was detected by RT qPCR from liver samples.

Figure 4A:
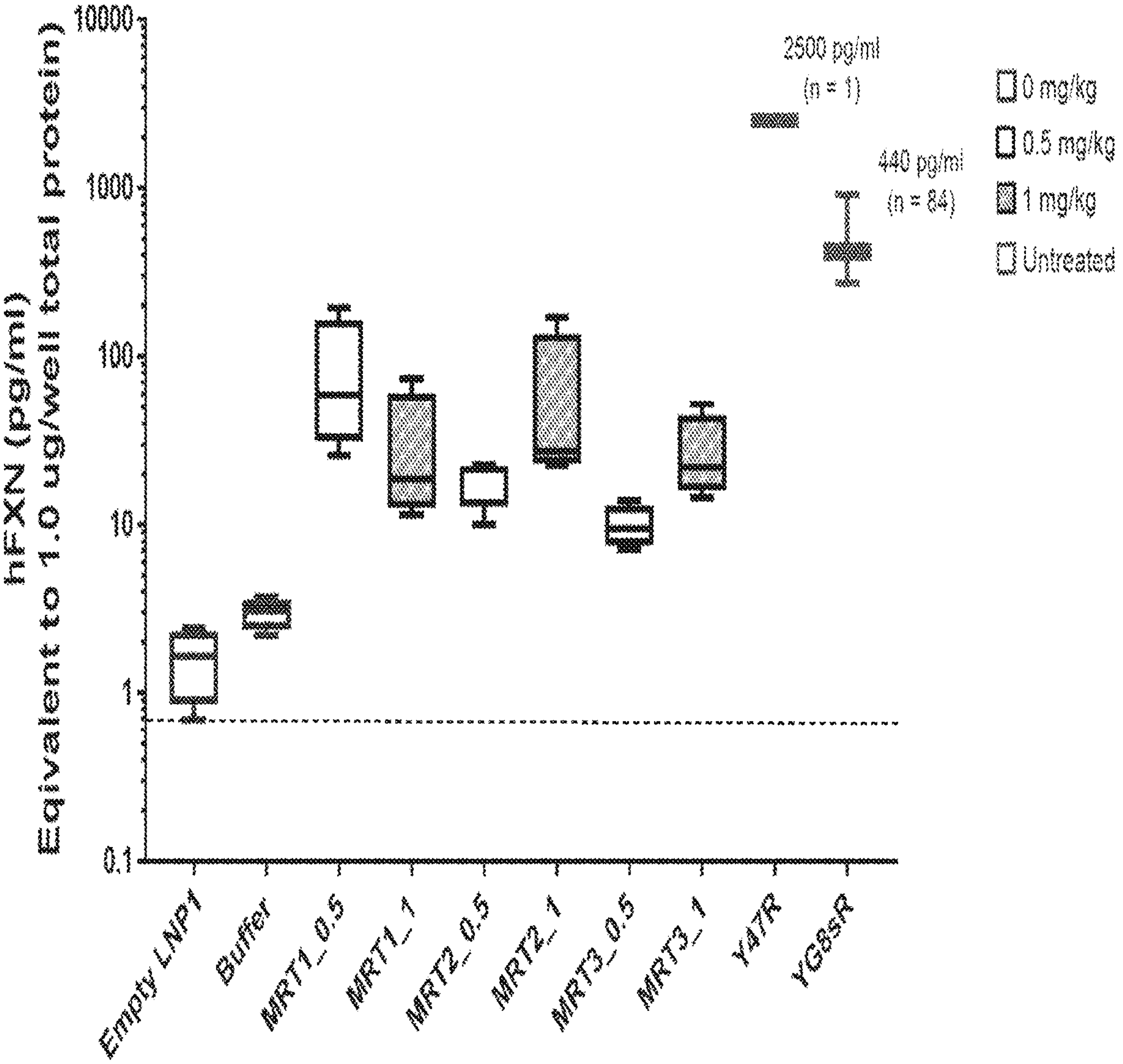
FIG. 4A depicts exemplary detection of human frataxin protein by ELISA in heart samples from mice treated with a single intravenous dose of hFXN mRNA-loaded liposomes.
Figure 4B:
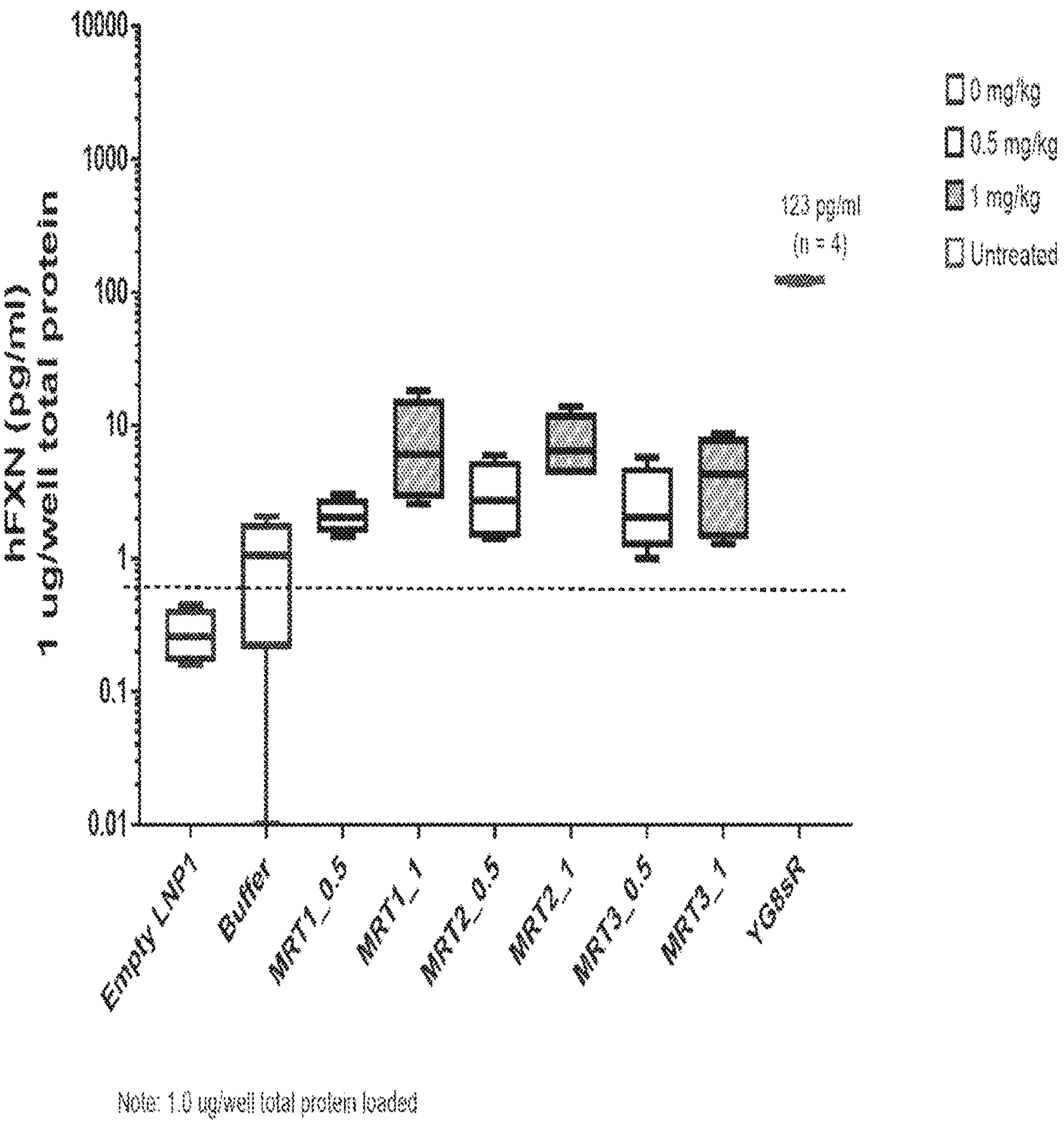
FIG. 4B depicts exemplary detection of human frataxin protein by ELISA in DRG samples from mice treated with a single intravenous dose of hFXN mRNA-loaded liposomes.

The mRNA-derived human frataxin protein also was detected with ELISA in the heart tissue and in the DRG of subjects. As shown in FIG. 4A, both 0.5 mg/kg and 1.0 mg/kg doses of mRNA delivered via IV administration resulted in human frataxin protein being delivered to and detectable in the heart, as compared to controls. As shown in FIG. 4B, both 0.5 mg/kg and 1.0 mg/kg doses of mRNA delivered via IV administration resulted in human frataxin protein being delivered to and detectable in the DRG, as compared to controls.

Example 4. Intrathecal Administration of FXN mRNA-Loaded Liposome Nanoparticles This example illustrates exemplary methods of administering FXN mRNA-loaded liposomes via intrathecal administration that results in in vivo expression of frataxin protein and detection of that frataxin protein in various tissues, including cerebellum tissue, of a subject, and provides methods for analyzing FXN mRNA and frataxin protein in various target tissues, including cerebellum tissue, of a subject.

All studies were performed using CD-1 mice. Mice were treated with either human FXN mRNA-loaded cKK-E12-based liposomes (MRT 1, MRT 2 and MRT 3) or human FXN mRNA-loaded ICE-based liposomes (MRT 4, MRT 5 and MRT 6) by a single intrathecal (IT) bolus of a 5 μg/animal, 10 μg/animal or 20 μg/animal dose while under inhaled isoflurane anesthesia. Mice were sacrificed 24 hours after dose administration.

Tissues, including liver, spinal cord, dorsal root ganglia (DRG) and brain, including cerebellum, of each mouse were harvested, and apportioned into separate parts as described herein. For liver collection, 3 medial lobe biopsies and 2 lateral lobe biopsies were taken, with 1 medial and 1 lateral biopsy used for testing RNA and 2 medial and 1 lateral biopsy used for testing protein. For spinal cord collection, the spinal cords were divided into thoracic and lumbar portions, with the thoracic portion used for testing RNA and the lumbar portion used for testing protein. For DRG collection, the DRG (target of 20 per animal) on each lateral side of T1-L6 were collected. For brain collection, the cerebellum and cerebrum were bisected along the sagittal midline, with half of each region used for testing RNA and the other half used for testing protein. For each tissue, samples used for RNA testing were stored in RNALater and samples used for protein testing were snap frozen in LN2.

Western Blot Detection of Frataxin Protein in Mouse Tissue Homogenate

Liver or heart or CNS tissues (~30-100 mg) were transferred to Omni tube (2 mL Tube with 2.8 mm Ceramic Beads) and mixed with 300-700 μL of tissue extraction buffer (RIPA buffer+protease inhibitor) and lysed by using Omni Bead Ruptor 24 Homogenizer at 5000 rpm for 20 seconds. Samples were placed on ice for 20 minutes to allow foam settle, transferred to a new tube, and cleared by centrifuge at 20,000×g for 10 minutes at 4° C. Dorsal Root Ganglia (DRG) lysates were prepared using a grinder due to the small amount of tissue available. 10 to 20 DRG were collected into a cryo-tube on dry ice and stored at −80° C. Keeping DRGs on ice, 50 μL of tissue extraction buffer was added, and DRGs were ground with a motorized pestle (Fisher, pestle #12-141-364; using a motor #7495410000), incubated on ice for 30-40 minutes, and lysates were cleared by centrifugation at 20,000×g for 10 minutes at 4° C. The supernatant was collected and quantified using a BCA assay. Protein extracts were mixed with NuPage LDS loading buffer (NP0007), run on 10% bis tris NuPage gels (WG1202BOX), and transferred onto Nitrocellulose membrane (1704159) using the Trans-Blot® Turbo™ Transfer System (Bio-Rad; 1704155). Blots were imaged and quantified using the LiCor Odyssey imaging system. Frataxin was imaged using mouse anti-human FXN monoclonal antibody (ab110328, Abcam) and GAPDH was imaged using rabbit anti-mouse GAPDH (8884s, Cell Signaling). Conjugated fluorescent secondary antibodies were used for visualization donkey anti-mouse IgG DαM800CW (LI-COR, 926-32210) and goat anti-rabbit IgG GaR680RD (LiCor, 926-68071). The protein band fluorescent intensity was measured and quantified using the Image Studio program (LiCor).

ELISA Quantification of Frataxin Protein in Mouse Tissue Homogenate

All ELISAs were performed using the commercially available SimpleStep Human Frataxin ELISA Kit (ab176112). Liver or heart or CNS tissues (~30-100 mg) were transferred to Omni tube (2 mL Tube with 2.8 mm Ceramic Beads) and mix with 300-700 μl of tissue extraction buffer (RIPA buffer+protease inhibitor) and lysed by using Omni Bead Ruptor 24 Homogenizer at 5000 rpm for 20 seconds. Samples were placed on ice for 20 minutes to allow foam settle, transferred to a new tube, and cleared by centrifuge at 20,000×g for 10 minutes at 4° C. The supernatant was collected and quantified using a BCA assay. The extracts were diluted with 1× Cell Extraction buffer to fit within the linear range of the recombinant hFXN standard, starting at roughly 20 ng/μL. 50 μL of each extract was transferred to a well in 8-well strips in a 96-well plate format and mixed with 50 μL of the Antibody Cocktail. Plates were sealed and incubated at room temp for 70 minutes on a plate shaker set to 400 rpm. Plates were washed 3×350 μL with 1× Wash Buffer PT. Buffer was completely removed by aspiration at each step. The plate was inverted and blotted on clean paper towels to remove excess liquid. 100 μL of TMB Substrate was added to each well and incubated for 10 minutes in the dark on a plate shaker set to 400 rpm. 100 μL of Stop Solution was added to each well, the plate was shaken for 1 minute to mix, and the OD was recorded at 450 nm. Background was subtracted for each well. Readings from the recombinant hFXN standard (0-800 pg/mL) were used to construct a standard curve. A log/log four parameter algorithm (4PL) was used to fit the standard curve and the protein concentrations of the unknown samples were interpolated from that curve.

Results

Figure 5A:
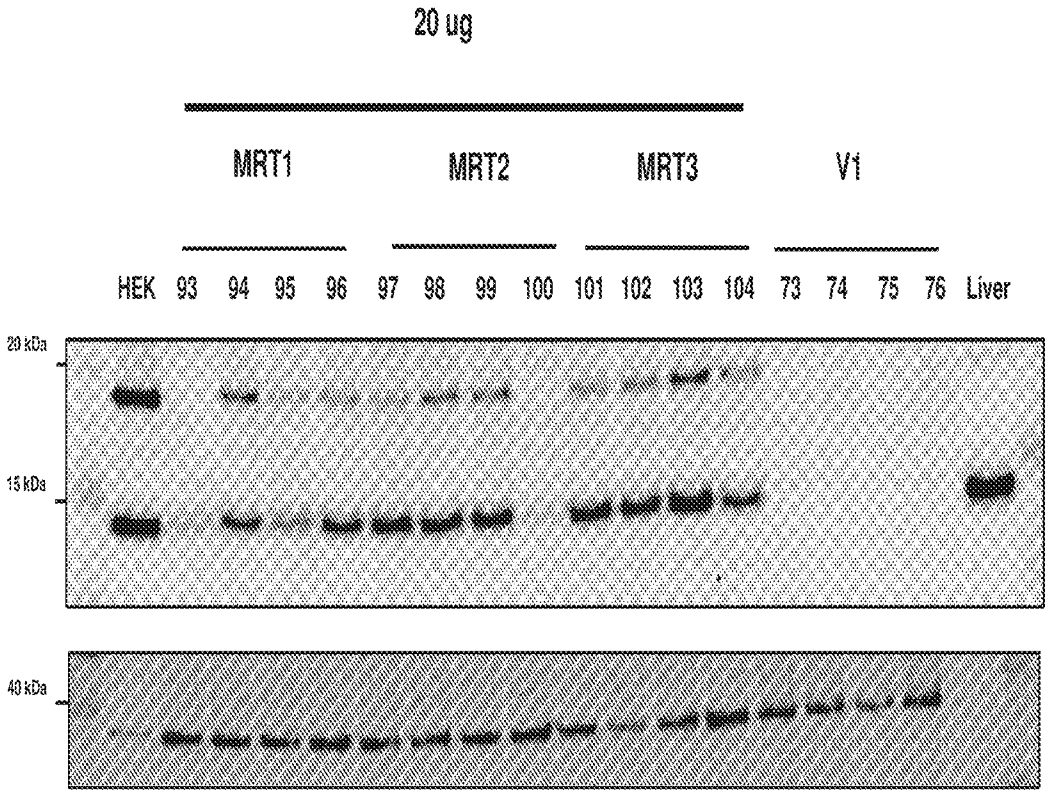
FIG. 5A depicts exemplary detection of human frataxin protein by Western blot in DRG samples from mice treated with a single intrathecal dose of hFXN mRNA-loaded liposomes.
Figure 5B:
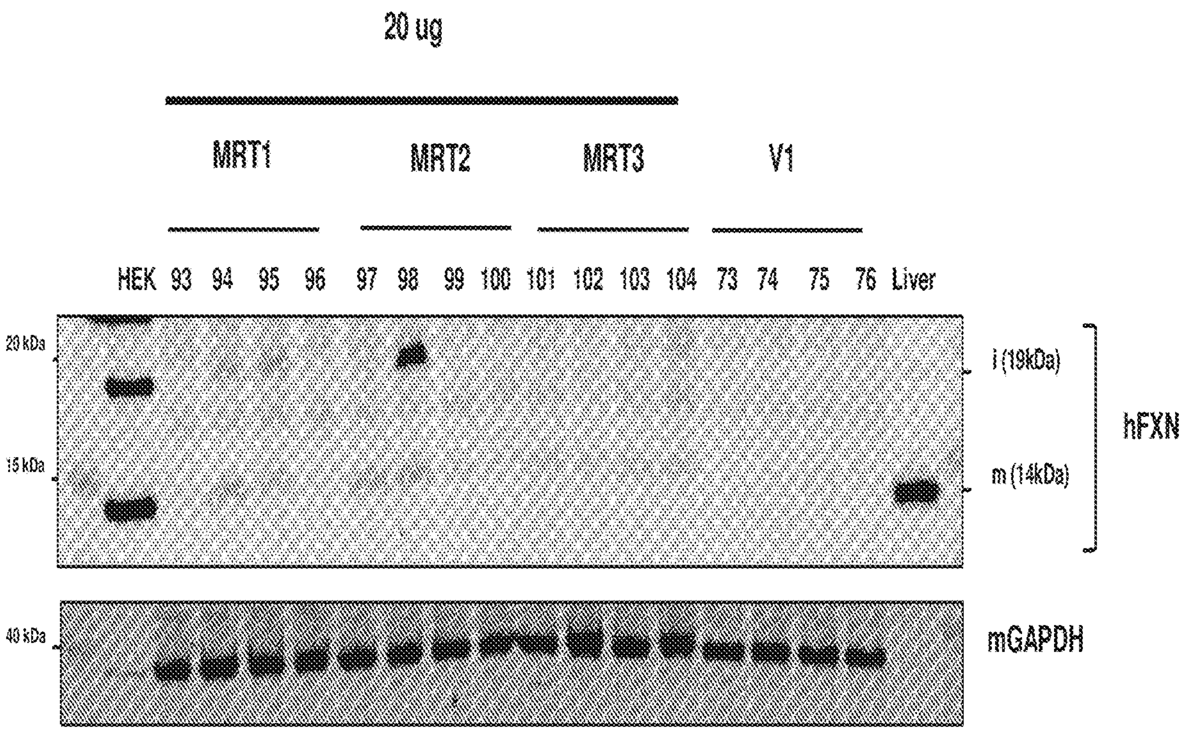
FIG. 5B depicts exemplary detection of human frataxin protein by Western blot in spinal cord samples from mice treated with a single intrathecal dose of hFXN mRNA-loaded liposomes.

Detection of frataxin protein in the tissues of the treated mice was achieved using antibody-based methods (e.g. Western blot). As demonstrated in FIG. 5A, the exogenous human frataxin protein was detected in all three mRNA-liposome combinations (MRT1 comprised SEQ ID NO: 1, MRT2 comprised SEQ ID NO: 2 and MRT comprised SEQ ID NO: 4) in DRG samples when animals were treated with 20 μg of hFXN mRNA. There was some variation, but robust expression was observed in most samples. Similar results were observed in spinal cord samples (FIG. 5B).

Figure 6:
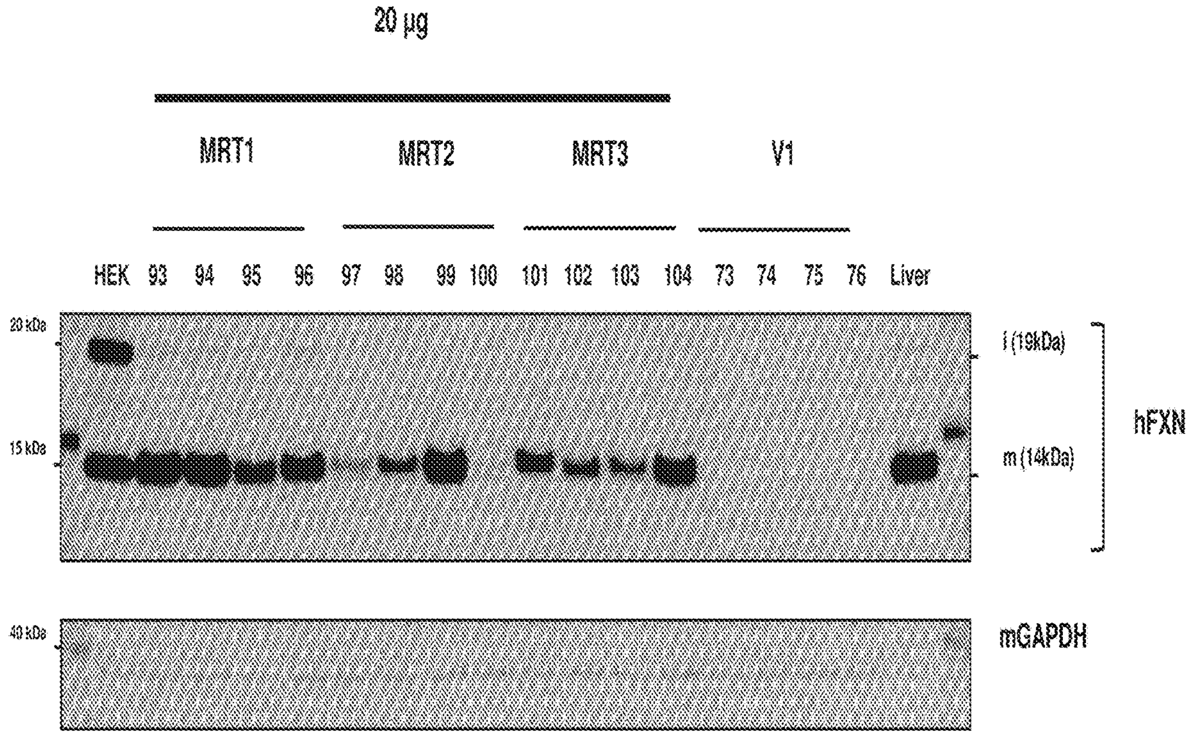
FIG. 6 depicts exemplary detection of human frataxin protein by Western blot in liver samples from mice treated with a single intrathecal dose of hFXN mRNA-loaded liposomes.
Figure 7:
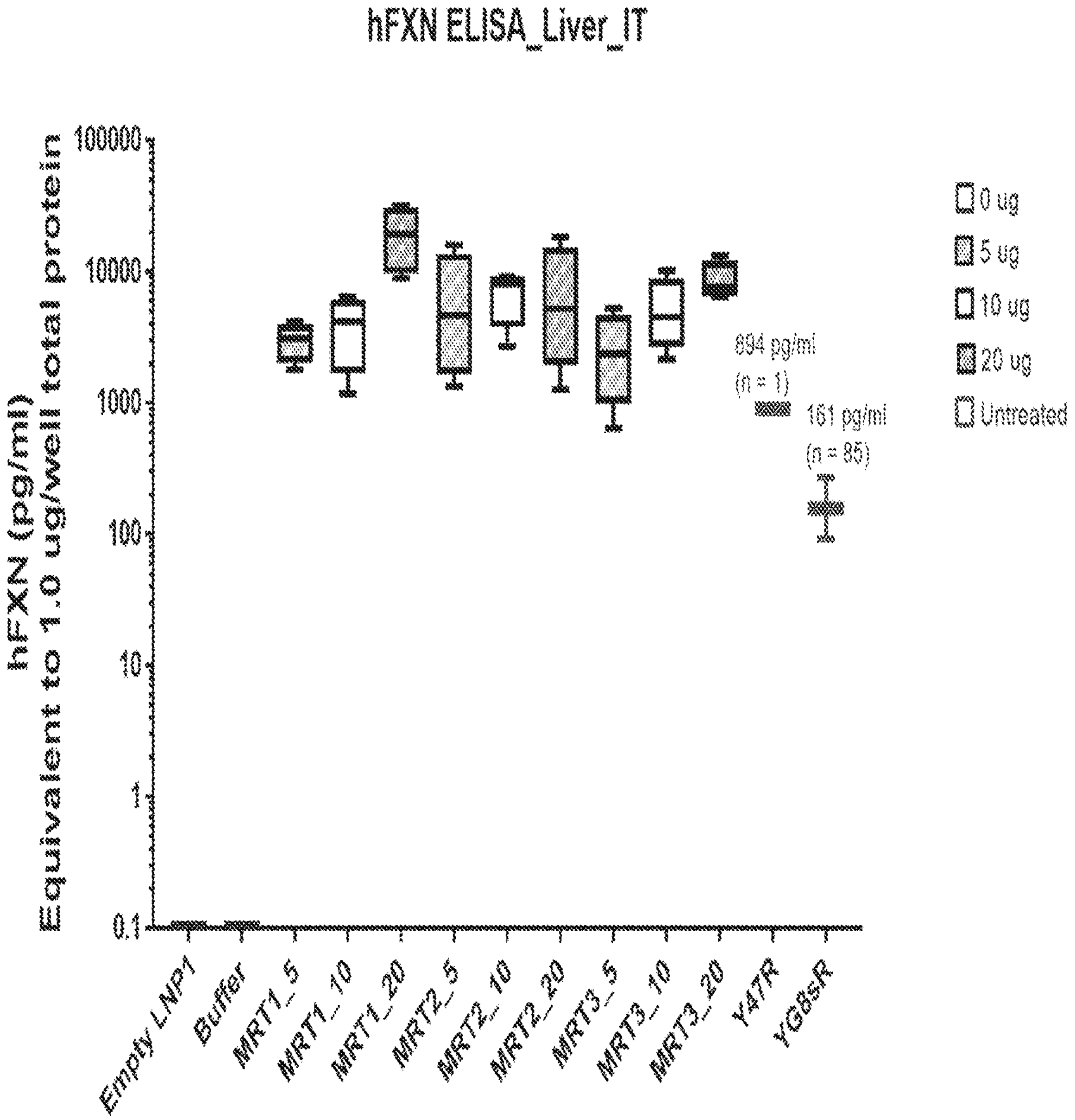
FIG. 7 depicts exemplary detection of human frataxin protein by ELISA in liver samples from mice treated with a single intrathecal dose of hFXN mRNA-loaded liposomes.

Exogenous human frataxin protein was also detected in liver samples from animals treated with 20 μg of hFXN mRNA. As demonstrated in FIG. 6, robust levels of mature human frataxin protein was observed by Western blot, though there was differential expression of the intermediate human frataxin protein observed between the three mRNA treatments, similar to observed results from the IV administration study. Robust human frataxin expression was also detected by ELISA in liver samples from animals treated with all three doses (5 μg, 10 μg and 20 μg) of hFXN mRNA (FIG. 7).

Figure 8A:
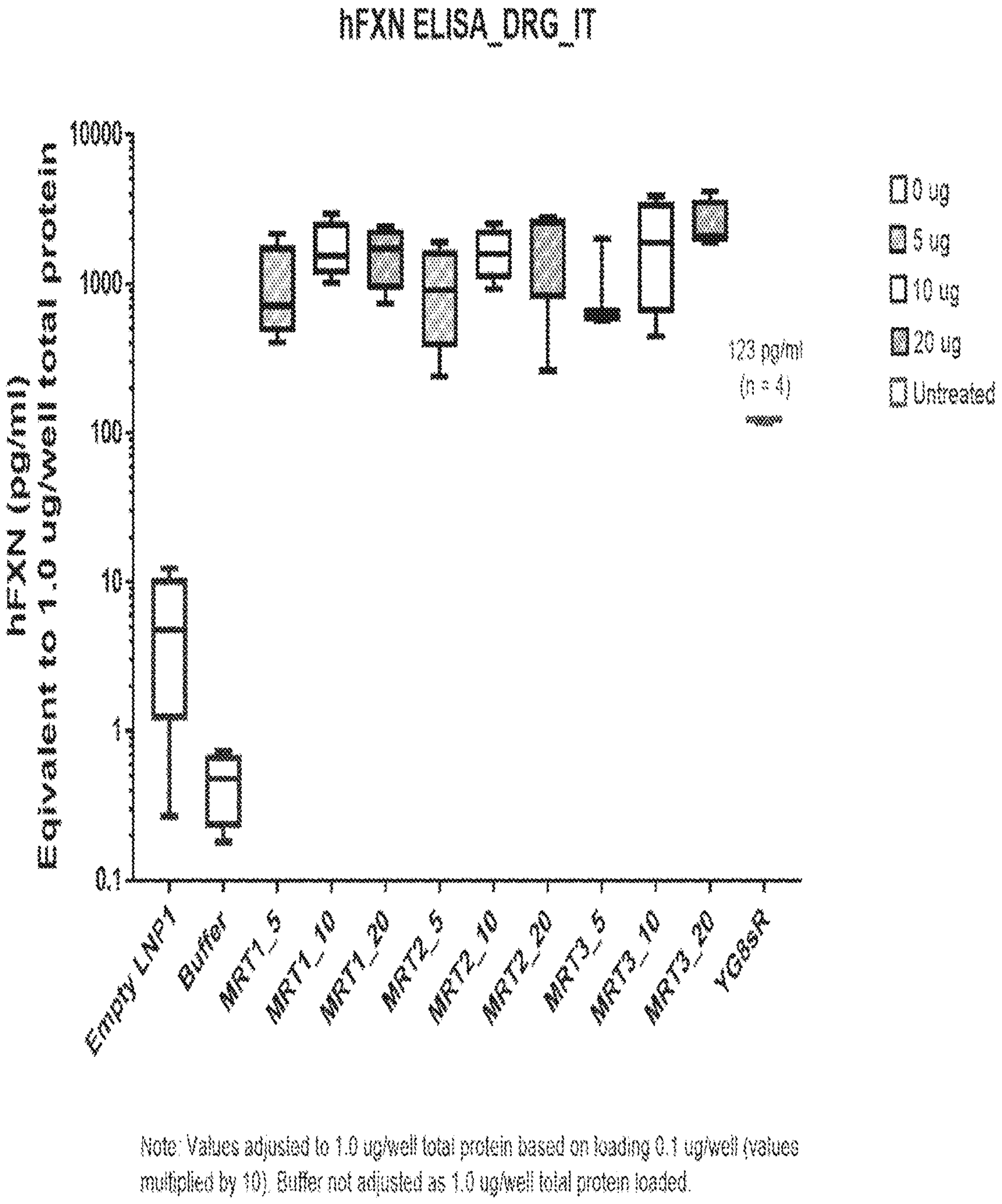
FIG. 8A depicts exemplary detection of human frataxin protein by ELISA in DRG samples from mice treated with a single intrathecal dose of hFXN mRNA-loaded liposomes.
Figure 8B:
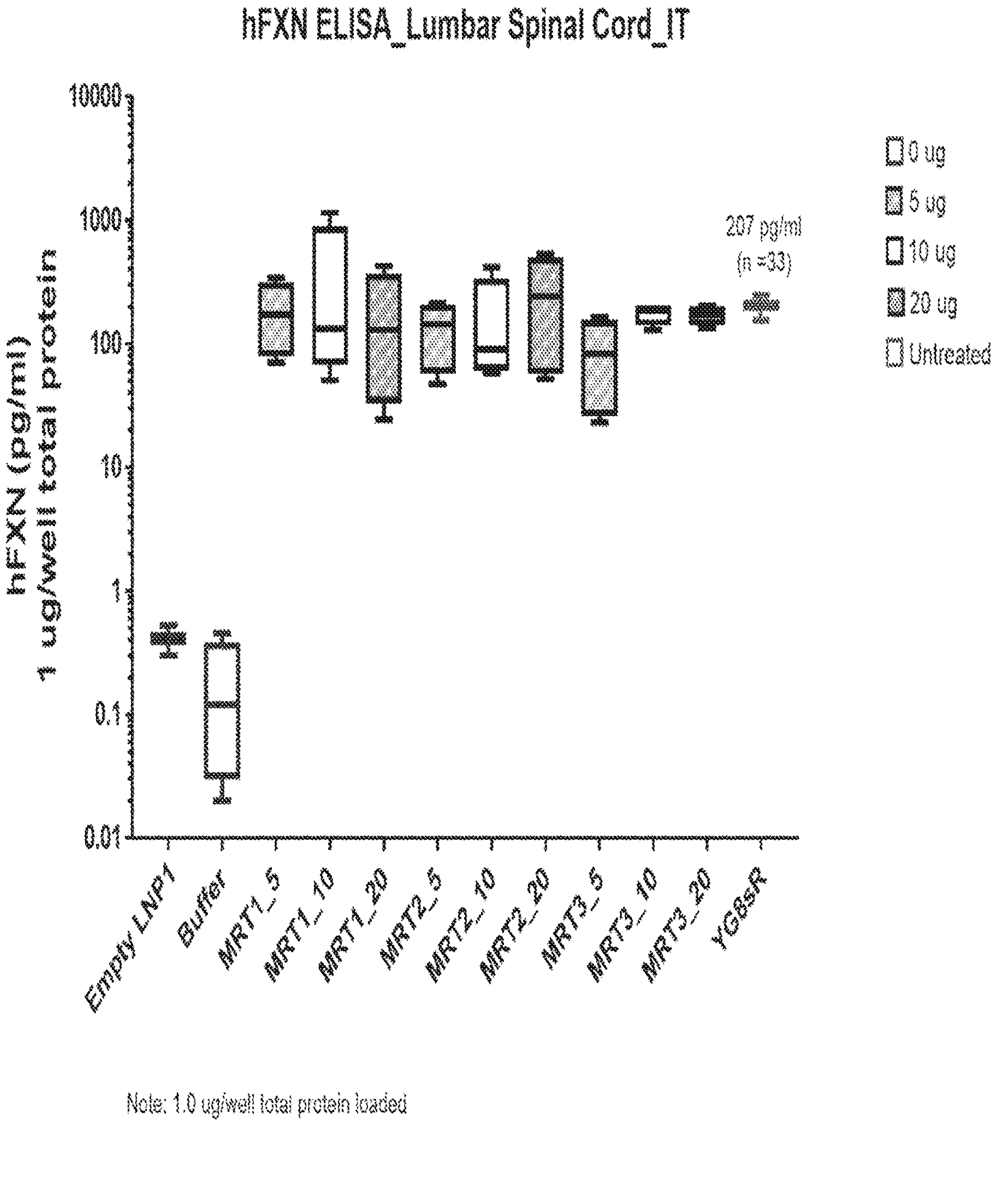
FIG. 8B depicts exemplary detection of human frataxin protein by ELISA in spinal cord samples from mice treated with a single intrathecal dose of hFXN mRNA-loaded liposomes.

Additionally, the mRNA-derived human frataxin protein was detected as a robust signal with ELISA performed on DRG and spinal cord samples. As shown in FIG. 8A, the 5 μg, 10 μg and 20 μg doses of mRNA delivered via IT administration resulted in human frataxin protein being delivered to and detectable in the DRG, as compared to controls. The same doses of mRNA also lead to increased protein expression in the spinal cord, as compared to controls (FIG. 8B).

Figure 9A:
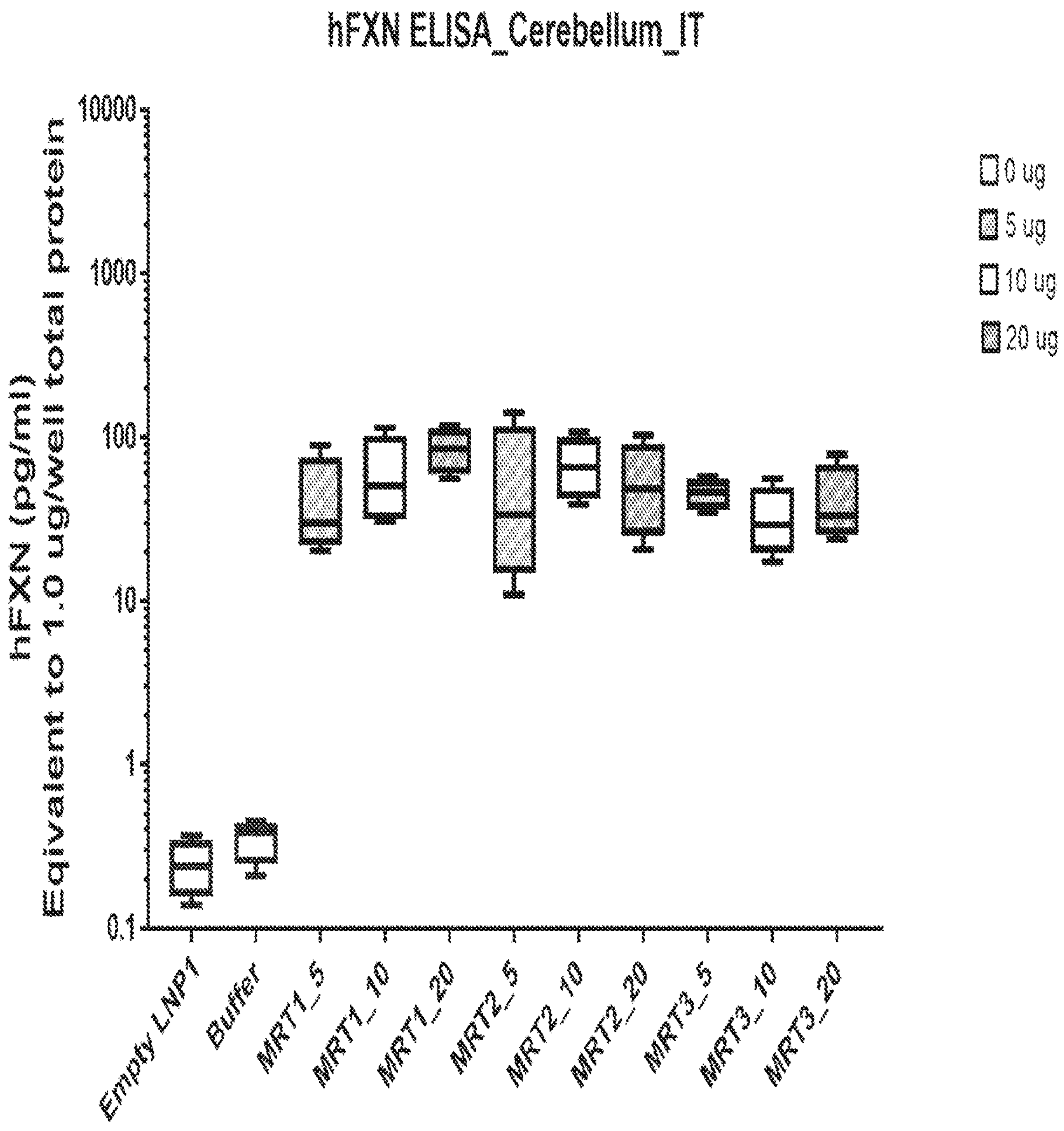
FIG. 9A depicts exemplary detection of human frataxin protein by ELISA in cerebellum samples from mice treated with a single intrathecal dose of hFXN mRNA-loaded liposomes.
Figure 9B:
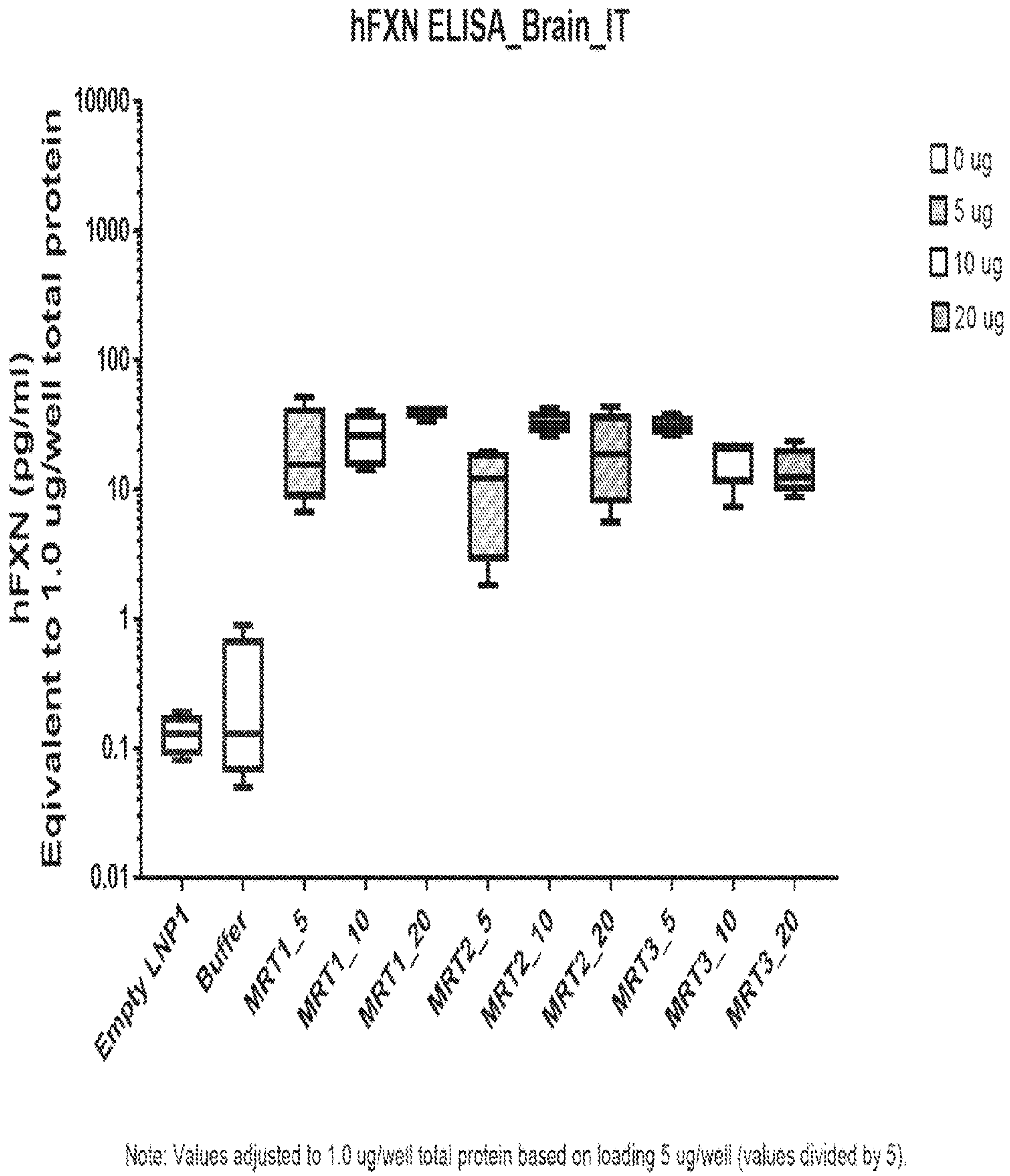
FIG. 9B depicts exemplary detection of human frataxin protein by ELISA in cerebrum samples from mice treated with a single intrathecal dose of hFXN mRNA-loaded liposomes.

Finally, when ELISA was performed on samples from the cerebellum and cerebrum of treated mice (FIG. 9A and FIG. 9B, respectively), the 5 μg, 10 μg and 20 doses of mRNA delivered via IT administration resulted in human frataxin protein being delivered to and detectable in the cerebellum, as compared to controls.

Example 5. Duration of Action of FXN mRNA-Loaded Liposome Nanoparticles In Vivo This example illustrates that administering FXN mRNA-loaded liposomes via intrathecal administration results in sustained in vivo expression of frataxin protein in various tissues important for therapeutic efficacy.

All studies were performed using CD-1 mice. Mice were treated with human FXN mRNA-loaded ICE-based liposomes (MRT4) by a single intrathecal (IT) bolus of a 2 μg/animal or 20 μg/animal dose while under inhaled isofluorane anesthesia. Mice were treated on Day 1 and sacrificed at either Day 4, Day 8, Day 15, or Day 29 (i.e., 3 days, 7 days, 14 days, or 28 days after dose administration, respectfully).

Tissues, including dorsal root ganglia (DRG), and spinal cord of each mouse were harvested, and apportioned into separate parts as described herein. For spinal cord collection, the spinal cords were divided into thoracic and lumbar portions, with the thoracic portion used for testing RNA and the lumbar portion used for testing protein. For DRG collection, the DRG (target of 20 per animal) on each lateral side of T1-L6 were collected. For brain collection, the cerebrum was bisected along the sagittal midline, with half of each region used for testing RNA and the other half for testing protein. For each tissue, both halves used for RNA and protein were snap frozen in LN2.

ELISA Quantification of Frataxin Protein in Mouse Tissue Homogenate

All ELISAs were performed using the commercially available SimpleStep Human Frataxin ELISA Kit (ab176112). Liver or heart or CNS tissues (~30-100 mg) were transferred to Omni tube (2 mL Tube with 2.8 mm Ceramic Beads) and mix with 300-7000 of tissue extraction buffer (RIPA buffer+protease inhibitor) and lysed by using Omni Bead Ruptor 24 Homogenizer at 5000 rpm for 20 seconds. Samples were placed on ice for 20 minutes to allow foam settle, transferred to a new tube, and cleared by centrifuge at 20,000×g for 10 minutes at 4° C. The supernatant was collected and quantified using a BCA assay. The extracts were diluted with 1× Cell Extraction buffer to fit within the linear range of the recombinant hFXN standard, starting at roughly 20 ng/μL. 50 μL of each extract was transferred to a well in 8-well strips in a 96-well plate format and mixed with 50 μL of the Antibody Cocktail. Plates were sealed and incubated at room temp for 70 minutes on a plate shaker set to 400 rpm. Plates were washed 3×350 μL with 1× Wash Buffer PT. Buffer was completely removed by aspiration at each step. The plate was inverted and blotted on clean paper towels to remove excess liquid. 100 μL of TMB Substrate was added to each well and incubated for 10 minutes in the dark on a plate shaker set to 400 rpm. 100 μL of Stop Solution was added to each well, the plate was shaken for 1 minute to mix, and the OD was recorded at 450 nm. Background was subtracted for each well. Readings from the recombinant hFXN standard (0-800 pg/mL) were used to construct a standard curve. A log/log four parameter algorithm (4PL) was used to fit the standard curve and the protein concentrations of the unknown samples were interpolated from that curve.

Results

Figure 10A:
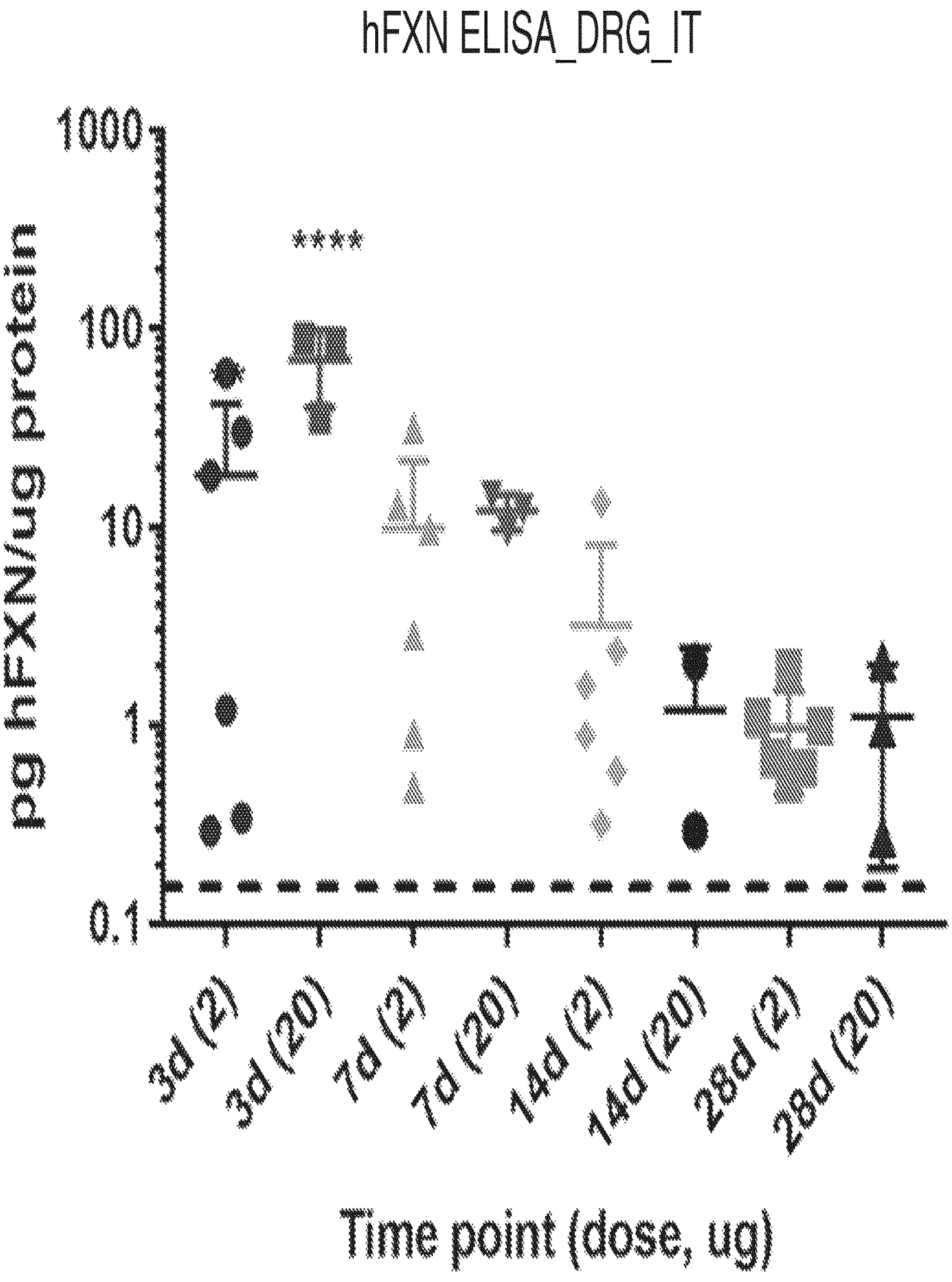
FIG. 10A depicts exemplary detection of human frataxin protein by ELISA in DRG samples from mice treated with a single intrathecal dose of hFXN mRNA-loaded liposomes.

Detection of FXN protein in the DRGs of treated mice was achieved using an antibody-based method (i.e. ELISA). As demonstrated in FIG. 10A, the exogenous FXN protein was detected in animals at 2 μg/animal and 20 μg/animal (MRT 4) for at least 14 days following administration. The baseline levels of human FXN levels in untreated mice is depicted as a dashed line in FIG. 10A.

Figure 10B:
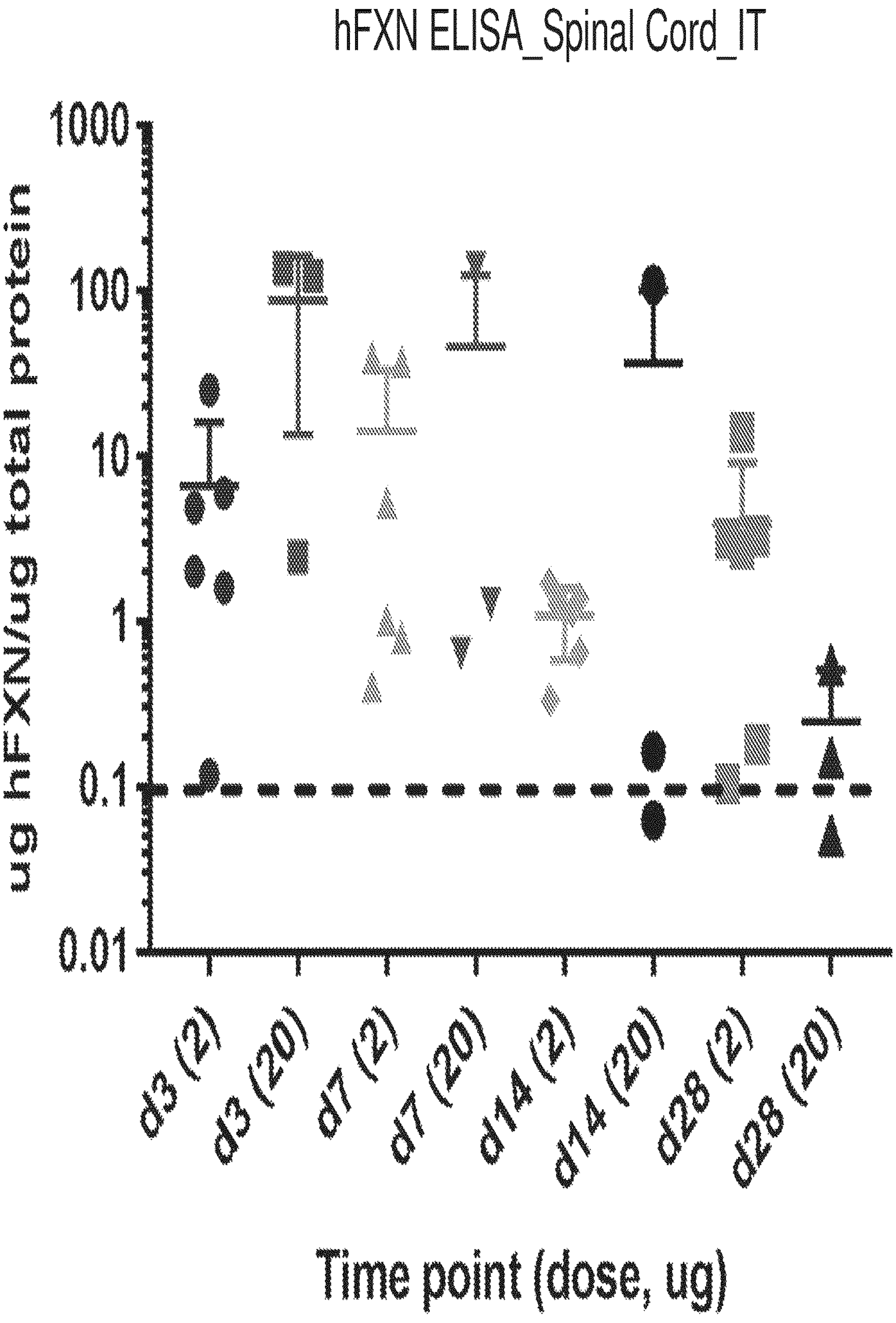
FIG. 10B depicts exemplary detection of human frataxin protein by ELISA in spinal cord samples from mice treated with a single intrathecal dose of hFXN mRNA-loaded liposomes.

Additionally, the mRNA-derived human frataxin protein was detected in the spinal cord with ELISA. AS shown in FIG. 10B, the 2 μg/animal and 20 μg/animal doses of mRNA delivered via IT administration resulted in human frataxin protein being delivered and detectable in the spinal cord, as compared to untreated controls (dashed line in FIG. 10B).

These results demonstrate that delivery of FXN mRNA-loaded liposomes according to the present invention results in sustained in vivo expression of frataxin protein in those tissues important for treatment of treating Friedreich's ataxia.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A pharmaceutical composition for treating Friedreich's ataxia (FRDA), comprising an mRNA encoding a human frataxin protein and wherein the mRNA is encapsulated within a liposome, wherein the mRNA comprises a polynucleotide sequence that is identical to SEQ ID NO: 1, SEQ ID NO: 2, SEQ ID NO. 3, or SEQ ID NO: 4.

2. The pharmaceutical composition of claim 1, wherein the composition is formulated for intravenous (IV) delivery or intrathecal (IT) delivery.

3. The pharmaceutical composition of claim 1, wherein the composition comprises mRNA at an amount of at least 1, 2, 3, 4, 5, 10, or 20 μg.

4. The pharmaceutical composition of claim 1, wherein the mRNA further comprises the 5' untranslated region (UTR) sequence of SEQ ID NO: 6.

5. The pharmaceutical composition of claim 1, wherein the mRNA comprises a polynucleotide sequence that is identical to SEQ ID NO: 1.

6. The pharmaceutical composition of claim 1, wherein the mRNA comprises a polynucleotide sequence that is identical to SEQ ID NO: 2.

7. The pharmaceutical composition of claim 1, wherein the mRNA comprises a polynucleotide sequence that is identical to SEQ ID NO: 3.

8. The pharmaceutical composition of claim 1, wherein the mRNA comprises a polynucleotide sequence that is identical to SEQ ID NO: 4.

9. The pharmaceutical composition of claim 1, wherein the mRNA comprises one or more modified nucleotides selected from the group consisting of pseudouridine, N-1-methy 1-pseudouridine, 2-aminoadenosine, 2-thiothymi dine, pyrrolopyrimidine, 3-methyl adenosine, 5-methylcytidine, C-5 propynyl-cytidine, C-5 propynyl-uridine, 2-aminoadenosine, C5-bromouridine, C5-fluorouri dine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O (6)-methylguanine, 2-thiocyti dine, 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, 1-methyl-inosine, pseudouracil, dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5-methoxycarbonylmethyl-uracil, 5-methoxy-uracil, uracil-5-oxyacetic acid methyl ester, uracil-5-oxyacetic acid, 1-methyl-pseudouracil, queosine, beta-D-mannosyl-queosine, wybutoxosine, phosphoramidates, phosphorothioates, methylphosphonates, 7-deazaguanosine, 5-methylcytosine and inosine.

10. The pharmaceutical composition of claim 1, wherein the liposome comprises one or more cationic lipids, one or more non-cationic lipids, and one or more PEG-modified lipids.

11. The pharmaceutical composition of claim 10, wherein the one or more cationic lipids comprise a cationic lipid selected from the group consisting of C12-200, MC3, DLinDMA, DLinkC2DMA, cKK-E12, ICE (imidazole cholesterol ester), HGT5000, HGT5001, OF-02, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, DLin-K-DMA, DLin-K-XTC2-DMA, HGT4003, and combinations thereof.

12. The pharmaceutical composition of claim 10, wherein the one or more non-cationic lipids comprise a non-cationic lipid selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG dioleoylphosphatidylglycerol) and combinations thereof.

13. The pharmaceutical composition of claim 10, wherein the liposome further comprises one or more cholesterol-based lipids.

14. The pharmaceutical composition of claim 10, wherein the liposome further comprises a sphingomyelin.

* * * * *